United States Patent [19]

Bartley et al.

[11] Patent Number: 5,795,569
[45] Date of Patent: Aug. 18, 1998

[54] MONO-PEGYLATED PROTEINS THAT STIMULATE MEGAKARYOCYTE GROWTH AND DIFFERENTIATION

[75] Inventors: Timothy D. Bartley, Thousand Oaks; Jakob M. Bogenberger, Camarillo; Robert A. Bosselman; Pamela Hunt, both of Thousand Oaks; Olaf B. Kinstler, Oxnard; Babru B. Samal, Moorpark, all of Calif.

[73] Assignee: Amgen Inc., Thousand Oaks, Calif.

[21] Appl. No.: 321,488

[22] Filed: Oct. 12, 1994

Related U.S. Application Data

[63] Continuation-in-part of Ser. No. 252,628, May 31, 1994, which is a continuation-in-part of Ser. No. 221,768, Mar. 31, 1994, abandoned.

[51] Int. Cl.$^6$ .............................. C07K 1/113; C07K 14/52; A61K 38/19
[52] U.S. Cl. .......................... 424/85.1; 530/402; 530/351; 435/69.5; 930/140
[58] Field of Search ................................... 530/351, 402; 536/23.5; 424/85.1, 195.1, 195.11; 435/69.5, 188; 930/140

[56] References Cited

U.S. PATENT DOCUMENTS

| | | | |
|---|---|---|---|
| 4,002,531 | 1/1977 | Royer | 195/69 |
| 4,179,337 | 12/1979 | Davis et al. | 435/181 |
| 4,301,144 | 11/1981 | Iwashita et al. | 514/6 |
| 4,609,546 | 9/1986 | Hiratani | 424/78.3 |
| 4,640,835 | 2/1987 | Shimizu et al. | 424/94.63 |
| 4,670,417 | 6/1987 | Iwasaki et al. | 514/6 |
| 4,810,643 | 3/1989 | Souza | 435/69.5 |
| 4,847,325 | 7/1989 | Shadle et al. | 530/351 |
| 4,904,584 | 2/1990 | Shaw | 435/69.4 |
| 5,032,396 | 7/1991 | Williams | 424/85.2 |
| 5,087,448 | 2/1992 | Burstein | 424/85.2 |
| 5,128,449 | 7/1992 | McDonald | 530/351 |
| 5,215,895 | 1/1993 | Bennett et al. | 435/69.52 |
| 5,250,732 | 10/1993 | Kogan et al. | 564/221 |
| 5,260,417 | 11/1993 | Grant et al. | 530/351 |
| 5,264,209 | 11/1993 | Mikayama et al. | 424/85.2 |
| 5,498,698 | 3/1996 | Yamaguchi et al. | 530/399 |

FOREIGN PATENT DOCUMENTS

| | | |
|---|---|---|
| 0 260 918 | 3/1988 | European Pat. Off. . |
| 0 314 415 | 5/1989 | European Pat. Off. . |
| 154 316 | 9/1989 | European Pat. Off. . |
| 0 335 423 | 10/1989 | European Pat. Off. . |
| 0 354 898 | 2/1990 | European Pat. Off. . |
| 0 401 384 | 12/1990 | European Pat. Off. . |
| 0 442 724 | 8/1991 | European Pat. Off. . |
| 0 473 268 | 3/1992 | European Pat. Off. . |
| 0 539 167 | 4/1993 | European Pat. Off. . |
| 0 583 884 | 2/1994 | European Pat. Off. . |
| WO 89/06546 | 7/1989 | WIPO . |
| WO 90/00568 | 1/1990 | WIPO . |
| WO 90/03397 | 4/1990 | WIPO . |
| WO 90/04606 | 5/1990 | WIPO . |
| WO 90/12108 | 10/1990 | WIPO . |
| WO 90/12877 | 11/1990 | WIPO . |
| WO 91/02001 | 2/1991 | WIPO . |
| WO 91/18925 | 12/1991 | WIPO . |
| WO 92/00319 | 1/1992 | WIPO . |
| WO 92/06178 | 4/1992 | WIPO . |
| WO 92/06712 | 4/1992 | WIPO . |
| WO 92/07074 | 4/1992 | WIPO . |
| WO 92/12177 | 7/1992 | WIPO . |
| WO 92/13075 | 8/1992 | WIPO . |
| WO 92/17500 | 10/1992 | WIPO . |
| WO 93/00109 | 1/1993 | WIPO . |
| WO 93/00433 | 1/1993 | WIPO . |
| WO 93/16106 | 6/1993 | WIPO . |
| WO 93/13132 | 7/1993 | WIPO . |
| WO 95/18858 | 7/1995 | WIPO . |
| WO 95/21626 | 8/1995 | WIPO . |
| WO 95/21919 | 8/1995 | WIPO . |
| WO 95/21920 | 8/1995 | WIPO . |
| WO 95/22984 | 8/1995 | WIPO . |

OTHER PUBLICATIONS

Arriaga et al., "Interrelationship between Mitosis and Endomitosis in Cultures of Human Megakaryocyte Progenitor Cells", Blood, 69(2):486–492 (Feb. 1987).

Asano et al., "In Vivo Effects of Recombinant Human Interleukin–6 in Primates: Stimulated Production of Platelets", Blood, 75(8):1602–1605 (Apr. 15, 1990).

Ballen et al., "Differential Activation of Protein Kinase C Isoforms in Phorbol Ester–Stimulated Megakaryocytic Maturation", Blood, 84(10):Abstract No. 1297 (Nov. 15, 1994).

Ballen et al., "The Induction of Polyploidy in a Human Megakaryocytic Cell Line by Agents Which Perturb Mitotic Spindle Formation", Blood, 84(10):Abstract No. 1297 (Nov. 15,1994).

Ballmaier et al., "Analysis of Expression of Megakaryocyte Growth and Development Factor mRNA in Various Human Normal and Malignant Tissues", Blood, 84(10):Abstract No. 950 (Nov. 15, 1994).

Banu et al., "Modulation of Megakaryocytopoiesis by Human C–MPL Ligand", Blood, 84(10):Abstract No. 1545 (Nov. 15, 1994).

Bénit et al., "Characterization of mpl Cytoplasmic Domain Sequences Required for Myeloproliferative Leukemia Virus Pathogenicity", J. Virol., 68(8):5270–5274 (Aug. 1994).

(List continued on next page.)

Primary Examiner—Lorraine M. Spector
Attorney, Agent, or Firm—Robert R. Cook; Ron K. Levy; Steven M. Odre

[57] ABSTRACT

Disclosed are novel proteins, referred to as megakaryocyte growth and development factors (MGDFs; also generally referred to as Mpl ligands or thrombopoietin, that have a biological activity of stimulating the growth of megakaryocytes and augmenting the differentiation or maturation of megakaryocytes, ultimately to result in the production of platelets. MGDF derivatives comprising MGDF molecules attached to water soluble polymers, such as polyethylene glycol, are also disclosed, along with methods for their preparation. Also disclosed are processes for obtaining the MGDFs in homogeneous form from natural sources and producing them by recombinant genetic engineering techniques from mammals, including humans.

11 Claims, 22 Drawing Sheets

OTHER PUBLICATIONS

Brody et al., "Thrombopoietin (c–mpl Ligand) Acts Synergistically With Erythropoietin and Stem Cell Factor to Enhance Murine Megakaryocyte Colony Growth and Increases Megakaryocyte Polyploidy in vitro", *Blood*, 84(10):Abstract No. 1304 (Nov. 15, 1994).

Bruno et al., "Effect of Recombinant and Purified Hematopoietic Growth Factors on Human Megakaryocyte Colony Formation", *Exp. Hematol.*, 16:371–377 (1988).

Bruno et al., "Partial Inhibition of the Megakaryocyte–Colony Stimulating Activity of Human Interleukin–3 By Antisense Oligonucleotides to the Proto–Oncogene C–MPL", *Blood*, 84(10):Abstract No. 1296 (Nov. 15, 1994).

Burstein et al., "Leukemia Inhibitory Factor and Interleukin–11 Promote Maturation of Murine and Human Megakaryocytes In Vitro", *J. Cell. Physiol.*, 153:305–312 (1992).

Chamow et al., "Modification of CD4 Immunoadhesin with Monomethoxypoly (ethylene glycol) Aldehyde via Reductive Alkylation", *Biocon. Chem.*, 5(2):133–140 (1994).

Chang et al., "Isolation and Characterization of the Human Megakaryocyte Growth and Development Factor (MGDF) Gene", *Blood*, 84(10):Abstract No. 1303 (Nov. 15, 1994).

Chang et al., "Cloning and Characterization of the Human Megakaryocyte Growth and Development Factor (MGDF) Gene", *J. Biol. Chem.*, 270(2):511–514 (Jan. 13, 1995).

Choi et al., "Platelets Generated In Vitro From Proplatelet–Displaying Human Megakaryocytes Are Functional", *Blood*, 85(2):402–413 (Jan. 15, 1995).

Choi et al., "Recombinant Human MGDF (rhuMGDF), A Ligand for c–MPL, Produces Functional Platelets From Megakaryocytes In Vitro", *Blood*, 84(10):Abstract No. 954 (Nov. 15, 1994).

de Alarcon and Schmieder, "Megakaryocyte Colony Stimulating Activity (Mk–CSA) In Serum From Patients Undergoing Bone Marrow Transplantation", *Prog. Clin. Bio. Res.*, 215:335–340 (1986).

de Sauvage, et al., "Thrombocytopenia in C–MPL Deficient Mice", *Blood*, 84(10):Abstract No. 1546 (Nov. 15, 1994).

Debili et al., "The Mpl Receptor Is Expressed in the Megakaryocyte Lineage From Late Progenitors to Platelets", *Blood*, 85(2):391–401 (1995).

Delgado et al., "Coupling of Poly(ethylene glycol) to Albumin under Very Mild Conditions by Activation with Tresyl Chloride: Characterization of the Conjugate by Partitioning in Aqueous Two–Phase Systems", *Biotech. App. Biochem.*, 12:119–128 (1990).

Donahue et al., "Human IL–3 and GM–CSF Act Synergistically in Stimulating Hematopoiesis in Primates", *Science*, 241:1820–1823 (Sep. 30, 1988).

Drachman et al., "The c–MPL Ligand (Thrombopoietin) Stimulates Tyrosine Phosphorylation" *Blood*, 84(10):Abstract No. 1544 (Nov. 15, 1994).

Eaton et al., "Biological Activity of Human Thrombopoietin (TPO), the C–MPL Ligand, and TPO Variants and the Chromosomal Localization of TPO", *Blood*, 84(10):Abstract No. 948 (Nov. 15, 1994).

Erickson–Miller, "Megakaryocyte colony–stimulating factor (Meg–CSF) is a unique cytokine specific for the megakaryocyte lineage", *British Jour. Haematol.*, 84:197–203 (1993).

Erikson–Miller et al., in *Blood Cell Growth Factors: their present and future use in hematology and oncology*, pp. 204–220 (Murphy ed., AlphaMed Press, Dayton, Ohio) (1992).

Evatt et al., "Partial Purification of Thrombopoietin From the Plasma of Thrombocytopenic Rabbits", *Blood*, 54:377–388 (1979).

Evatt et al., "Thrombopoietic activity of fractions of rabbit plasma: studies in rabbits and mice*", *J. Lab. Clin. Med.*, 83(3):364–371 (Mar. 1974).

Foster et al., "Human thrombopoietin: Gene structure, cDNA sequence, expression, and chromosomal localization", *Proc. Natl. Acad. Sci. USA*, 91:13023–13027 (Dec. 1994).

Francis, "Protein modification and fusion proteins", *Focus on Growth Factors*, 3(2):4–10 (1992).

Gachet et al., "Characterization of Functional ADP Purinoceptors on a Human Megakaryocytic Cell Line", *Blood*, 84(10):Abstract No. 1288 (Nov. 15, 1994).

Gewirtz and Calabretta, "Molecular Regulation of Human Megakaryocyte Development", *Int. J. Cell Cloning*, 8:267–276 (1990).

Gewirtz in *In Vitro Regulation Of Human Megakaryocyte Maturation, The Biology of Hematopoiesis*, pp. 123–132 (Wiley–Liss, Inc.) (1990).

Gordon and Hoffman, "Growth Factors Affecting Human Thrombocytopoiesis: Potential Agents for the Treatment of Thrombocytopenia", *Blood*, 80(2):302–307 (Jul. 15, 1992).

Greenberg et al., "In Vitro Stimulation of Megakaryocyte Maturation by Megakaryocyte Stimulatory Factor*", *J. Biol. Chem.*, 262(7):3269–3277 (Mar. 5, 1987).

Groopman, "Capturing the unicorn", *Current Biology*, 4(11):1016–1018 (1994).

Grossi et al., "Biological Characterization of Partially Purified Human Urinary Thrombopoietin", *Hematologica*, 72:291–295 (1987).

Gurney et al., "Thrombocytopenia in c–mpl–Deficient Mice", *Science*, 265:1445–1447 (Sep. 2, 1994).

Hammond et al., "Thrombopoietin (TPO) Activates Platelets In Vitro", *Blood*, 84(10):Abstract No. 2121 (Nov. 15, 1994).

Han et al., "Megakaryocytopoiesis: characterization and regulation in normal and pathologic states", *Int. J. Hematol.*, 54:3–14 (1991).

Harker, "Regulation of thrombopoiesis", *Am. J. Physiol.*, 218(5):1376–1380 (May 1970).

Hill and Levin, "Partial Purification of Thrombopoietin Using Lectin Chromatography", *Exp. Hematol.*, 14:752–759 (1986).

Hill et al., "Correlation of in vitro and in vivo Biological Activities During the Partial Purification of Thrombopoietin", *Exp. Hematol.*, 20:354–360 (1992).

Hill et al., "Evidence That Interleukin–6 Does Not Play a Role in the Stimulation of Platelet Production After Induction of Acute Thrombocytopenia", *Blood*, 80(2):346–351 (Jul. 15, 1992).

Hill et al., "The Effect of Partially Purified Thrombopoietin on Guinea Pig Megakaryocyte Ploidy in vitro", *Exp. Hematol.*, 17:903–907 (1989).

Hoffman, "New Insights into the Regulation of Human Megakaryocytopoiesis", *Blood Cells*, 13:75–86 (1987).

Hoffman, "Regulation of Megakaryocytopoiesis", *Blood*, 74(4):1196–1212 (Sep. 1989).

Hoffman et al., "Assay of an Activity in the Serum of Patients with Disorders of Thrombopoiesis that Stimulates Formation of Megakaryocytic Colonies", *N. Eng. J. Med.*, 305(10):533–538 (Sep. 3, 1981).

Hoffman et al., "Purfication and Partial Characterization of a Megakaryocyte Colony–stimulating Factor from Human Plasma", *J. Clin. Invest.*, 75:1174–1182 (1985).

Hokom et al., "Regulation of Proplatelet Formation in Guinea Pig and Human Megakaryocytes", *Molecular Biology of Hematopoiesis*, 3:15–31 (1994).

Hunt et al., "The effect of the platelet–derived glycosaminoglycan serglycin on in vitro proplatelet–like process formation", *Exp. Hematol.*, 21:1295–1304 (1993).

Hunt et al., "Megakaryocyte Growth and Development Factor (MGDF) is a Potent, Physiological Regulator of Platelet Production in Normal and Myelocompromised Animals," *Blood*, 84(10):Abstract No. 1547 (Nov. 15, 1994).

Hunt et al., "Megakaryocyte proplatelet–like process formation in vitro is inhibited by serum prothrombin, a process which is blocked by matrix–bound glycosaminoglycans", *Exp. Hematol.*, 21:372–381 (1993).

Hunt et al., "Purification and cloning of a megakaryocyte growth and development factor: A novel cytokine found in aplastic plasma", *Exp. Hematol.*, 22(8):838, Abstract No. 605 (Aug. 1994).

Ishibashi and Burstein, "Interleukin 3 Promotes the Differentiation of Isolated Single Megakaryocytes", *Blood*, 67(5):1512–1514 (May 1986).

Ishibashi et al., "Human interleukin 6 is a direct promoter of maturation of megakaryocytes in vitro", *Proc. Natl. Acad. Sci. USA*, 86:5953–5957 (Aug. 1989).

Jorgensen et al., "Thrombopoietin Induces Megakaryocytic Differentiation of Embryonic Stem Cells in Culture", *Blood*, 84(10):Abstract No. 1301 (Nov. 15, 1994).

Kato et al., "Purification and Characterization of Thrombopoietin Derived From Thrombocytopenic Rat Plasma", *Blood*, 84(10):Abstract No. 1300 (Nov. 15, 1994).

Kaushansky et al., "Promotion of megakaryocyte progenitor expansion and differentiation by the c–Mpl ligand thrombopoietin", *Nature*, 369.568–571 (Jun. 16, 1994).

Kaushansky et al., "The molecular and cellular biology of the Mpl–ligand; properties consistent with its identity as thrombopoietin", Workshop on Megakaryocytopoiesis and Platelet Production, p. 16, Maryland (Aug. 18–19, 1994).

Kaushansky et al., "Thrombopoietin (Tpo), the MPL–Ligand, is the Primary Regulator of Megakaryocyte (Mk) Development and Maturation", *Blood*, 84(10):Abstract No. 951 (Nov. 15, 1994).

Kawakita et al, "Characterization of Human Megakaryocyte Colony–Stimulating Factor in the Urinary Extracts From Patients With Aplastic Anemia and Idiopathic Thrombocytopenic Purpura", *Blood*, 61(3):556–560 (Mar. 1983).

Kawakita et al., "Human urinary megakaryocyte colony–stimulating factor in thrombopoietic disorders", *Br. J. Haematol.*, 62:715–722 (1986).

Kawakita et al., "Thrombopiesis and Megakaryocyte Colony–stimulating Factors in the Urine of Patients with Idiopathic Thrombocytopenic Purpura", *Br. J. Haematol.*, 48:609–615 (1981).

Kellar et al., "The Effects of Thrombopoietic Activity of Rabbit Plasma Fractions on Megakaryocytopoiesis in Agar Cultures", *Exp. Hematol.*, 16:262–267 (1988).

Kellar et al., "Thrombopoietin–Induced Stimulation of Megakaryocyte–Enriched Bone Marrow Cultures", *Int. Cong. Thromb. Haem.*, 42(1):283 (Abs P5–028/0668) (1979).

King and Bishop, "Two Companies Claim Victory in Platelet Race", *The Wall Street Journal*, pp. B1 & B4 (Dow Jones & Company, Inc) (Jun. 16, 1994).

Kuter and Rosenberg, "Appearance of a Megakaryocyte Growth–Promoting Activity, Megapoietin, During Acute Thrombocytopenia in the Rabbit", *Blood*, 84(5):1464–1472 (Sep. 1, 1994).

Kuter et al., "The purification of megapoietin: a physiological regulator of megakaryocyte growth and platelet production", Workshop on Megakaryocytopoiesis and Platelet Production, Aug. 18–19, 1994, Maryland, USA, p. 18.

Kuter et al., "The purification of megapoietin: A physiological regulator of megakaryocyte growth and platelet production", *Proc. Natl. Acad. Sci. USA*, 91:11104–11108 (Nov. 1994).

Kuter et al., "The Purification and Physiological Characteristics of Ovine Thrombopoietin", *Blood*, 84(10):Abstract No. 953 (Nov. 15, 1994).

Lehrman, "Four–way fight brews over long–sought platelet factor", *Biotechnology Newswatch*, pp. 1 & 3 (Jul. 4, 1994).

Leven and Yee, "Megakaryocyte Morphogenesis Stimulated In Vitro by Whole and Partially Fractionated Thrombocytopenic Plasma: A Model System for the Study of Platelet Formation", *Blood*, 69(4):1046–1052 (Apr. 1987).

Levin in *Molecular Biology and Differentiation of Megakaryocytes*, pp. 1–10, (Wiley–Liss, Inc.)(1990).

Levine, "Culture In Vitro of Isolated Guinea Pig Megakaryocytes; Recovery, Survival, Morphologic Changes, and Maturation", *Blood*, 50(4):713–725 (Oct. 1977).

Li et al., "Purification of a Megakaryocyte Growth and Development Factor from Aplastic Canine and Porcine Plasma", *Blood*, 84(10):Abstract No. 1307 (Nov. 15, 1994).

Lok and Foster, "The Structure, Biology and Potential Therapeutic Applications of Recombinant Thrombopoietin", *Stem Cells*, 12:586–598 (1994).

Lok et al., "Cloning and expression of murine thrombopoietin cDNA and stimulation of platelet production in vivo", *Nature*, 369:565–568 (Jun. 16, 1994).

Lok et al., "Thrombopoietin: Cloning and Biological Activity", *Exp. Hematol.*, 22(8):838, Abstract No. 606 (Aug. 1994).

Matsuda et al., "Purification and Characterization of a Novel Growth Factor (FF–GF) Synthesized by Rat Hepatoma Cell Line, FF101", *Biochem. Biophys. Res. Com.*, 189(2):654–661 (Dec. 15, 1992).

Mayer et al., "Recombinant Human Leukemia Inhibitory Factor Induces Acute Phase Proteins and Raises the Blood Platelet Counts in Nonhuman Primates", *Blood*, 81(12):3226–3233 (Jun. 15, 1993).

Mazur and Cohen, "Basic concepts of hematopoiesis and the hematopoietic growth factors", *Clin. Pharmacol. Ther.*, 46(3):250–256 (Sep. 1989).

Mazur and South, "Human Megakaryocyte Colony–stimulating Factor in Sera from Aplastic Dogs: Partial Purification, Characterization, and Determination of Hematopoietic Cell Lineage Specificity", *Exp. Hematol.*, 13:1164–1172 (1985).

Mazur at al., "Human Serum Megakaryocyte Colony–stimulating Activity Increases in Response to Intensive Cytotoxic Chemotherapy", *Exp. Hematol.*, 12:624–628 (1984).

Mazur et al., "Human Serum Megakaryocyte Colony–Stimulating Activity Appears To Be Distinct From Interleukin–3, Granulocyte–Macrophage Colony–Stimulating Factor, and Lymphocyte–Conditioned Medium", *Blood*, 76(2):290–297 (Jul. 15, 1990).

McCarthy and Kaushansky, "Murine Thrombopoietin mRNA Levels are Modulated by Platelet Count", *Blood*, 84(10):Abstract No. 949 (Nov. 15, 1994).

McDonald, "Assay of Thrombopoietin Utilizing Human Sera and Urine Fractions", Biochem. Med., 13:101–110 (1975).

McDonald, "The Regulation of Megakaryocyte and Platelet Production", Int. J. Cell Cloning, 7:139–155 (1989).

McDonald, "Thrombopoietin: Its Biology, Clinical Aspects, and Possibilities", J. Pediatric Hematology/Oncology, 14(1):8–21 (1992).

McDonald, "Thrombopoietin: Its Biology, Purification, and Characterization", Exp. Hematol., 16:201–205 (1988).

McDonald et al., "A Four–step Procedure for the Purification of Thrombopoietin", Exp. Hematol., 17:865–871 (1989).

McDonald et al., "Purification And Characterization Of A Thrombocytopoiesis–stimulating Factor From Human Embryonic Kidney Cell Cultures", Exp. Hematol., 16:488a (1988).

McDonald et al., "Studies on the purification of thrombopoietin from kidney cell culture medium", J. Lab. Clin. Med., 106:162–174 (Aug. 1985).

McDonald et al., "Thrombopoietin From Human Embryonic Kidney Cells Is the Same Factor as c–mpl–Ligand", Blood, 85:292–294 (1995).

McDonald et al., "Thrombopoietin production by human embryonic kidney cells in culture", J. Lab. Clin. Med., 85(1):59–66 (Jan. 1975).

McGoff et al., "Analysis of Polyethylene Glycol Modified Superoxide Dismutase by Chromatographic, Electrophoretic, Light Scattering, Chemical and Enzymatic Methods", Chem. Pharm. Bull., 36(8):3079–3091 (1988).

Metcalf, "Thrombopoietin—at last", Nature, 369:519–520 (Jun. 16, 1994).

Metcalf et al., "Leukemia Inhibitory Factor Can Potentiate Murine Megakaryocyte Production In Vitro", Blood, 77(10):2150–2153 (May 15, 1991).

Methia et al., "Oligodeoxynucleotides Antisense to the Proto–oncogene c–mplSpecifically Inhibit In Vitro Megakaryocytopoiesis", Blood, 82(5):1395–1401 (Sep. 1, 1993).

Mignotte et al., "Structure and Transcription of the Human c–mpl Gene (MPL)", Genomics, 20:5–12 (1994).

Miura et al., "Increase in Circulating Megakaryocyte Growth–promoting Activity (Meg–GPA) following Sublethal Irradiation Is Not Related to Decreased Platelets", Exp. Hematol., 16:139–144 (1988).

Miura et al., "Increases in Circulating Megakaryocyte Growth–Promoting Activity in the Plasma of Rats Following Whole Body Irradiation", Blood, 63(5):1060–1066 (May 1984).

Miyazaki et al., "Biological Properties of Thrombopoietin (TPO)", Blood, 84(10):Abstract No. 955 (Nov. 15, 1994).

Miyazaki et al., "Isolation and cloning of a novel human thrombopoietic factor"; Exp. Hematol., 22(8):838, Abstract No. 604 (Aug. 1994).

Morgan et al., "Differential Effects of Thrombopoietin (MPL) on Cell lines MB–02 and HU–3 Derived from Patients with Megakaryoblastic Leukemia", Blood, 84(10):Abstract No. 1306 (Nov. 15, 1994).

Murphy, "Megakaryocyte Colony–Stimulating Factor and Thrombopoiesis", Hematol./Oncol. Clinics of N. Am., 3(3):465–478 (Sep. 1989).

Neben et al., "Recombinant Human Interleukin–1 1 Stimulates Megakaryocytopoiesis and Increases Peripheral Platelets in Normal and Splenectomized Mice", Blood, 81(4):901–908 (Feb. 15, 1993).

Nichol et al., "A Characterization of the In Vitro Activity of Recombinant Human Megakaryocyte Growth and Development Factor (rhuMGDF) on Human CD34+ Cells", Blood, 84(10):Abstract No. 1299 (Nov. 15, 1994).

Nichol et al., "Enrichment and Characterization of Peripheral Blood–Derived Megakaryocyte Progenitors that Mature in Short–Term Liquid Culture", Stem Cells, 12:494–505 (1994).

Nieuwenhuis and Sixma, "Thrombocytopenia And The Neglected Megakaryocyte", New Eng. J. Med., 327(25):1812–1813 (Dec. 17, 1992).

Odell et al., "Stimulation of Platelet Production by Serum of Platelet–Depleted Rats", Proc. Soc. Biol. Med., 108:428–431 (1961).

Ogami et al., "Molecular cloning and expression of human thrombopoietin (TPO) cDNA" (Lecture No. 2–1F–096, Lecture date, Dec. 14, 1994); 17th Annual Meeting of the Society of Molecular Biology of Japan, Program and Abstracts of Lectures (Nov. 28, 1994).

Ogami et al., "Molecular Cloning and Expression of Thrombopoietin (TPO)", Blood, 84(10):Abstract No. 1289 (Nov. 15, 1994).

Ogata et al., "Partial Purification and Characterization of Human Megakaryocyte Colony–Stimulating Factor (Meg–CSF)", Int. J. Cell Cloning, 8:103–120 (1990).

Ogden, "Thrombopoietin—the erythropoietin of platelets?", TIBTECH, 12:389–390 (Oct. 1994).

Papayannopoulou et al., "The Influence of Mpl–Ligand on the Development of Megakaryocytes From CD34+ Cells Isolated From Bone Marrow, Pheripheral Blood and Cord Blood", Blood, 84(10):Abstract No. 1283 (Nov. 15, 1994).

Paul et al., "Molecular cloning of a cDNA encoding interleukin 11, a stromal cell–derived lymphopoietic and hematopoietic cytokine", Proc. Natl. Acad. Sci. USA, 87:7512–7516 (Oct. 1990).

Penington, "Isotope Bioassay for 'Thrombopoietin'", Br. Med. J., 1:606–608 (Mar. 7, 1970).

Pennisi, "Scientists hail platelet factor's promise", Science News, 146:229 (Oct. 8, 1994).

Sabath et al., "Development of a Cell Line Dependent on MPL Ligand for Proliferation", Blood, 84(10):Abstract No. 1284 (Nov. 15, 1994).

Sada et al., "Resistance to Proteolysis of Antibody Ligands Modified with Polyethylene Glycol", J. Fermentation Bioengineering, 171(2):137–139 (1991).

Samal et al., "Isolation and Expression of Truncated Forms of Megakaryocyte Growth and Development Factor, the MPL Ligand", Blood, 84(10):Abstract No. 1291 (Nov. 15, 1994).

Schick, "Clinical Implications Of Basic Research—Hope For Treatment Of Thrombocytopenia", N. E J. Med., 331(13):875–876 (Sep. 29, 1994).

Shieh et al., "Ex Vivo Expansion of Megakaryocytes and Neutrophil Progenitors From Mobilized Pheripheral Progenitor Cells", Blood, 84(10):Abstract No. 1295 (Nov. 15, 1994).

Shimada et al., "Molecular cloning and expression of rat thrombopoietin cDNA" (Lecture No. 2–1 F–095, Lecture date, Dec. 14, 1994); 17th Annual Meeting of the Society of Molecular Biology of Japan, Program and Abstracts of Lectures (Nov. 28, 1994).

Shimada et al., "Thrombopoietin (TPO) is produced by Liver", Blood, 84(10):Abstract No. 1290 (Nov. 15, 1994).

Shreiner and Levin, "Detection of Thrombopoietic Activity in Plasma by Stimulation of Suppressed Thrombopoiesis", *J. Clin. Invest.*, 49:1709–1713 (1970).

Skoda et al., "Murine c-mpt a member of the hematopoietic growth factor receptor superfamily that transduces a proliferative signal", *EMBO Journal*, 12(7):2645–2653 (1993).

Sohma et al., "Molecular cloning and chromosomal localization of the human thrombopoietin gene", *FEBS Letters*, 353:57–61 (1994).

Sohma et al., "Molecular cloning and chromosomal localization of the human thrombopoietin gene", (Lecture No. 2–1F–097, Lecture date, Dec. 14, 1994); 17th Annual Meeting of the Society of Molecular Biology of Japan, Program and Abstracts of Lectures (Nov. 28, 1994).

Solberg, "Von Willibrand (vWB) pigs and human c–Mpl–ligand", Workshop on Megakaiyocytopoiesis and Platelet Production, Maryland, USA (Aug. 18–19, 1994), p. 17.

Solberg, Jr. et al., "Effects of Recombinant Human Thrombopoietin (rhTPO) on Colony Formation by Human Hematopoietic Stem Cells", *Blood*, 84(10):Abstract No. 1305 (Nov. 15, 1994).

Souyri et al., "A Putative Truncated Cytokine Receptor Gene Transduced by the Myeloproliferative Leukemia Virus Immortalizes Hematopoietic Progenitors", *Cell*, 63:1137–1147 (Dec. 21, 1990).

Sprugel et al., "Recombinant Thrombopoietin Stimulates Rapid Platelet Recovery in Thrombocytopenic Mice", *Blood*, 84(10):Abstract No. 952 (Nov. 15, 1994).

Stahl et al., "Effects of Human Interleukin–6 on Megakaryocyte Development and Thrombocytopoiesis in Primates", *Blood*, 78(6):1467–1475 (Sep. 15, 1991).

Straneva et al., "Effects of Megakaryocyte Colony–stimulating Factor on Terminal Cytoplasmic Maturation of Human Megakaryocytes", *Exp. Hematol.*, 15:657–663 (1987).

Sullivan et al., "Thrombopoietin Ameliorates the Thrombocytopenia in an Animal Model for HIV–Related Thrombocytopenia (MAIDS)", *Blood*, 84(10):Abstract No. 1286 (Nov. 15, 1994).

Sullivan et al., "Thrombopoietin from Human Embryonic Kidney Cells Causes Increased Thrombocytopoiesis and Decreased Erythropoiesis in Mice", *Comp. Haematol. Int.*, 4:63–69 (1991).

Takebe et al., "SRα–Promoter: an Efficient and Versatile Mammalian cDNA Expression System Composed of the Simian Virus 40 Early Promoter and the R–U5 Segment of Human T–Cell Leukemia Virus Type 1 Long Terminal Repeat", *Mol. Cell. Biol.*, 8(1):466–472 (Jan. 1988).

Tayrien and Rosenberg, "Purification and Properties of a Megakaryocyte Stimulatory Factor Present Both in the Serum–free Conditioned Medium of Human Embryonic Kidney Cells and in Thrombocytopenic Plasma*", *J. Biol. Chem.*, 262(7):3262–3268 (Mar. 5, 1987).

Teramura, "Mechanism of platelet production—Is mpl ligand Thrombopoietin?", *Igaku no Ayumi (Japan)*, 171(10):809–813 (Dec. 3, 1994).

Teramura et al., "Clonal Growth of Human Megakaryocyte Progenitors in Serum–free Cultures: Effect of Recombinant Human Interleukin 3", *Exp. Hematol.*, 16:843–848 (1988).

Teramura et al., "Interleukin–11 Enhances Human Megakaryocytopoiesis In Vitro", *Blood*, 79(2):327–331 (Jan. 15, 1992).

Todokoro, "Thrombopoietin–induced Megakaryocytopoiesis and Thrombocytopoiesis", *Cell Eng. (Saibo Kogaku)*, 14(1):76–83 (1995).

Turner et al., "Purification, Biochemical Characterization, and Cloning of a Novel Megakaryocyte Stimulating Factor that has Megakaryocyte Colony Stimulating Activity", *Blood*, 78:1106 279a (abstr., supple. 1) (1991).

Uzan et al., "Production of Megakaryocytes From Murine Embryonic Stem Cells", *Blood*, 84(10):Abstract No. 1285 (Nov. 15, 1994).

Vannucchi et al., "Partial Purification and Biochemical Characterization of Human Plasma Thrombopoietin", *Leukemia*, 2(4):236–240 (Apr. 1988).

Vigon et al., "Characterization of the murine Mpl proto–oncogene, a member of the hematopoietic cytokine receptor family: molecular cloning, chromosomal location and evidence for a function in cell growth", *Oncogene*, 8:2607–2615 (1993).

Vigon et al., "Molecular cloning and characterization of MPL, the human homolog of the v–mploncogene: Identification of a member of the hematopoietic growth factor receptor superfamily", *Proc. Natl. Acad. Sci. USA*, 89:5640–5644 (Jun. 1992).

Wendling et al., "Antisense Oligodeoxynucleotides To MPL Protooneogene Specifically Inhibit Megakaryocytic Differentiation", *Blood*, 80:246a(Abstracts973) (1993).

Wendling et al., "c–Mpl ligand is a humoral regulator of megakaryocytopoiesis", *Nature*, 369:571–574 (Jun. 16, 1994).

Wendling et al., "c–MPL ligand is a humoral regulator of late stages of megakaryocytopoiesis", p. 15, Workshop on Megakaryocytopoiesis and Platelet Production, Maryland, USA (Aug. 18–19, 1994).

Wendling et al., "Factor–Independent Erythropoietic Progenitor Cells in Leukemia Induced by the Myeloproliferative Leukemia Virus", *Blood*, 73(5):1161–1167 (Apr. 1989).

Wendling et al., "MPLV: A Retrovirus Complex Inducting an Acute Myeloproliferative Leukemic Disorder in Adult Mice", *Virol.*, 149:242–246 (1986).

Wendling et al., "Myeloid Progenitor Cells Transformed by the Myeloproliferative Leukemia Virus Proliferate and Differentiate In Vitro Without the Addition of Growth Factors", *Leukemia*, 3(7):475–480 (Jul. 1989).

Williams, "Stimulators Of Megakaryocyte Development And Platelet Production", *Growth Factor Research*, 2:81–95 (1990).

Williams and Levine, "Annotation—The Origin, Development And Regulation Of Megakaryocytes", *Brit. J. Haematol.* 52:173–180 (1982).

Williams et al., "Recombinant Interleukin 6 Stimulates Immature Murine Megakaryocytes", *Exp. Hematol.*, 18:69–72 (1990).

Williams et al., "Two–Factor Requirement for Murine Megakaryocyte Colony Formation", *J. Cell. Physiol.*, 110:101–104 (1982).

Withy et al., "Growth Factors Produced by Human Embryonic Kidney Cells that Influence Megakaryopoiesis Include Erythropoietin, Interleukin 6, and Transforming Growth Factor–Beta", *J. Cell. Physiol.*, 153:362–372 (1992).

Yagi et al., "Effect of C–MPL Ligand/Thrombopoietin on Murine Long Term Bone Marrow Cultures", *Blood*, 84(10):Abstract No. 1292 (Nov. 15, 1994).

Yamaguchi et al., "A Novel Cytokine Exhibiting Megakaryocyte Potentiating Activity From a Human Pancreatic Tumor Cell Line HPC–Y5*", *J. Biol. Chem.*, 269(2):805–808 (Jan. 14, 1994).

Yang et al., "Human IL-3 (Multi-CSF): Identification by Expression Cloning of a Novel Hematopoietic Growth Factor Related to Murine IL-3", Cell, 47:3-10 (1986).

Zeigler et al., "In Vitro Megakaryocytopoietic and Thrombopoietic Activity of c-mpl Ligand (TPO) on Purified Murine Hematopoietic Stem Cells", Blood, 84(12):4045-4052 (Dec. 15, 1994).

Ziegler et al., "In Vitro Megakaryocytopoietic and Thrombopoietic Activity of C-MPL Ligand (TPO) on Purified Murine Hematopoietic Stem Cells", Blood, 84(10):Abstract No. 1282 (Nov. 15, 1994).

Ashizawa, Studies on Thrombopoietin II. Influence of Thrombopoietin on Colony Forming Unit Megakaryocyte (CFU-M), ACTA HAEM. JAP., 42:496-504 (1979).

Bartelmez et al., "Lineage Specific Receptors Used to Identify a Growth Factor for Developmentally Early Hemopoietic Cells: Assay of Hemopoietin-2", J. Cell Physiol., 122:362-369 (1985).

Bruno et al., "Effect of Interleukin 6 on In Vitro Human Megakaryocytopoiesis: Its Interaction with Other Cytokines", Exp. Hematol. 17(10):1038-1043 (1989).

Burstein, "Interleukin 3 Promotes Maturation of Murine Megakaryocytes in Vitro", Blood Cells, 11:469 (1986).

Clutterbuck et al., "Human Interleukin-5 (IL-5) Regulates the Production of Eosinophils in Human Bone Marrow Cultures: Comparison and Interaction With IL-1, IL-3, IL-6 and GMCSF", Blood, 73(6):1504-1512 (1989).

Dexter et al., "Growth and Differentiation in the Hemopoietic System", Ann. Rev. Cell Biol., 3:423-441 (1987).

Ebbe, "Thrombopoietin", Blood, 44:605-608 (1974).

Ebbe et al., "Megakaryocyte Maturation Rate In Thrombocytopenic Rats", 32:787 (1968).

Fisher et al., ed., Separations Using Aqueous Phase Systems, Applications in Cell Biology and Biotechnology, Plenum Press, N.Y., N.Y., 211-213 (1989).

Francis et al., "PEG-Modified Proteins", pp. 235-263 in *Stability of Protein Pharmaceuticals, Part B: In Vivo Pathways of Degradation and Strategies for Protein Stabilization*, Plenum Press, NY (1992).

Geissler et al., "A Regulatory Role of Activated T-Lymphocytes on Human Megakaryocytopoiesis In Vitro", Br. J. Haematol., 60:233-238 (1985).

Geissler et al., "The Role of Erythropoietin, Megakaryocyte Colony-stimulating Factor, and T-cell-derived Factors on Human Megakaryocyte Colony Formation: Evidence for T-cell-mediated and T-cell-independent Stem Cell Proliferation", Exp. Hematol., 15:845-853 (1987).

Ikebuchi et al., "Interleukin 6 Enhancement of Interleukin 3-Dependent Proliferation of Multipotential Hemopoietic Progenitors", Proc. Natl Acad. Sci. USA, 84:9035 (1987).

Kimura et al., "Interleukin 6 is a Differentiation Factor for Human Megakaryocytes In Vitro", Eur. J. Immunol., 20(9):1927-1931 (1990).

Kimura et al., "Megkaryocytopoiesis in the Rat: Response to Thrombocytopenia Induced by Exchange Transfusion", Exp. Hematol., 13:1048 (1985).

Koike et al., "Interleukin-6 Enhances Murine Megakaryocytopoiesis in Serum-Free Culture", Blood, 75(12):2286-2291 (1990).

Long, M., Stem Cells 11:33-40 (1993).

Lotem et al., "Regulation of Megakaryocyte Development by Interleukin-6", Blood, 74(5):1545-1551 (1989).

Mazur, "Megakaryocytopoiesis and Platelet Production: a Review", Exp. Hematol., 15:340-350 (1987).

Mazur et al., "Regulation of Human Megakaryocytopoiesis, An In Vitro Analysis", J. Clin. Invest., 68:733-741 (1981).

McDonald, "Bioassay for Thrombopoietin Utilizing Mice in Rebound Thrombocytosis", Proc. Soc. Exp. Biol. Med., 144:1006-1012 (1973).

McDonald et al., "A Comparison of Mice in Rebound-Thrombocytosis with Platelet-Hypertransfused Mice for the Assay of Thrombopoietin", Scand. J. Haematol., 16:326-334 (1976).

McDonald et al., "Purification and Assay of Thrombopoietin", Exp. Hematol., 2:355-361 (1974).

Morris et al., "Autoimmune Thrombocytopenic Purpura in Homosexual Men", Ann. Intern. Med., 96:714-717 (1982).

Odell et al., "Stimulation of Megakaryocytopoiesis by Acute Thrombocytopenia in Rats", Blood, 48:765 (1976).

Metcalf et al., "Growth of Mouse Megakaryocyte Colonies in Vitro", Pro. Natl. Acad. Sci. USA, 72:1744-1748 (1975).

Ogawa, M., Blood, 81 (11):2844-2853 (1993).

Ogura et al., "Functional and Morphological Differentiation Induction of a Human Megakaryoblastic Leukemia Cell Line (MEG-01s) by Phorbol Diesters", Blood, 72(1):49-60 (1988).

Panelia et al., "Effect of Thimerosal in Leukemia, in Leukemic Cell Lines, and on Normal Hematopoiesis", Cancer Res., 50:4429-4435 (1990).

Quesenberry et al., "The Effect of Interleukin 3 and GM-CSA-2 on Megakaryocyte and Myeloid Clonal Colony Formation", Blood, 65:214 (1985).

Ratner, "Human Immunodeficiency Virus-Associated Autoimmune Thrombocytopenic Purpura: A Review", Am. J. Med., 86:194-198 (1989).

Rennick et al., "Interleukin-6 Interacts With Interleukin-4 and Other Hematpoietic Growth Factors to Selectively Enhance the Growth of Megakaryocytic, Erythroid, Myeloid, and Multipotential Progenitor Cells", Blood, 73(7):1828-1835 (1989).

Sato et al., "Establishment of a Human Leukaemic Cell Line (CMK) with Megakaryocytic Characteristics From a Down's Syndrome Patient with Acute Megakaryoblastic Leukemia", Brit. J. Haematol., 72:184-190 (1989).

Schafner, "Thrombocytopenia and Disorders of Platelet Function", Internal Medicine, 3rd Ed., John J. Hutton et al., Eds. Little Brown and Co. Boston (1990).

Schreiner et al., "Detection of Thrombopoietic Activity in Plasma by Stimulation of Suppressed Thrombopoiesis", J. Clin. Invest., 49:1709-1713 (1970).

Sheiner et al., "Plasma Thrombopoietic Activity in Humans With Normal and Abnormal Platelet Counts", Blood, 56:183-188 (1980).

Sparrow et al., "Megakaryocyte Colony Stimulating Factor: Its Identity to Interleukin-3", Prog. Clin. Biol. Res., 215:123 (1986).

Specter, "In vivo Transfer of a Thrombopoietic Factor", Proc. Soc. Exp. Biol., 108:146-149 (1961).

Straneva et al., "Effects of Thrombocytopoiesis-Stimulating Factor on Terminal Cytoplasmic Maturation of Human Megakaryocytes", Exp. Hematol., 17:1122-1127 (1989).

Tanikawa et al., "Effects of Recombinant Granulocyte Colony- stimulating Factor (rG-CSF) and Recombinant Granulocyte-Macrophage Colony-stimulating Factor (rGM-CSF) on Acute Radiation Hematopoietic Injury in Mice", Exp. Hematol., 17:883-888 (1989).

Trimble et al., "A Megakaryocytic Thrombocytopenia of 4 Years Duration: Successful Treatment With Antithymocyte Globulin", Am. J. Hematol., 37:126-127 (1991).

Tsukada et al., "Synergism Between Serum Factor(s) and Erythropoietin in Inducing Murine Megakaryocyte Colony Formation: The Synergistic Factor in Serum is Distinct from Interleukin–11 and Stem Cell Factor (c–kit ligand)", *Blood*, 81:866–867 (1993).

Vainchenker et al., "Megakaryocyte Colony Formation From Human Bone Marrow Precursors", *Blood*, 54:940 (1979).

Walsh et al., "On the Mechanism of Thrombocytopenic Purpura in Sexually Active Homosexual Men", *N. Eng. J. Med.*, 311:635–639 (1984).

Warren et al., "Synergism Among Interleukin 1, Interleukin 3, and Interleukin 5 in the Production of Eosinophils from Primitive Hemopoietic Stem Cells", *J. Immunol.* 140(1):94–99 (1988).

Williams et al., "Multiple Levels of Regulation of Megakaryocytopoiesis", *Blood Cells*, 15:123–133 (1989).

Williams et al., "The Role of Erythropoietin, Thrombopoietic Stimulating Factor, and Myeloid Colony–stimulating Factors on Murine Megakaryocyte Colony Formation", *Exp. Hematol.*, 12:734 (1984).

Yonemura et al., "Effect of Recombinant Human Interleukin–11 on Rat Megakaryopoiesis and Thrombopoiesis In Vivo: Comparative Study with Interleukin–6", *British Journal of Hematology*, 84:16–23 (1993).

Yonemura et al., "Synergistic Effects of Interleukin 3 and Interleukin 11 on Murine Megakaryopoiesis in Serum–free Culture", *Exp. Hematol.*, 20:1011–1016 (1992).

Carter, C.D. et al., "Thrombopoietin from human embryonic kidney cells stimulates an increase in megakaryocyte size of sublethally irradiated mice," *Radiat.Res.* 135:32–39, 1993.

Cazzola, M., "The end of a long search: at last thrombopoietin [editorial]", *Haematologica* 79:397–399, 1994.

Delgado et al., "The Uses and Properties of PEG–Linked Proteins", *Crit. Rev. Therapeutic Drug Carrier Systems*, 9:249–304 (1992).

Dessypris et al., "Thrombopoiesis–stimulating Factor: Its Effects on Megakaryocyte Colony Formation in vitro and Its Relation to Human Granulocyte–Macrophage Colony–stimulating Factor", *Exp. Hematol.* 18:754–757 (1990).

Doi et al., "Structure of the Rat Platelet Factor 4 Gene: a Marker for Megakaryocyte Differentiation", *Mol. Cell Biol.*, 7:898–904 (1987).

Hegyi et al., "Regulation of Human Megakaryocytopoiesis: Analysis of Proliferation, Ploidy and Maturation in Liquid Cultures", *Intl. J of Cell Cloning*, 8:236–244 (1990).

Hokland, P. [Explosion of our knowledge about thrombopoietin]. *Ugeskr.Laeger.* 156:5535–5536, 1994.

Kaushansky, K., "The mpl ligand: molecular and cellular biology of the critical regulator of megakaryocyte development," *Stem Cells (Dayt).* 12 Suppl 1:91–96, 1994.

McDonald et al., "Monoclonal Antibodies to Human Urinary Thrombopoietin", *Proc. Soc. Exp. Biol. Med.*, 182:151–158 (1986).

Nakeff and Roozendaal, "Thrombopoietin Activity in Mice Following Immune–Induced Thrombocytopenia", *Acta haemat.* 54:340–344 (1975).

Peterfy, M. [Thrombopoietin: a hematopoietic hormone of vital importance, first described in Hungary, synthetized abroad after 36 years (editorial)]. *Orv.Hetil.* 135:2747, 1994.

Poncz, et al., Cloning and Characterization of Platelet Factor 4 cDNA Derived From a Human Erythroleukemic Cell Line, *Blood,* 69:219–223 (1987).

Rak et al., "Study of Thrombopoietin in a Thrombocytopenic Patient", *Med. Exp.*, 1:10–132 (1959).

Rao and Holmsen, "Congenital Disorders of Platelet Function", *Sem. Hematol.*, 23:102–118 (1986).

Wada et al., "Characterization of the Truncated Thrombopoietin Variants", *Biochem. Biophys. Res. Comm.*, 213:1091–1098 (1995).

Warren et al., "The Role of Interleukin 6 and Interleukin 1 in Megakaryocyte Development", *Exp. Hematol.*, 17:1095–1099 (1989).

Wicki et al., "Isolation and Characterization of Human Blood Platelet mRNA and Construction of a cDNA Library in –gt11", *Thromb. Haemost.*, 61:448–453 (1989).

von Heijne, G., Nucleic Acids Res. 14:4683–4690 (1986).

Rose et al., Bioconjugate Chemistry 2:151–159 (1991).

Bartley et al., Identification and Cloning of a megakaryocyte growth and development factor that is a ligand for the cytokine receptor Mpl. Cell 77:1117, 1994.

Benit et al., The 'WS motif' common to v–mpl and members of the cytokine receptor superfamily is dispensable for myeloproliferativeleukemia virus pathogenicity. Oncogene 8:787, 1993.

Le Coniat, The human homolog of the myeloproliferative virus maps to chromosone band 1p34, Hum Genet 83:194, 1989.

McDonald, et al., Megakaryocytic and erythrocytic cell lines share a common precursor cell, Exp Hematol 21:1316, 1993.

Vigon, et al., Expression of the c–mpl proto–oncogene in human hematologic malignancies, Blood 82:877, 1993.

Wendling et al., The oncogene V–MPL, a putative truncated cytokine receptor which immortalizes hematopoietic progenitors, Nouv Rev Fr Hematol 33:145, 1991.

Thompson, Thrombopoietin, Lancet 343:1630, 1994.

T.D. Bartley et al. Cell 77:1117, Jul. 1, 1994.

F.J. de Sauvage et al. , Nature 369:533, Jun. 16, 1994.

Purification of Mpl Ligand

SDS-PAGE 14% NONREDUCING

```
1    CAGGGAGCCACGCCAGCCAAGACACCCCGGCCCAGAATGGAGCTGACTGAATTGCTCCTC    59
-21                                           MetGluLeuThrGluLeuLeuLeu  -14

70   GTGGTCATGCTTCTCCTAACTGCAAGGCTAACGCTGTCCAGCCCGGCTCCTCCTGCTTGT   119
-13  ValValMetLeuLeuLeuThrAlaArgLeuThrLeuSerSerProAlaProProAlaCys    7

120  GACTTCCGAGTCCTCAGTAAACTGCTTCGTGACTCCCATGTCCTTCACAGCAGACTGAGC   179
 8   AspLeuArgValLeuSerLysLeuLeuArgAspSerHisValLeuHisSerArgLeuSer   27

180  CAGTGCCCAGAGGTTCACCCTTTGCCTACACCTGTCCTGCTGTGACTTTAGC           239
 28  GlnCysProGluValHisProLeuProThrProValLeuProAlaValAspPheSer      47

240  TTGGGAGAATGGAAAACCCAGATGGAGCTGGAGACATTCTGGGAGCAGTG             299
 48  LeuGlyGluTrpLysThrGlnMetGluLeuAlaGlnAspIleLeuGlyAlaVal         67

300  ACCCTTCTGCTGGAGGAGTGATGGCAGCACGGGACAACTGGGACCCACTGCCTCTCA      359
 68  ThrLeuLeuLeuGluGlyGlyValMetAlaAlaArgGlyGlnLeuGlyProThrCysLeuSer 87

360  TCCCTCCTGGGGCAGCTTTCTGGACAGGTCCGTCCTCCTCCTTGGGGCCCTGCAGAGCCTC 419
 88  SerLeuLeuGlyGlnLeuSerGlyGlnValArgLeuLeuLeuGlyAlaLeuGlnSerLeu  107
```

FIG. IIA

```
420  CTTGGAACCCAGTTCCTCACAGGGCAGGACCAGCTCACAAGGATCCCAATGCCATCC  479
108  LeuGlyThrGlnLeuProProGlnGlyArgThrThrAlaHisLysAspProAsnAlaIle  127

480  TTCCTGAGCTTCCAACACCTGCTCCGAGGAAAGGTGCGTTTCCTGATGCTTGTAGGAGGG  539
128  PheLeuSerPheGlnHisLeuLeuArgGlyLysValArgPheLeuMetLeuValGlyGly  147

540  TCCACCCTCTGCGTCAGGGGCCCCACCACAGCTGTCCCAGCAGAACCTCTA  599
148  SerThrLeuCysValArgArgAlaProThrThrAlaValProSerArgThrSerLeu  167

600  GTCCTCACACTGAACGAGCTCCCAAACAGGACTTCTGGATTGTTGGAGACAAACTTCACT  659
168  ValLeuThrLeuAsnGluLeuProAsnArgThrSerGlyLeuLeuGluThrAsnPheThr  187

660  GCCTCAGCCAGAACTACTGGCTTCTGAAGTGGCAGCAGGGATTCAGAGCCAAG  719
188  AlaSerAlaArgThrThrGlySerGlyLeuLeuLeuLysTrpGlnGlnGlyPheArgAlaLys  207

720  ATTCCTGGTCTGCTGAACCAAACCTCCAGTCCCTGGACCAAATCCCGGATACCTGAAC  779
208  IleProGlyLeuLeuAsnGlnThrSerArgSerLeuAspGlnIleProGlyTyrLeuAsn  227

780  AGGATACACGAACTCTTGAATGGAACTCGTGGACTCTTTCCTGGACCCTCAGCAGGACC  839
228  ArgIleHisGluLeuLeuAsnGlyThrArgGlyLeuPheProGlyProSerArgArgThr  247
```

FIG. 11B

| | | |
|---|---|---|
| 840 | CTAGGAGCCCCGGACATTCCTCAGGAACATCAGACACAGGCTCCCTGCCACCCAACCTC | 899 |
| 248 | LeuGlyAlaProAspIleSerSerGlyThrSerAspThrSerGlyThrSerAspThrSerGlySerLeuProProAsnLeu | 267 |
| 900 | CAGCCTGGATATTCCTCCTTCCCCAACCATCCTCCTACTGGACAGTATACGCTCTTCCCT | 959 |
| 268 | GlnProGlyTyrSerProSerProThrHisProProThrGlyGlnTyrThrLeuPhePro | 287 |
| 960 | CTTCCACCCACCTTGCCCACCCCTGTGGTCCAGCTCCAGTTCCACCCCCTGCTTCCTGACCCTTCT | 1019 |
| 288 | LeuProProThrLeuProThrProValValGlnLeuHisProLeuLeuProAspProSer | 307 |
| 1020 | GCTCCAACGCCCACCCAGCCCCTCTAAACACATCCTACACCCACTCCAGAAT | 1079 |
| 308 | AlaProThrProThrSerProLeuLeuAsnThrSerTyrThrHisSerGlnAsn | 327 |
| 1080 | CTGTCTCAGGAAGGGTAAGGTTCTCAGACACTGCCGACATCAGCATTGTCTCGTGTACAG | 1139 |
| 32 | LeuSerGlnGluGlyEnd | |
| 1140 | CTCCCTTCCCTGCCAGGGCGCCCAGGGCCTGGAGACAACTGGACAAGATTCCTACTTTCCTG | 1199 |
| 1200 | AAACCCAAAGCCCTGGTAAAAGGGATACACAGGACTGAAAAGGAATCATTTTCACTGT | 1259 |
| 1260 | ACATTATAAACCTTCAGAAGCTATTTTTTAAGCTATCAGCAATACTCATCAGAGCAGCT | 1319 |
| 1320 | AGCTCTTTGGTCTCTATTTTCTGCA 1342 | |

```
  1  AGGGAGCCACGCCAGCCAGACACCCCGGCCAGAATGGAGCTGACTGAATTGCTCCTCGTG   60
-21                                    MetGluLeuThrGluLeuLeuLeuVal  -13

61  GTCATGCTTCTCCTAACTGCAAGGCTAACGCTGTCCAGCCCGGCTCCTCCTGCTTGTGAC  120
-12  ValMetLeuLeuLeuThrAlaArgLeuThrLeuSerSerProAlaProProAlaCysAsp    8

121  CTCCGAGTCCTCAGTAAACTGCTTCGTGACTCCCATGTCCTTCACAGCAGACTGAGCCAG  180
  9  LeuArgValLeuSerLysLeuLeuArgAspSerHisValLeuHisSerArgLeuSerGln   28

181  TGCCCAGAGGTTCACCCTTTGCCTACACCTGTCCTGCTGCCTGCTGTGGACTTTAGCTTG  240
 29  CysProGluValHisProLeuProThrProValLeuLeuProAlaValAspPheSerLeu   48

241  GGAGAATGGAAAACCCAGATGGAGGAGACCAAGGCACAGGACATTCTGGGAGCAGTGACC  300
 49  GlyGluTrpLysThrGlnMetGluGluThrLysAlaGlnAspIleLeuGlyAlaValThr   68

301  CTTCTGCTGGAGGGAGTGATGGCAGCACGGGGACAACTGGGACCCACTTGCCTCTCATCC  360
 69  LeuLeuLeuGluGlyValMetAlaAlaArgGlyGlnLeuGlyProThrCysLeuSerSer   88

361  CTCCTGGGGCAGCTTTCTGGACAGGTCCGTCTCCTCCTTGGGGCCCTGCAGAGCCTCCTT  420
 89  LeuLeuGlyGlnLeuSerGlyGlnValArgLeuLeuLeuGlyAlaLeuGlnSerLeuLeu  108

421  GGAACCCAGCTTCCTCCACAGGGCAGGACCACAGCTCACAAGGATCCCAATGCCATCTTC  480
109  GlyThrGlnLeuProProGlnGlyArgThrThrAlaHisLysAspProAsnAlaIlePhe  128

481  CTGAGCTTCCAACACCTGCTCCGAGGAAAGGACTTCTGGATTGTTGGAGACAAACTTCAC  540
129  LeuSerPheGlnHisLeuLeuArgGlyLysAspPheTrpIleValGlyAspLysLeuHis  148

541  TGCCTCAGCCAGAACTACTGGCTCTGGGCTTCTGAAGTGGCAGCAGGGATTCAGAGCCAA  600
149  CysLeuSerGlnAsnTyrTrpLeuTrpAlaSerGluValAlaAlaGlyIleGlnSerGln  168

601  GATTCCTGGTCTGCTGAACCAAACCTCCAGGTCCCTGGACCAAATCCCCGGATACCTGAA  660
169  AspSerTrpSerAlaGluProAsnLeuGlnValProGlyProAsnProArgIleProGlu  188

661  CAGGATACACGAACTCTTGAATGGAACTCGTGGACTCTTTCCTGGACCCTCACGCAGGAC  720
189  GlnAspThrArgThrLeuGluTrpAsnSerTrpThrLeuSerTrpThrLeuThrGlnAsp  208

721  CCTAGGAGCCCCGGACATTTCCTCAGGAACATCAGACACAGGCTCCCTGCCACCCAACCT  780
209  ProArgSerProGlyHisPheLeuArgAsnIleArgHisArgLeuProAlaThrGlnPro  228

781  CCAGCCTGGATATTCTCCTTCCCCAACCCATCCTCCTACTGGACAGTATACGCTCTTCCC  840
229  ProAlaTrpIlePheSerPheProAsnProSerSerTyrTrpThrValTyrAlaLeuPro  248
```

FIG. 12B

```
 841 TCTTCCACCCACCTTGCCCACCCCTGTGGTCCAGCTCCACCCCCTGCTTCCTGACCCTTC  900
     SerSerThrHisLeuAlaHisProCysGlyProAlaProProProAlaSerEnd        265

901 TGCTCCAACGCCCACCCCTACCAGCCCTCTTCTAAACACATCCTACACCCACTCCCAGAA   960
 961 TCTGTCTCAGGAAGGGTAAGGTTCTCAGACACTGCCGACATCAGCATTGTCTCGTGTACA  1020
1021 GCTCCCTTCCCTGCAGGGCGCCCCTGGGAGACAACTGGACAAGATTTCCTACTTTCTCCT  1080
1081 GAAACCCAAAGCCCTGGTAAAAGGGATACACAGGACTGAAAAGGGAATCATTTTTCACTG  1140
1141 TACATTATAAACCTTCAGAAGCTA  1164
```

FIG. 13A

```
canine  1 MELTELLLVVMLLLTARLDPCLPAPPACDPRLLNKMLRDSHVLHSRLSQC  50
          |||||||||||||||||.:  ||||||| |:|.|:|||||||||||||||
human   1 MELTELLLVVMLLLTARLTLSSPAPPACDLRVLSKLLRDSHVLHSRLSQC  50

51 PDIYPLSTPVLLPAVDFSLGEWKTQKEQTKAQDVWGAVALLLDGVLAARG 100
          |::.||.||||||||||||||||||.|:|||||::|||.|||:||:||||
       51 PEVHPLPTPVLLPAVDFSLGEWKTQMEETKAQDILGAVTLLLEGVMAARG 100

101 QLGPSCLSSLLGQLSGQVRLLLGALQGLLGTQLPPQGRTTTHKDPNAIFL 150
          ||||.|||||||||||||||||||||:||||||||||||| |||||||||
      101 QLGPTCLSSLLGQLSGQVRLLLGALQSLLGTQLPPQGRTTAHKDPNAIFL 150

151 SFQQLLRGKVRFLLLVAGPTLCAKQSQPTTAVPTNTSLFLTLRKLPNRTS 200
          |||:||||||||||:||:|.|||.:...||||||..|||.|||..|||||
      151 SFQHLLRGKVRFLMLVGGSTLCVRRAPPTTAVPSRTSLVLTLNELPNRTS 200

201 GLLETNSSISARTTGSGLLKRLQGFRAKIPGLLNQTSRSLNQTPGHLSRT 250
          ||||||.||||||||||||||||:||||||||||||||||||||:|.||.|.
      201 GLLETNFTASARTTGSGLLKWQQGFRAKIPGLLNQTSRSLDQIPGYLNRI 250

251 HGPLNGTHGLLPGLSLTALGAPDIPPGTSDMDALPPNLWPRYSPSPIHPP 300
          |: ||||:||:|| | .||||||..||||:.|||||  |||||.|||
      251 HELLNGTRGLFPGPSRRTLGAPDISSGTSDTGSLPPNLQPGYSPSPTHPP 300

301 PGQYTLFSPLPTSPTPQNPLQPPPPDPSA.TANSTSPLLIAAHPHFQNLS 349
          .||||||. || ||| .|:| |||| |:..|||| ....| ||||
      301 TGQYTLFPLPPTLPTPVVQLHPLLPDPSAPTPTPSPLLNTSYTHSQNLS 350

350 QEE 352
          ||:
      351 QEG 353
```

FIG. 13B

```
murine  1 MELTDLLLAAMLLAVARLTLSSPVAPACDPRLLNKLLRDSHLLHSRLSQC  50
          ||||:|||..|||  .|||||||||.:||||  |:|.|||||||:||||||||
human   1 MELTELLLVVMLLLTARLTLSSPAPPACDLRVLSKLLRDSHVLHSRLSQC  50

51 PDVDPLSIPVLLPAVDFSLGEWKTQTEQSKAQDILGAVSLLLEGVMAARG 100
          |:|.||..|||||||||||||||||||  |:.||||||||.|||||||||||
       51 PEVHPLPTPVLLPAVDFSLGEWKTQMEETKAQDILGAVTLLLEGVMAARG 100

101 QLEPSCLSSLLGQLSGQVRLLLGALQGLLGTQLPLQGRTTAHKDPNALFL 150
          ||:|.||||||||||||||||||||:||||||| ||||||||||:||
      101 QLGPTCLSSLLGQLSGQVRLLLGALQSLLGTQLPPQGRTTAHKDPNAIFL 150

151 SLQQLLRGKVRFLLLVEGPTLCVRRTLPTTAVPSSTSQLLTLNKFPNRTS 200
          |:|:||||||||||:||.||||||. ||||||.|| :||||.:|||||
      151 SFQHLLRGKVRFLMLVGGSTLCVRRAPPTTAVPSRTSLVLTLNELPNRTS 200

201 GLLETNFSVTARTAGPGLLSRLQGFRVKITPGQLNQTSRSPVQISGYLNR 250
          ||||||...|||.|.|||.: ||||.|| || |||||| ||.|||||
      201 GLLETNFTASARTTGSGLLKWQQGFRAKI.PGLLNQTSRSLDQIPGYLNR 249

251 THGPVNGTHGLFAGTSLQTLEASDISPGAFNKGSLAFNLQGGLPPSPSLA 300
          .|: :|||:|||:|.| .||:|.|||.|. :.|||: |||.|..|||. :
      250 IHELLNGTRGLFPGPSRRTLGAPDISSGTSDTGSLPPNLQPGYSPSPTHP 299

301 PDGH.TPPPPSPALPTTHGSPPQLHPLFPDPSTTMPNSTAPHPVTMYPHP 349
          |.|: | || .|.||| ...||||:||||.. |..|.|  | |.|.
      300 PTGQYTLFPLPPTLPT...PVVQLHPLLPDPSAPTPTSPLLNTSYTHS 346

350 RNLSQET 356
          .|||||.
      347 QNLSQEG 353
```

FIG. 15
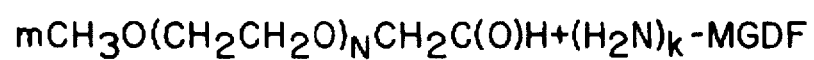
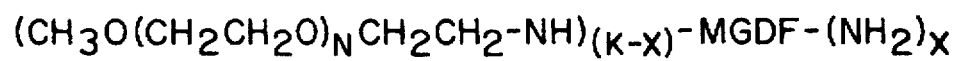

1

MONO-PEGYLATED PROTEINS THAT STIMULATE MEGAKARYOCYTE GROWTH AND DIFFERENTIATION

This application is a continuation-in-part of application Ser. No. 08/252,628, filed May 31, 1994, which is a continuation-in part of application Ser. No. 08/221,768, filed Mar. 31, 1994, abandoned.

FIELD OF THE INVENTION

The present invention relates to novel proteins, referred to herein synonymously as Mpl ligands or MGDFs, that stimulate the growth of megakaryocytes and augment the differentiation or maturation of megakaryocytes, with the ultimate effect of increasing the numbers of platelets. Also provided are processes for obtaining the proteins in homogeneous form from natural sources and producing them by recombinant genetic engineering techniques.

In another aspect, the present invention broadly relates to a novel class of MGDF derivatives wherein an MGDF molecule is attached to a water soluble polymer, and methods for preparing such molecules. In yet another aspect, the present invention relates to MGDF derivatives wherein an MGDF molecule is attached to one or more polyethylene glycol ("PEG") groups, and methods of their preparation.

BACKGROUND OF THE INVENTION

At least two broad areas of research are involved in the present invention. The first relates to the development of megakaryocytes and subsequent production of platelets, and the second relates to a polypeptide member of a growth factor receptor family, referred to herein as the Mpl receptor, and ligands thereof. Each of these areas of research will now be outlined in the following.

A. Platelet Production from Megakaryocytes

Blood platelets are circulating cells that are crucial for the prevention of bleeding and for blood coagulation. Megakaryocytes are the cellular source of platelets and arise from a common bone marrow precursor cell which gives rise to all hematopoietic cell lineages. This common precursor cell is known as the pluripotent stem cell or PPSC.

A hierarchy of megakaryocytic progenitor cells has been defined based on the time of appearance and size of megakaryocyte (MK) colonies appearing in in vitro culture systems in response to appropriate growth factors. The burst-forming unit megakaryocyte (BFU-MK) is the most primitive megakaryocyte progenitor cell. BFU-MK are thought ultimately to produce numerous colony forming unit megakaryocytes (CFU-MK), which are more differentiated MK progenitor cells.

As the MK cells undergo subsequent differentiation, they lose the ability to undergo mitosis but acquire an ability to endoreduplicate. Endoreduplication (or endomitosis) is the phenomenon in cells of nuclear division in the absence of cell division. Endoreduplication ultimately results in an MK which is polyploid. Further MK maturation results in acquisition of cytoplasmic organelles and membrane constituents that characterize platelets.

Platelets are produced from mature MK's by a poorly defined process that has been suggested to be a consequence of MK physical fragmentation, or other mechanisms. Observations of extensive membranous structures within megakaryocytes has led to a model of platelet formation in which a demarcation membrane system outlines nascent platelets within the cell body. Another model of platelet formation has developed from observations that megakaryocytes will form long cytoplasmic processes constricted at platelet-sized intervals from which platelets presumably break off due to blood flow pressures in the marrow and/or in the lung. These cytoplasmic processes were termed proplatelets by Becker and DeBruyn to reflect their presumed precursor role in platelet formation. See Becker and DeBruyn, *Amer. J. Anat.* 145: 183 (1976).

FIG. 1 presents an overview of the various precursor cells involved in megakaryocyte and platelet development. The cell at the far left-hand side of the figure represents a PPSC, and the additional cells to the right of the PPSC in the figure represent BFU-MK, followed by CFU-MK. The cell that is undergoing endoreduplication, which is located immediately to the right of the PPSC in the figure, is a mature megakaryocyte cell. As a result of endomitosis, this cell has become polyploid. The next structure to the right includes long cytoplasmic processes emerging from the polyploid nucleus of the mature megakaryocyte cell. In the far right-hand side of the figure are shown a number of platelets that have been produced by fragmentation of the cytoplasmic processes.

The following is a summary of some prior publications relating to the above description of megakaryocyte maturation and the production of platelets:

1. Williams, N. and Levine, R. F., *British Journal of Haematology* 52: 173–180 (1982).
2. Levin, J., *Molecular Biology and Differentiation of Megakaryocytes*, pub. Wiley-Liss, Inc.: 1–10 (1990).
3. Gewirtz, A. M., *The Biology of Hematopoiesis*, pub. Wiley-Liss, Inc.: 123–132 (1990).
4. Han, Z. C., et al., Int. *J. Hematol.* 54: 3–14 (1991).
5. Nieuwenhuis, H. K. and Sixma, J., *New Eng. J. of Med.* 327: 1812–1813 (1992).
6. Long, M., *Stem Cells* 11: 33–40 (1993).

B. Regulation of Platelet Formation

A large body of data generated in many laboratories indicates that platelet production is regulated by humoral factors. The complexity of this biological process was not originally appreciated and currently it appears that a number of human growth factors possess this capability.

Megakaryocyte regulation occurs at multiple cellular levels. A number of cytokines enhance platelet production by expanding the progenitor cell pool. A second group of humoral growth factors serves as maturation factors acting on more differentiated cells to promote endoreduplication. In addition, there appear to be two independent biofeedback loops regulating these processes.

Several lineage nonspecific hematopoietic growth factors exert important effects on MK maturation. Granulocyte-macrophage colony stimulating factor (GM-CSF), interleukin-3 (IL-3), IL-6, IL-11, leukemia inhibitory factor (LIF), and erythropoietin (EPO) each individually promote human MK maturation in vitro as determined by their effects on MK size, number, or ploidy. The MK maturational effects of LIF, IL-6, and IL-11 are either partially (LIF and IL-6) or totally (IL-11) additive to those of IL-3. Such data from these prior publications suggested that combinations of cytokines may be necessary to promote MK maturation in vivo.

The following is a summary of some prior publications relating to the regulation of megakaryocyte and platelet production:

7. Hoffman, R. et al., *Blood Cells* 13: 75–86 (1987).
8. Murphy, M. J., *Hematology/Oncology Clinics of North America* 3 (3): 465–478 (1988).
9. Hoffman, R., *Blood* 74 (4): 1196–1212 (1989).

10. Mazur, E. M. and Cohen, J. L., *Clin. Pharmacol. Ther.*, 46 (3): 250–256 (1989).

11. Gewirtz, A. M. and Calabretta, B., *Int. J. Cell Cloning* 8: 267–276 (1990).

12. Williams, N., *Progress in Growth Factor Research* 2: 81–95 (1990).

13. Gordon, M. S. and Hoffman, R., *Blood* 80 (2): 302–307 (1992).

14. Hunt, P. et al., *Exp. Hematol.* 21: 372–281 (1993).

15. Hunt, P. et al., *Exp. Hematol.* 21: 1295–1304 (1993).

It has also been reported (see reference 16) that human aplastic serum contains a megakaryocyte colony stimulating activity distinct from IL-3, granulocyte colony stimulating factor, and factors present in lymphocyte-conditioned medium. However, the molecule responsible for this activity was neither isolated nor characterized in the prior art. 16. Mazur, E. M., et al., *Blood* 76: 290–297 (1990).

C. The Mpl Receptor

The myeloproliferative leukemia virus (MPLV) is a murine replication-defective retrovirus that causes acute leukemia in infected mammals. It has been discovered that a gene expressed by MPLV consists of a part of the gene that encodes the retroviral envelope (or external protein coat) of the virus fused to a sequence that is related to the cytokine receptor family, including the receptors for GM-CSF, G-CSF, and EPO.

Expression of the MPLV gene described above has the interesting biological property of causing murine progenitor cells of various types to immediately acquire growth factor independence for both proliferation and terminal maturation. Moreover, some cultures of bone marrow cells acutely transformed by MPLV contained megakaryocytes, suggesting a connection between the MPLV gene and megakaryocyte growth and differentiation.

It is now recognized that the MPLV viral gene (referred to as v-Mpl) has a homolog in mammalian cells, which is referred to as a cellular Mpl gene (or c-Mpl). Using v-Mpl-derived probes, a cDNA corresponding to the human c-Mpl gene was cloned. See PCT published application WO 92/07074 (published Apr. 30, 1992; discussed below). Sequence analysis has shown that the protein encoded by the c-Mpl gene product belongs to the highly conserved cytokine receptor superfamily, just like the homologous v-Mpl gene product.

This cellular gene, c-Mpl, is thought to play a functional role in hematopoiesis based on the observation that its expression was found in bone marrow, spleen, and fetal liver from normal mice by RNAse probe protection and RT-PCR experiments, but not in other tissues. In particular, c-Mpl is expressed on megakaryocytes. It has also been demonstrated that the human cellular gene, human c-Mpl, is expressed in CD34 positive cells, including purified megakaryocytes and platelets. CD34 is an antigen that is indicative of early hematopoietic progenitor cells. Furthermore, exposure of CD34 positive cells to synthetic oligodeoxynucleotides that are anti-sense to the c-Mpl mRNA or message significantly inhibits the colony forming ability of CFU-MK megakaryocyte progenitors, but has no effect on erythroid or granulomacrophage progenitors.

The above data and observations suggest that c-Mpl encodes a cell surface molecule, referred to herein as the Mpl receptor, which binds to a ligand, that activates the receptor, possibly leading to production and/or development of megakaryocytes.

PCT patent publication WO 92/07074 is directed to the sequence of the protein produced by the c-Mpl gene, from both human and murine sources. This gene product, which is thought to be a receptor as explained above, is made up of at least three general regions or domains: an extracellular domain, a transmembrane domain, and an intracellular (or cytoplasmic) domain. Attached together, these domains make up the intact Mpl receptor. This PCT publication also refers to a soluble form of the receptor that substantially corresponds to the extracellular domain of the mature c-Mpl protein. The intracellular domain contains a hydrophobic region that, when attached via the transmembrane region to the extracellular domain of the protein, renders the overall protein subject to aggregation and insolubility. On the other hand, when the extracellular domain of the c-Mpl gene product is separated from the transmembrane domain and the intracellular domain, it becomes soluble, hence the extracellular form of the protein is referred to as a "soluble" form of the receptor.

The following is a summary of some prior publications relating to the above description of the v-Mpl and c-Mpl receptors and genes:

17. Wendling, F., et al., *Leukemia* 3 (7): 475–480 (1989).

18. Wendling, F., et al., *Blood* 73 (5): 1161–1167 (1989).

19. Souyri, M., et al., *Cell* 63: 1137–1147 (1990).

20. Vigon, I., et al., *Proc. Natl. Acad. Sci. USA* 89: 5640–5644 (1992).

21. Skoda, R. C., et al., *The EMBO Journal* 12 (7): 2645–2653 (1993).

22. Ogawa, M., *Blood* 81 (11): 2844–2853 (1993).

23. Methia, N., et al., *Blood* 82 (5): 1395–1401 (1993).

24. Wendling, F, et al., *Blood* 80: 246a (1993).

D. The need for an agent capable of stimulating platelet production

It has been reported recently that platelet transfusions are being administered at an ever increasing rate at medical centers in North America, Western Europe, and Japan. See Gordon, M. S. and Hoffman, R., *Blood* 80 (2): 302–307 (1992). This increase appears to be due in large measure to advances in medical technology and greater access to such technologies as cardiac surgery and bone marrow, heart, and liver transplantation. Dose intensification as a means of delivering therapies to cancer patients and the HIV-1 epidemic have also contributed to the heavy demand on the platelet supply.

Platelet usage carries with it the possibility of transmission of the many blood-born infectious diseases as well as alloimmunization. Moreover, the production of purified platelets is an expensive endeavor and hence the increasing use of such platelets increases overall medical costs. As a result, there exists an acute need for new and improved methods for producing platelets for human uses.

Exemplary prior approaches to enhancing platelet production are described in the following:

U.S. Pat. No. 5,032,396 reports that interleukin-7 (IL-7) is capable of stimulating platelet production. Interleukin-7 is also known as lymphopoietin-1 and is a lymphopoietic growth factor capable of stimulating growth of B- and T-cell progenitors in bone marrow. Published PCT application serial number 88/03747, filed Oct. 19, 1988 and European patent application number 88309977.2, filed Oct. 24, 1988 disclose DNA's, vectors, and related processes for producing mammalian IL-7 proteins by recombinant DNA technology. The data presented in the U.S. patent show that IL-7 can increase circulating platelets in normal and sublethally irradiated mice.

U.S. Pat. No. 5,087,448 discloses that megakaryocytes and platelets can be stimulated to proliferate in mammals by treating them with interleukin-6. Recombinant human interleukin-6 is a 26,000 molecular weight glycoprotein with multiple biological activities. The data presented in this patent show that IL-6 has an effect of increasing colonies of megakaryocytes in vitro.

None of the above-cited patents mentions anything with respect to the Mpl ligands that are involved in the present invention.

In spite of the above disclosures, there remains a strong need for new stimulators of megakaryocytes and/or platelets in mammals.

E. Background relating to Chemically Modified MGDF

Proteins for therapeutic use are currently available in suitable forms in adequate quantities largely as a result of the advances in recombinant DNA technologies. Chemical derivatives of such proteins may effectively block a proteolytic enzyme from physical contact with the protein backbone itself, and thus prevent degradation. Additional advantages may include, under certain circumstances, increasing the stability and circulation time of the therapeutic protein and decreasing immunogenicity. However, it should be noted that the effect of modification of a particular protein cannot be predicted. A review article describing protein modification and fusion proteins is Francis, *Focus on Growth Factors* 3: 4–10 (May 1992) (published by Mediscript, Mountview Court, Friern Barnet Lane, London N20, OLD, UK).

Polyethylene glycol ("PEG" or "peg") is one such chemical moiety which has been used in the preparation of therapeutic protein products. For example Adagen®, a formulation of pegylated adenosine deaminase is approved for treating severe combined immunodeficiency disease; pegylated superoxide dismutase has been in clinical trials for treating head injury; pegylated alpha interferon has teen tested in phase I clinical trials for treating hepatitis; pegylated glucocerebrosidase and pegylated hemoglobin are reported to have been in preclinical testing. For some proteins, the attachment of polyethylene glycol has been shown to protect against proteolysis, Sada, et al., J. Fermentation Bioengineering 71: 137–139 (1991), and methods for attachment of certain polyethylene glycol moieties are available. See U.S. Pat. No. 4,179,337, Davis et al., "Non-Immunogenic Polypeptides," issued Dec. 18, 1979; and U.S. Pat. No. 4,002,531, Royer, "Modifying enzymes with Polyethylene Glycol and Product Produced Thereby," issued Jan. 11, 1977. For a review, see Abuchowski et al., in Enzymes as Drugs. (J. S. Holcerberg and J. Roberts, eds. pp. 367–383 (1981)).

Other water soluble polymers have been used to modify proteins, such as copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, and poly amino acids (either homopolymers or random copolymers).

For polyethylene glycol, a variety of means have been used to attach the polyethylene glycol molecules to the protein. Generally, polyethylene glycol molecules are connected to the protein via a reactive group found on the protein. Amino groups, such as those on lysine residues or at the N-terminus, are convenient for such attachment. For example, Royer (U.S. Pat. No. 4,002,531, above) states that reductive alkylation was used for attachment of polyethylene glycol molecules to an enzyme. EP 0 539 167, published Apr. 28, 1993, Wright, "Peg Imidates and Protein Derivates Thereof" states that peptides and organic compounds with free amino group(s) are modified with an imidate derivative of PEG or related water-soluble organic polymers. U.S. Pat. No. 4,904,584, Shaw, issued Feb. 27, 1990, relates to the modification of the number of lysine residues in proteins for the attachment of polyethylene glycol molecules via reactive amine groups.

One specific therapeutic protein which has been chemically modified is granulocyte colony stimulating factor, "G-CSF." See European patent publications EP 0 401 384, EP 0 473, 268, and EP 0 335 423.

Another example is pegylated IL-6, EP 0 442 724, entitled, "Modified hIL-6," (see co-pending U.S. Ser. No. 07/632,070) which discloses polyethylene glycol molecules added to IL-6. EP 0 154 316, published Sep. 11, 1985, reports reacting a lymphokine with an aldehyde of polyethylene glycol.

The ability to modify MGDF is unknown in the art since the susceptibility of each individual protein to modification is determined by the specific structural parameters of that protein. Moreover, the effect of such a modification on the biological properties of each protein is unpredictable from the art. Because of the many clinical applications of MGDF, as set forth herein, a derivatized MGDF product with altered properties is desirable. Such molecules may have increased half-life and/or activity in vivo, as well other properties.

Pegylation of protein molecules will generally result in a mixture of chemically modified protein molecules. As an illustration, protein molecules with five lysine residues and a free amino group at the N-terminus reacted in the above methods may result in a heterogeneous mixture, some having six polyethylene glycol moieties, some five, some four, some three, some two, some one and some zero. And, among the molecules with several, the polyethylene glycol moieties may not be attached at the same location on different molecules. It will frequently be desirable to obtain a homogeneous product that contains substantially all one or a small number (e.g., 2–3) of modified protein species that vary in the number and/or location of chemical moieties, such as PEG. Nevertheless, mixtures of, e.g., mono-, di- and/or tri-pegylated species may be desirable or tolerable for a given therapeutic indication.

Variability of the mixture from lot to lot would be disadvantageous when developing a therapeutic pegylated protein product. In such development, predictability of biological activity is important. For example, it has been shown that in the case of nonselective conjugation of superoxide dismutase with polyethylene glycol, several fractions of the modified enzyme were completely inactive (P. McGoff et al. Chem. Pharm. Bull. 36: 3079–3091 (1988)). See also, Rose et al., Bioconjugate Chemistry 2: 154–159 (1991) which reports the selective attachment of the linker group carbohydrazide to the C-terminal carboxyl group of a protein substrate (insulin). One cannot have such predictability if the therapeutic protein differs in composition from lot to lot. Some of the polyethylene glycol moieties may not be bound as stably in some locations as others, and this may result in such moieties becoming dissociated from the protein. Of course, if such moieties are randomly attached and therefore become randomly dissociated, the pharmacokinetics of the therapeutic protein cannot be precisely predictable.

Also highly desirable is a derivatized MGDF product wherein there is no linking moiety between the polymer moiety and the MGDF moiety. One problem with the above methods is that they typically require a linking moiety between the protein and the polyethylene glycol molecule. These linking moieties may be antigenic, which is also disadvantageous when developing a therapeutic protein.

A method involving no linking group is described in Francis et al., In: "Stability of protein pharmaceuticals: in vivo pathways of degradation and strategies for protein stabilization" (Eds. Ahern., T. and Manning. M. C.) Plenum, N.Y., 1991) Also, Delgado et al. "Coupling of PEG to Protein By Activation with Tresyl Chloride, Applications In Immunoaffinity Cell Preparation". In: Fisher et al., ed., Separations Using Aqueous Phase Systems, Applications In Cell Biology and Biotechnology. Plenum Press, N.Y., N.Y. 1989 pp. 211–213 involves the use of tresyl chloride, which results in no linkage group between the polyethylene glycol moiety and the protein moiety. This method may be difficult to use to produce therapeutic products as the use of tresyl chloride may produce toxic by-products.

Chamow et al., Bioconjugate Chem. 5: 133–140 (1994) report the modification of CD4 immunoadhesin with monomethoxy-polyethylene glycol ("MePEG glycol") aldehyde via reductive alkylation. The authors report that 50% of the CD4-Ig was mePEG-modified by selective reaction at the α-amino group of the N-terminus. Id. at page 137. The authors also report that the in vitro binding capability of the modified CD4-Ig (to the protein gp 120) decreased at a rate correlated to the extent of MePEGylation. Ibid.

Thus, there is a need for MGDF derivatives, and, more particularly, a need for pegylated MGDF. There also exists a need for methods to carry out such derivatization.

SUMMARY OF THE INVENTION

In one aspect, the present invention provides novel polypeptides that specifically promote megakaryocyte growth and/or development ("Mpl ligands" or "MGDFs") which are substantially free from (i.e., isolated from) other proteins (i.e., mammalian proteins in the case of an Mpl ligand obtained from a mammalian source). Such proteins may be purified from cell sources producing the factors naturally or upon induction with other factors. They may also be produced by recombinant genetic engineering techniques. Mpl ligands may further be synthesized by chemical techniques, or a combination of the above-listed techniques.

The Mpl ligands of this invention are obtainable in their native form from mammalian sources. Two exemplary Mpl ligands isolated from canine aplastic plasma are described in the examples section herein. However, it is demonstrated in other examples herein that closely related Mpl ligands are present in aplastic plasma from both human and porcine sources. Notably, the activity of each of the human, porcine, and canine Mpl ligands is specifically inhibitable by the soluble form of the murine Mpl receptor, demonstrating that all of these Mpl ligands (as well as those from other mammalian sources, including murine) are closely related both on structural and activity levels.

It is expected that human, porcine, and other mammalian Mpl ligands, may be isolated from natural sources by procedures substantially as detailed herein. See Example 10. Accordingly, this invention generally encompasses mammalian Mpl ligands, such as from dogs, pigs, humans, mice, horses, sheep, and rabbits. Particularly preferred Mpl ligands are those from dogs, pigs and humans.

In addition, genes encoding human Mpl ligands have been cloned from a human fetal kidney and liver libraries and sequenced, as set forth in the Example section below. Two human polypeptide sequences have been determined to have activity in a cell-based assay (see Example 4). These sequences differ in their length, but have identity over a large stretch of their amino acid sequences. The identical portions have homology to erythropoietin. The Mpl ligands are also referred to herein as Megakaryocyte Growth and Development Factors (MGDFs); all general references to Mpl ligands shall apply to those referred to herein as MGDFs and vice versa. By "MGDF polypeptide" is meant a polypeptide that has an activity to specifically stimulate or inhibit the growth and/or development of megakaryocytes. Exemplary such polypeptides are disclosed herein.

The Mpl ligands of the present invention have been found to be specifically active in the megakaryocyte lineage, augmenting maturation and/or proliferation of megakaryocytes, as demonstrated in the assays of Examples 2 and 4 below. By "specifically" is meant that the polypeptides exhibit biological activity to a relatively greater degree towards megakaryocytes as compared to many other cell types. Those that are stimulatory towards megakaryocytes are expected to have an in vivo activity of stimulating the production of platelets, through the stimulation of maturation and differentiation of megakaryocytes.

Two preferred Mpl ligands from a canine source have apparent molecular weights of approximately 25 kd and 31 kd as determined by sodium dodecyl sulfate polyacrylamide gel electrophoresis (SDS-PAGE) under non-reducing conditions. Both proteins are purified during the same purification protocol which is detailed in the examples section below.

Two preferred human ligands, MGDF-1 (amino acids 1-332 of SEQ ID NO: 25) and MGDF-2, (amino acids 1-174 of SEQ ID NO: 25) are 332 and 174 amino acids in length, respectively, not including a 21 amino acid putative signal peptide. These sequences, and a third related molecule, MGDF-3 (amino acids 1-265 of SEQ ID NO: 27) are shown in FIGS. 11 and 12.

Still a further aspect of the present invention are processes for isolating and purifying the Mpl ligands of the present invention or fragments thereof from mammalian sources, preferably whole blood, serum or plasma. Aplastic blood, serum or plasma are especially preferred starting materials. Aplastic blood, serum or plasma may be obtained by a process involving irradiating a mammal with a radiation source such as cobalt-60 at a radiation level of about 400–800 rads so as to render them aplastic. Such a procedure is known in the art, as exemplified in the publications cited in Example 1 below. In the case of humans, irradiated blood, plasma, or serum may be obtained from a patient after radiation therapy, e.g., to treat cancer.

Thereafter, the aplastic blood, serum or plasma is subjected to a purification process. The purification process provided by the present invention comprises the following key procedures: lectin affinity chromatography and Mpl receptor affinity chromatography. Each of these procedures results in an approximately 300–500-fold purification of the 25 and 31 kd proteins from canine aplastic plasma. Other standard protein purification procedures may be included with the above procedures to further purify the Mpl ligands of the present invention, such as those procedures detailed below.

Another aspect of the present invention includes polynucleotides that encode the expression of a mammalian Mpl ligand protein. Such DNA sequences may include an isolated DNA sequence that encodes the expression of mammalian Mpl ligand proteins as described herein. The DNA sequences may also include 5' and 3' mammalian non-coding sequences flanking the Mpl ligand coding sequence. The DNA sequences may further encode an amino terminal signal peptide.

Also provided by the present invention are recombinant DNA molecules, each comprising vector DNA and a DNA sequence encoding a mammalian Mpl ligand. The DNA molecules provide the Mpl ligand DNA in operative association with a regulatory sequence capable of directing the replication and expression of Mpl ligand in a selected host cell. Host cells (e.g., bacterial, mammalian insect, yeast, or plant cells) transformed with such DNA molecules for use in expressing a recombinant Mpl ligand protein are also provided by the present invention.

The DNA molecules and transformed cells of the invention are employed in another aspect, a novel process for producing recombinant mammalian Mpl ligand protein, or peptide fragments thereof. In this process a cell line transformed with a DNA sequence encoding expression of Mpl ligand protein or a fragment thereof (or a recombinant DNA molecule as described above) in operative association with a suitable regulatory or expression control sequence capable of controlling expression of the protein is cultured under appropriate conditions permitting expression of the recombinant DNA. This claimed process may employ a number of known cells as host cells for expression of the protein. Presently preferred cell lines for producing Mpl ligand are mammalian cell lines (e.g., CHO cells) and bacterial cells (e.g., E. coli).

The expressed Mpl ligand protein is then harvested from the host cell, cell lysate or culture medium by suitable conventional means. The conditioned medium may be processed through the same purification steps or modifications thereof as used to isolate the Mpl ligand from aplastic plasma. (See Example 7).

In a still further aspect of the present invention, there are provided recombinant Mpl ligand proteins. These proteins are substantially free from other mammalian materials, especially proteins. The Mpl ligand proteins of this invention are also characterized by containing one or more of the physical, biochemical, pharmacological or biological activities described herein.

The present invention also relates to chemically modified MGDF comprised of a MGDF protein moiety connected to at least one water soluble polymer, and methods for the preparation and use of such compositions. In particular, the present invention includes chemically modified MGDF wherein the MGDF species is reacted with reactive polyethylene glycol molecules so as to attach PEG to MGDF. Such attachment may be accomplished by pegylation reactions discussed herein, such as acylation or alkylation. Acylation or alkylation with PEG may be carried out under conditions whereby the major product is monopegylated or polypegylated. Polypegylation generally involves attachment of PEG to the ε-amino groups of lysine residues and may additionally involve pegylation at the N-terminus of the polypeptide. Monopegylation preferably involves attachment of PEG to the α-amino group at the N-terminus of the protein. The yield and homogeneity of such monopegylation reaction may be enhanced via a type of reductive alkylation which selectively modifies the α-amino group of the N-terminal residue of an MGDF protein moiety, thereby providing for selective attachment of a water soluble polymer moiety at the N-terminus of the protein. This provides for a substantially homogeneous preparation of polymer/MGDF protein conjugate molecules as well as (if polyethylene glycol is used) a preparation of pegylated MGDF protein molecules having the polyethylene glycol moiety directly coupled to the protein moiety.

Another aspect of this invention provides pharmaceutical compositions containing a therapeutically effective amount of isolated naturally-occurring or recombinant Mpl ligand, which may be derivatized with a water soluble polymer such as polyethylene glycol, along with a pharmaceutically acceptable carrier, diluent, or excipient. These pharmaceutical compositions may be employed in methods for treating disease states or disorders characterized by a deficiency of megakaryocytes and/or platelets as well as an in vivo deficiency of the Mpl ligand. They may also be employed prophylactically to ameliorate expected megakaryocyte or platelet deficiencies (e.g., due to surgery).

Thus, the Mpl ligands of the present invention may be employed in the treatment of aplastic anemias, e.g., to augment production of platelets in patients having impaired platelet production (such as AIDS patients or patients undergoing cancer chemotherapy). Mpl ligand may be used to treat blood disorders such as thrombocytopenia. Mpl ligand may be used as an adjunctive therapy for bone marrow transplant patients. Such patients could be human or another mammal. Mpl ligand from one species is also expected to be useful in another species.

A further aspect of the invention, therefore, is a method for treating these and other pathological states resulting from a deficiency of platelets by administering to a patient a therapeutically effective amount of a pharmaceutical composition as described above. These therapeutic methods may include administration, simultaneously or sequentially with Mpl ligand, an effective amount of at least one other megakaryocyte colony stimulating factor, a cytokine (e.g., EPO), a soluble Mpl receptor, hematopoietin, interleukin, growth factor, or antibody.

Still another aspect of the present invention provides antibodies (e.g., polyclonal, monoclonal, humanized, and recombinant), and antibody fragments, directed against (i.e., reactive with) a mammalian Mpl ligand or a ligand fragment. As part of this aspect, therefore, the invention includes cells capable of secreting such antibodies (e.g., hybridomas in the case of monoclonal antibodies) and methods for their production and use in diagnostic or therapeutic procedures.

Another aspect of the invention is an assay of a body fluid for the presence of Mpl ligand. Such an assay could employ antibodies that specifically recognize an Mpl ligand, in a single antibody or "sandwich" format. Such an assay could be used to determine whether a patient needs external administration of Mpl ligand and/or whether such patient is likely to experience a platelet deficiency or disorder. Such assays could be included in a kit format, including positive and negative controls, antibody(ies), and other standard kit components.

Other aspects and advantages of the present invention will be apparent upon consideration of the following detailed description of preferred embodiments thereof.

BRIEF DESCRIPTION OF THE FIGURES

Numerous features and advantages of the present invention will become apparent upon review of the figures, wherein:

FIG. 11 shows the cDNA and deduced amino acid sequences of human MGDF-1 (amino acids 1-332 of SEQ ID NO: 25) and MGDF-2 (amino acids 1-174 of SEQ ID NO: 25).

FIG. 12 shows the cDNA and deduced amino acid sequences of human MGDF-3 (amino acids 1-265 of SEQ ID NO: 27).

FIG. 13A shows a comparison between MGDF- 1 (amino acids 1-332 of SEQ ID NO: 25) with a signal peptide attached to the N-terminus and MGDF from a canine source also having a signal peptide attached to the N-terminus.

FIG. 13B shows a comparison between MGDF-1 (amino acids 1-332 of SEQ ID NO: 25) and MGDF with a signal peptide attached to the N-terminus from a murine source also having a signal peptide attached to the N-terminus.

FIG. 15 shows an example of nonspecific MGDF reductive alkylation using mono-methoxy-polyethylene glycol aldehydes to result in a poly-pegylated product.

DETAILED DESCRIPTION OF THE INVENTION

Figure 1:
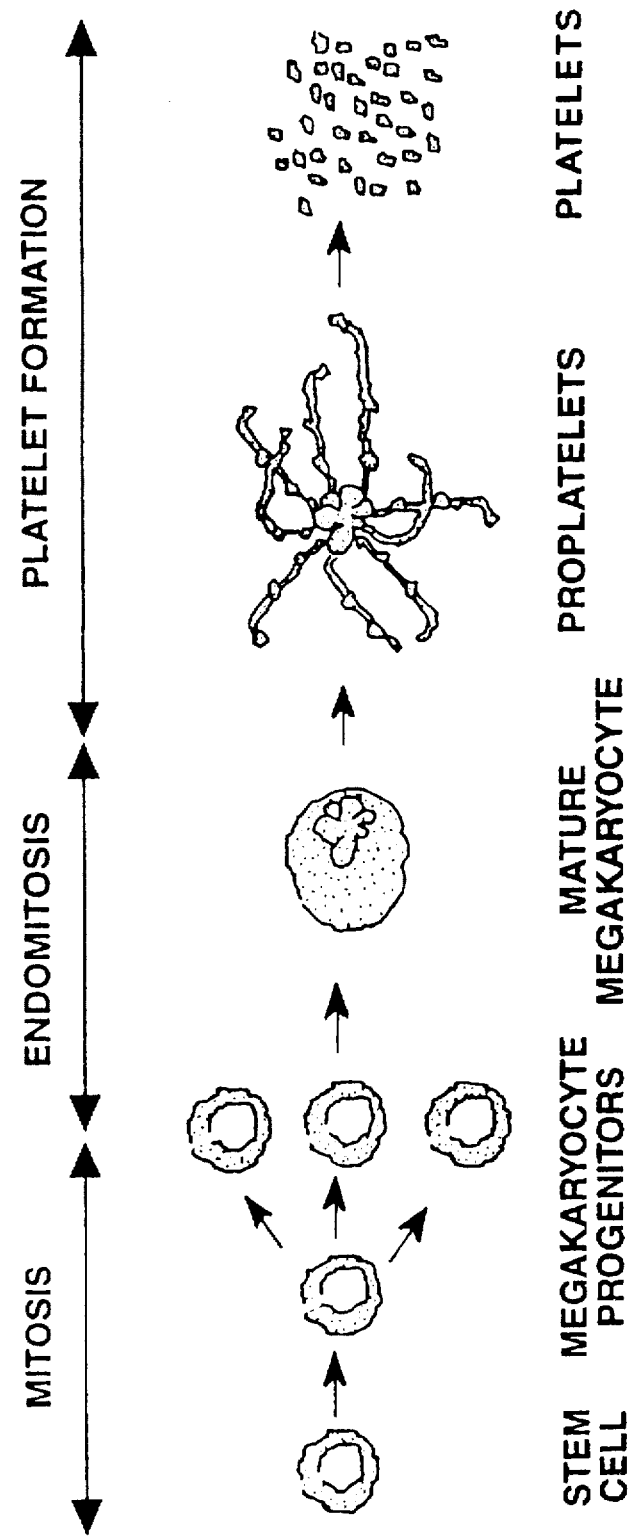
FIG. 1 depicts an overview of development and maturation of megakaryocytes and platelets.

Additional aspects and advantages of the invention will be apparent to those skilled in the art upon consideration of the following description, which details the practice of the invention.

The novel mammalian megakaryocyte growth promoting, and/or platelet producing factors, referred to as Mpl ligands, provided by the present invention are homogeneous proteins substantially free of association with other mammalian proteinaceous materials. Preferably, the proteins are about 90% free of other proteins, particularly preferably, about 95% free of other proteins, and most preferably about ≧98% free of other proteins. These proteins can be produced via recombinant techniques to enable large quantity production of pure, active Mpl ligand useful for therapeutic applications. Alternatively such proteins may be obtained in a homogeneous form from mammalian aplastic blood, plasma or serum, or from a mammalian cell line secreting or expressing an Mpl ligand. Further, Mpl ligand or active fragments thereof may be chemically synthesized.

In general, by "Mpl ligands" as used in connection with the present invention is meant the Mpl ligands disclosed herein as well as active fragments and variants thereof, which are described in greater detail below.

Two preferred Mpl ligands from a canine source have apparent molecular weights of approximately 25 kd and 31 kd as determined by sodium dodecyl sulfate polyacrylamide gel electrophoresis (SDS-PAGE) under non-reducing conditions. Both proteins are purified during the same purification protocol which is detailed in the examples section below. Thus, for example, both of these Mpl ligands bind wheat germ lectin and immobilized Mpl receptor. The 25 kd form includes an amino acid sequence as follows:

Ala-Pro-Pro-Ala-Xaa-Asp-Pro-Arg-Leu-Leu-Asn-Lys-Met-Leu-Arg-Asp-Ser-His-Val-Leu-His-Xaa-Arg-Leu-Xaa-Gln-Xaa-Pro-Asp-Ile-Tyr (SEQ ID NO: 1).

The 31 kd form includes an amino acid sequence as follows:

Ala-Pro-Pro-Ala-Xaa-Asp-Pro-Arg-Leu-Leu-Asn-Lys-Met-Leu-Arg-Asp-Ser-His-Val-Leu-His (SEQ ID NO: 2).

The "Xaa" amino acids shown in SEQ ID NOS: 1 and 2 are not known with certainty, but are expected to be cysteine, serine, threonine, or (less likely) tryptophan.

It can be seen from the above sequences that the 31 kd ligand comprises at least a portion of the 25 kd form. In particular, the first 21 amino acids of the 31 kd protein are exactly the same as those of the 25 kd protein. This evidence, and especially the fact that both proteins have activity in the Mpl ligand activity assays presented herein, leads to the conclusion that both proteins are very closely related in terms of structure and activity. It is likely that the 31 kd form of the protein differs form the 25 kd form in differential C-terminal sequence, differential glycosylation and/or differential splicing of the gene encoding the proteins.

In addition to the above sequence information, another sequence was determined during sequencing of the 25 kd band prior to the final purification step (using reverse phase HPLC). This sequence was found associated with the 25 kd band under non-reducing conditions but not reducing conditions, implying that it is the result of cleavage into two portions (e.g., by a protease) of the 25 kd protein, which portions are held together by a disulfide bond. This sequence is:

Thr-Gln-Lys-Glu-Gln-Thr-Lys-Ala-Gln-Asp-Val-Leu-Gly-Ala-Val-Ala-Leu (SEQ ID NO: 3)

Although the precise location of SEQ ID NO: 3 in the sequence of the 25 kd protein is unclear, analogy with other cytokines, such as erythropoietin, supports the possibility that the sequence occurs around amino acid number 114 in the 25 kd protein. It should be noted that it is likely, although unproven, that SEQ ID NO: 3 also occurs in the 31 kd protein, probably again starting around amino acid number 114. This sequence information is discussed in additional detail in Example 7.

Since the initial purification experiments of the canine ligands, summarized above, a gene encoding a canine ligand has now been cloned. As a result, the full length amino acid sequence of this canine ligand has been determined to be that set forth in FIG. 13A. Based on molecular weight calculations, it is predicted that the 25 kd and 31 kd canine ligands are C-terminal processed forms of the full-length ligand shown in FIG. 13A. Additionally, a murine Mpl ligand has been obtained having the sequence set forth in FIG. 3B.

Such purified ligands may also be characterized by specific activity in the human megakaryocyte assay of Example 2 of at least about $5.7 \times 10^9$ megakaryocyte units/mg. A megakaryocyte unit is defined as that amount of material that results in the production of as many megakaryocytes as 1 microliter of APK9 standard control using the assay described in Example 2.

Such purified ligands are also characterized by a specific activity in the Mpl-dependent cell growth assay of Example 4 of at least about $6.9 \times 10^9$ cell growth units/mg. A "cell growth unit" is defined as the amount of ligand required to result in the growth of 200 1A6.1 cells in the assay of Example 4.

The following Table 1 shows additional specific calculations of activity for actual purified canine Mpl ligands prepared in accordance with this invention:

TABLE 1

| Mpl Ligand | 1A6.1 assay (units/mg) | Human Meg assay (units/mg) |
| --- | --- | --- |
| 31 kd | $6.52 \times 10^9$ | $5.7 \times 10^9$ |
| 25 kd | $10.5 \times 10^9$ | $14 \times 10^9$ |

Summarizing the above information, some exemplary Mpl ligands of the present invention are characterized by one or more of the following biochemical and biological properties:

(a) such Mpl ligands are isolated from canine aplastic plasma;

(b) such Mpl ligands have apparent molecular weights of approximately 25 kd or 31 kd as determined by 12–14% sodium dodecyl sulfate polyacrylamide gel electrophoresis (SDS-PAGE) under non-reducing conditions;

(c) the Mpl ligands comprise the following amino acid sequences:

SEQ ID NO: 1, in the case of the 25 kd protein; or

SEQ ID NO: 2, in the case of the 31 kd protein;

(d) the Mpl ligands additionally comprise the amino acid sequence SEQ ID NO: 3 (particularly preferably in the 25 kd protein);

(e) the Mpl ligands bind to wheat germ lectin;

(f) the Mpl ligands bind to immobilized soluble murine Mpl receptor;

(g) the Mpl ligand activity can be inhibited in vitro by soluble Mpl receptor; and (h) the Mpl ligands bind to an anion exchange column at a pH of about 8–9.

The biological activities of preferred Mpl ligands of the present invention are demonstrated by their ability to specifically stimulate the growth and development of megakaryocytes in the megakaryocyte growth promoting assay of Example 2. In this assay, MPL ligand stimulates the differentiation of human peripheral blood CD34$^+$ (i.e., CD-34 cells selected by immunoadsorption) cells during an 8 day culture period. Megakaryocytes are identified by staining with specific anti-platelet antigen antibodies and counted microscopically. MPL ligand also stimulates the growth of the factor-dependent cell line, 1A6.1. In the absence of MPL ligand, the cells will die. 1A6.1 cell number is assessed after 2 days in culture with MPL ligand.

The Mpl ligands described above have specific activities as described in Table 1 above.

Sources of the Mpl ligands have been determined to be aplastic mammalian blood, plasma, or serum. However, the source of such ligands is not expected to be limited to such known sources and may include other mammalian body fluids, cells obtained therefrom, etc.

The purification of native Mpl ligands from mammalian sources is based on two key purification steps:

(a) lectin affinity chromatography, preferably using wheat germ agglutinin; and (b) immobilized Mpl receptor affinity chromatography.

Additional steps may be included to further purify the protein, such as ion exchange chromatography, gel filtration chromatography, and reverse phase chromatography.

The purification techniques actually employed in obtaining Mpl ligand from canine aplastic plasma comprise the following steps (See, Example 7).

(a) lectin affinity chromatography (wheat germ agglutinin chromatography is especially preferred);

(b) soluble Mpl receptor (Mpl-X) affinity chromatography (preferably, using immobilized murine Mpl-X);

(c) ion (anion or cation) exchange chromatography (preferably, anion exchange chromatography; particularly preferably using a Mono Q column);

(d) gel filtration chromatography under dissociative conditions (preferably, using Superdex 200 plus SDS); and (e) reverse phase chromatography (preferably, using a C-4 column).

Homogeneous mammalian Mpl ligand, including the human ligand, may be obtained by applying the above purification procedures to aplastic blood, serum, or plasma or other sources of mammalian Mpl ligand, e.g., cell or tissue sources. The steps are not required to be in a particular sequence, but the listed sequence is preferred. Procedures for culturing a cell (or tissue) source which may be found to produce Mpl ligand are known to those of skill in the art and may be used, for example, to expand the supply of starting material.

Mpl ligand or one or more peptide fragments thereof may also be produced via recombinant techniques. To obtain the DNA sequence for a particular Mpl ligand, the purified Mpl ligand material is reduced and optionally digested with a protease such as trypsin. Enzymatic fragments are isolated and sequenced by conventional techniques. Alternatively, as exemplified in the examples herein, the intact purified protein may be sequenced directly to the extent possible based on the quantity of protein available and then the sequenced region may be used analogously to the sequenced tryptic fragments in the following procedure. Oligonucleotide probes are synthesized using the genetic code to predict all possible sequences that encode the amino acid sequences of the sequenced fragment(s). Preferably, several degenerate sequences are generated as probes. The Mpl ligand gene is identified by using these probes to screen a mammalian genomic library or other source. Alternatively, the mRNA from a cell source of Mpl ligand can be used to make a cDNA library which can be screened with the probes to identify the cDNA encoding the Mpl ligand polypeptide. Further, the PCR technique may be used to extend the cDNA sequence, using appropriate primers.

Using these probes to screen a genomic library, a DNA clone is obtained. To obtain a full length clone, probes based on the obtained DNA sequence may be employed to rescreen the library and hybridize to the full length Mpl ligand DNA sequence.

The human cDNA for Mpl ligand can also be obtained by subcloning a full length human genomic clone into an expression vector, transfecting it into COS cells, preparing a cDNA library from these transfected COS cells and screening by hybridization for Mpl ligand cDNA. Once the entire cDNA is identified, it or any portion of it that encodes an active fragment of Mpl ligand, can be introduced into any one of a variety of expression vectors to make an expression system for Mpl ligand or one or more fragments thereof.

By such use of recombinant techniques, preferred DNA sequences encoding the Mpl ligand polypeptide are obtained. The present invention also encompasses these DNA sequences, free of association with DNA sequences encoding other proteins (i.e., isolated), and coding for expression of Mpl ligand polypeptides with an Mpl ligand activity (e.g., megakaryocyte growth and/or development). These DNA sequences include those sequences encoding all or a fragment of Mpl ligand and those sequences which hybridize, preferably under stringent hybridization conditions to the cDNA sequences [See, T. Maniatis et. al., *Molecular Cloning* (A Laboratory Manual); Cold Spring Harbor Laboratory (1982), pages 387–389].

Exemplary stringent hybridization conditions are hybridization in 4×SSC at 62°–67° C., followed by washing in 0.1× SSC at 62°–67° C. for approximately an hour. Alternatively, exemplary stringent hybridization conditions are hybridization in 45–55% formamide, 4×SSC at 40°–45° C.

DNA sequences which hybridize to the sequences for Mpl ligand under relaxed hybridization conditions and which encode Mpl ligand peptides having Mpl ligand biological properties also encode novel Mpl ligand polypeptides of this invention. Examples of such relaxed stringency hybridization conditions are 4×SSC at 45°–55° C. or hybridization with 30–40% formamide at 40°–45° C. For example, a DNA sequence which shares regions of significant homology, e.g., sites of glycosylation or disulfide linkages, with the sequences of Mpl ligand and encodes a protein having one or more Mpl ligand biological properties clearly encodes an Mpl ligand polypeptide even if such a DNA sequence would not stringently hybridize to the Mpl ligand sequence(s).

Allelic variations (naturally-occurring base changes in the species population which may or may not result in an amino acid change) of DNA sequences encoding the peptide sequences of Mpl ligand are also included in the present invention, as well as analogs or derivatives thereof. Similarly, DNA sequences which code for Mpl ligand polypeptides but which differ in codon usage due to the degeneracies of the genetic code or variations in the DNA sequence of Mpl ligand which are caused by point mutations or by induced modifications to enhance the activity, half-life or production of the polypeptides encoded thereby are also encompassed in the invention.

A cloning procedure as set forth in Example 11 below was followed and resulted in the amino acid and cDNA sequences of the human proteins MGDF-1 (amino acids 1-332 of SEQ ID NO: 25), MGDF-2 (amino acids 1-174 of SEQ ID NO: 25), and MGDF-3 (amino acids 1-265 of SEQ ID NO: 27) disclosed herein. MGDF-1 (amino acids 1-332 of SEQ ID NO: 25) is shown as amino acids 1-332 in FIG. 11 and contains 332 amino acids. MGDF-2 (amino acids 1-174 of SEQ ID NO: 25) is a truncated portion of MGDF-1(amino acids 1-332 of SEQ ID NO: 25), and is shown as amino acids 1-174 in FIG. 11. MGDF-2 (amino acids 1-174 of SEQ ID NO: 25) therefore contains 174 amino acids. MGDF-3 (amino acids 1-265 of SEQ ID NO: 27) is shown as amino acids 1-265 in FIG. 12 and contains 265 amino acids. In each MGDF disclosed herein, the molecule including the signal peptide, shown as amino acids -21 to -1 in both FIGS. 11 and 12, is also part of the present inventive polypeptides, but it is preferably removed for megakaryocyte growth and development activity to be exhibited. In summary, MGDFs 1–3 are defined as follows:

MGDF-1 amino acids 1-332 SEQ ID NO: 25
MGDF-2 amino acids 1-174 SEQ ID NO: 25
MGDF-3 amino acids 1-265 SEQ ID NO: 27.

Based on the activity data presented herein, it is hypothesized that human MGDF is expressed in vivo as a substantially inactive or less active precursor polypeptide that contains variable C-terminal amino acids. Upon cleavage of the C-terminal amino acids (as well as the signal peptide), the processed form(s) of the molecule retain activity or become more active.

In the assays presented herein, MGDF-1 (amino acids 1-332 of SEQ ID NO: 25) and MGDF-2 (amino acids 1-174 of SEQ ID NO: 25) were active whereas MGDF-3 (amino acids 1-265 of SEQ ID NO: 27) was not. In view of the above hypothesis, it is believed that MGDF-1 (amino acids 1-332 of SEQ ID NO: 25) may require processing (e.g., cleavage with a protease) in order to exhibit its activity. The fact that a truncated form of MGDF-1 (amino acids 1-332 of SEQ ID NO: 25) (i.e., MGDF-2(amino acids 1-174 of SEQ ID NO: 25)) is active supports this hypothesis.

Conditioned medium from human kidney 293 cells (Invitrogen) transfected with the MGDF-1 gene (nucleotides 99-1094 of SEQ ID NO: 24) does demonstrate activity in the cell assay of Example 4 below. On the other hand, in other cell lines, e.g., 32 D cells, no activity was seen for this molecule. It is hypothesized that this may mean that 293 cells are able to process the MGDF-1 (amino acids 1-332 of SEQ ID NO: 25) molecule, presumably by truncation, so that the molecule primarily responsible for the activity is a truncated form, whereas the 32 D cells are unable to process the molecule.

In view of the above hypothesis, various active molecules may result from truncations of the sequence set forth as MGDF-1 (amino acids 1-332 of SEQ ID NO; 25) (FIG. 11). Structural features conserved among the cytokine family, such as erythropoietin (EPO), include four α-helical bundles and four cysteines. Referring to the MGDF-1 (amino acids 1-332 of SEQ ID NO: 25) sequence, Cys 151 is the most C-terminal element of these evolutionarily conserved and functionally essential structures. Therefore, preferred truncation variants of MGDF-1 (amino acids 1-332 of SEQ ID NO: 25) are any of those that have C-terminal truncations from amino acid 152 to 332 (along with cleavage of the signal peptide). Preferably, the sequence of MGDF-1 (amino acids 1-332 of SEQ ID NO: 25) will have removed from it from 50 to 185 amino acids from the C-terminus, particularly preferably, from 90 to 172 amino acids from the C terminal. As disclosed herein, the signal peptide is thought to be 21 amino acids in length; however, the signal peptide may have 23 amino acids, based on the sequence of MGDF-1(amino acids 1-332 of SEQ ID NO: 25). Accordingly, polypeptides corresponding to those presented herein but which start at position 3 of FIG. 11 or 12 are also specifically contemplated.

The following are some specific preferred variants of MGDF-1 (amino acids 1-332 of SEQ ID NO: 25) that may exhibit activity (i.e., the ability to promote the growth of megakaryocytes and/or platelets; or inhibitory/ stimulatory activity towards the natural receptor):

MGDF-4 amino acids 1-151 SEQ ID NO: 25
MGDF-5 amino acids 1-156 SEQ ID NO: 25
MGDF-6 amino acids 1-170 SEQ ID NO: 25
MGDF-7 amino acids 1-177 SEQ ID NO: 25
MGDF-8 amino acids 1-244 SEQ ID NO: 25.

In some clones, amino acids 112-115 in the MGDF-1 (amino acids 1-332 of SEQ ID NO: 25) sequence were absent, so that sequences corresponding to those set forth above, but in which these amino acids are missing (and the C-terminus amino acid number adjusted down by 4) may also be active.

In one clone, which had a termination codon at position 171, an Ala residue was found instead of a Thr residue as shown at position 170 in FIG. 11. Therefore, the invention includes variants of MGDF molecules in which position 170 is Ala instead of Thr.

MGDF-3 (amino acids 1-265 of SEQ ID NO: 27) results from removal of a sequence referred to herein as IVS-5 (Intervening Sequence-5) since this sequence is spliced within the fifth exon in the sequence. Since the 5' end of IVS-5 occurs within a codon, its removal results in a frame-shift in the remaining sequence of MGDF, which can be seen to occur starting at position 139 of MGDF-3 (amino acids 1-265 of SEQ ID NO: 27) to the end of the molecule.

No activity has yet been found for MGDF-3 (amino acids 1-265 of SEQ ID NO: 27) itself upon transfection into 293 cells and testing the resulting conditioned medium for activity in the cell-based assay of Example 4. Apparently, unlike MGDF-1 (amino acids 1-332 of SEQ ID NO: 25), 293 cells are unable to process MGDF-3 (amino acids 1-265 of SEQ ID NO: 27) to an active form. Nevertheless, based on the truncation hypothesis set forth above in connection with MGDF-1 (amino acids 1-332 of SEQ ID NO: 25), truncation of C-terminal amino acids from MGDF-3 (amino acids 1-265 of SEQ ID NO: 27) may also result in activity. For example, C-terminal truncation of MGDF-3 (amino acids 1-265 of SEQ ID NO: 27) of from 40 to 102 amino acids may result in activity. Preferably, from 50 to 90 amino acids are removed. Two specific preferred variants of MGDF-2 (amino acids 1-174 of SEQ ID NO: 25) are:

MGDF-9 amino acids 1-158 of SEQ ID NO: 27
MGDF-10 amino acids 1-244 of SEQ ID NO: 27

In all of the Mpl ligands disclosed herein, including the exemplary MGDFs set forth above, a methionyl residue may be present at the N-terminus, especially when such polypeptides are expressed in bacterial host cells.

Mpl ligand polypeptides may also be produced by known conventional chemical synthesis. Methods for constructing the polypeptides of the present invention by synthetic means are known to those of skill in the art. The synthetically-constructed Mpl ligand polypeptide sequences, by virtue of sharing primary, secondary, or tertiary structural and conformational characteristics with Mpl ligand polypeptides may possess Mpl ligand biological properties in common therewith. Thus, they may be employed as biologically active or immunological substitutes for natural, purified Mpl ligand polypeptides in therapeutic and immunological processes.

Modifications in the peptides or DNA sequences encoding Mpl ligand can be made by one skilled in the art using known techniques. Modifications of interest in the Mpl ligand sequences may include the replacement, insertion or deletion of a selected amino acid residue in the coding sequences. Mutagenesis techniques for such replacement, insertion or deletion are well known to one skilled in the art. |See, e.g., U.S. Pat. No. 4,518,584.| Conservative changes in from 1 to 20 amino acids are preferred. Preferred peptides may be generated by proteolytic enzymes, or by direct chemical synthesis. Such variants are included within the meaning of Mpl ligand polypeptides and polynucleotides of the present invention.

Specific mutations of the sequences of the Mpl ligand polypeptide may involve modifications of a glycosylation site (e.g., serine, threonine, or asparagine). The absence of glycosylation or only partial glycosylation results from amino acid substitution or deletion at any asparagine-linked glycosylation recognition site or at any site of the molecule that is modified by addition of O-linked carbohydrate. An asparagine-linked glycosylation recognition site comprises a tripeptide sequence which is specifically recognized by appropriate cellular glycosylation enzymes. These tripeptide sequences are either Asn-Xaa-Thr or Asn-Xaa-Ser, where Xaa can be any amino acid other than Pro. A variety of amino acid substitutions or deletions at one or both of the first or third amino acid positions of a glycosylation recognition site (and/or amino acid deletion at the second position) results in non-glycosylation at the modified tripeptide sequence. Expression of such altered nucleotide sequences produces variants which are not glycosylated at that site.

Additional Analogs/Derivatives of MGDF

Other analogs and derivatives of the sequences of MGDF (Mpl ligands), which may retain MGDF (Mpl ligand) activity in whole or in part may also be prepared by one of skill in the art given the disclosures herein. Such modifications are also encompassed by this invention.

More particularly, the present invention also broadly includes chemically modified MGDF compositions and methods of making and using them. The present disclosure reveals that it is possible to modify MGDF and to enhance its properties.

In one aspect, the present invention relates to an MGDF product comprising an MGDF protein linked to at least one water soluble polymer moiety.

In another aspect, the present invention relates to an MGDF product wherein said MGDF protein is linked to at least one polyethylene glycol molecule.

In another aspect, the present invention relates to MGDF molecules attached to at least one polyethylene glycol molecule via an acyl or alkyl linkage.

Pegylation of MGDF may be carried out by any of the pegylation reactions known in the art. See, for example: *Focus on Growth Factors* 3 (2): 4–10 (1992); EP 0 154 316; EP 0 401 384; and the other publications cited herein that relate to pegylation. Preferably, the pegylation is carried out via an acylation reaction or an alkylation reaction with a reactive polyethylene glycol molecule (or an analogous reactive water-soluble polymer). These preferred means for derivatization with polyethylene glycol will now be discussed in greater detail.

Acylation

Figure 14:
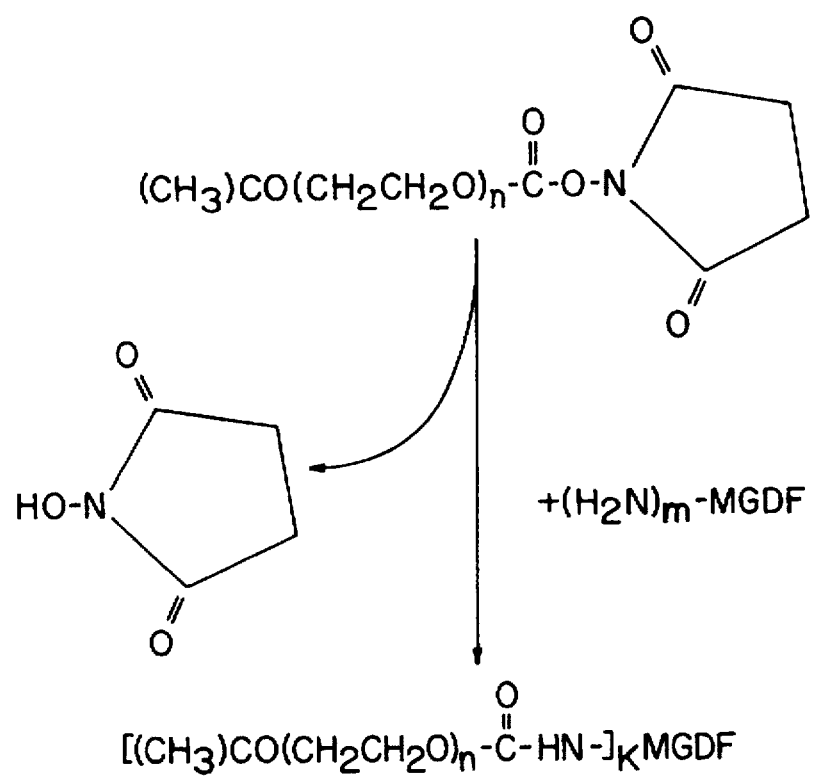
FIG. 14 shows an example of MGDF acylation using N-hydroxysuccinimidyl (NHS) active esters of mono-methoxy-polyethylene glycol to result in a poly-pegylated product.

Pegylation by acylation generally involves reacting an active ester derivative of polyethylene glycol (PEG) with an MGDF protein. Any known or subsequently discovered reactive PEG molecule may be used to carry out the pegylation of MGDF. A preferred activated PEG ester is PEG esterified to N-hydroxysuccinimide ("NHS"). As used herein, "acylation" is contemplated to included without limitation the following types of linkages between MGDF and a water soluble polymer such as PEG: amide, carbamate, urethane, and the like. See Bioconjugate Chem. 5: 133-140 (1994). Reaction conditions may be selected from any of those known in the pegylation art or those subsequently developed, but should avoid conditions such as temperature, solvent, and pH that would inactivate the MGDF species to be modified. Reaction conditions that apply generally to pegylation of MGDFs will be described below. An exemplary reaction with an NHS ester of monomethoxy-PEG is depicted in FIG. 14.

Pegylation by acylation will generally result in a polypegylated MGDF product, wherein the lysine ε-amino groups are pegylated via an acyl linking group. Preferably, the connecting linkage will be an amide. Also preferably, the resulting product will be substantially only (e.g.,>95%) mono, di- or tri-pegylated. However, some species with higher degrees of pegylation (up to the maximum number of lysine ε-amino acid groups of MGDF plus one α-amino group at the amino terminus of MGDF) will normally be formed in amounts depending on the specific reaction conditions used. If desired, more purified pegylated species may be separated from the mixture, particularly unreacted species, by standard purification techniques, including, among others, dialysis, salting-out, ultrafiltration, ion-exchange chromatography, gel filtration chromatography and electrophoresis.

Alkylation

Pegylation by alkylation generally involves reacting a terminal aldehyde derivative of PEG with a protein such as MGDF in the presence of a reducing agent. As with acylation, discussed above, the reaction conditions are described below.

Figure 16:
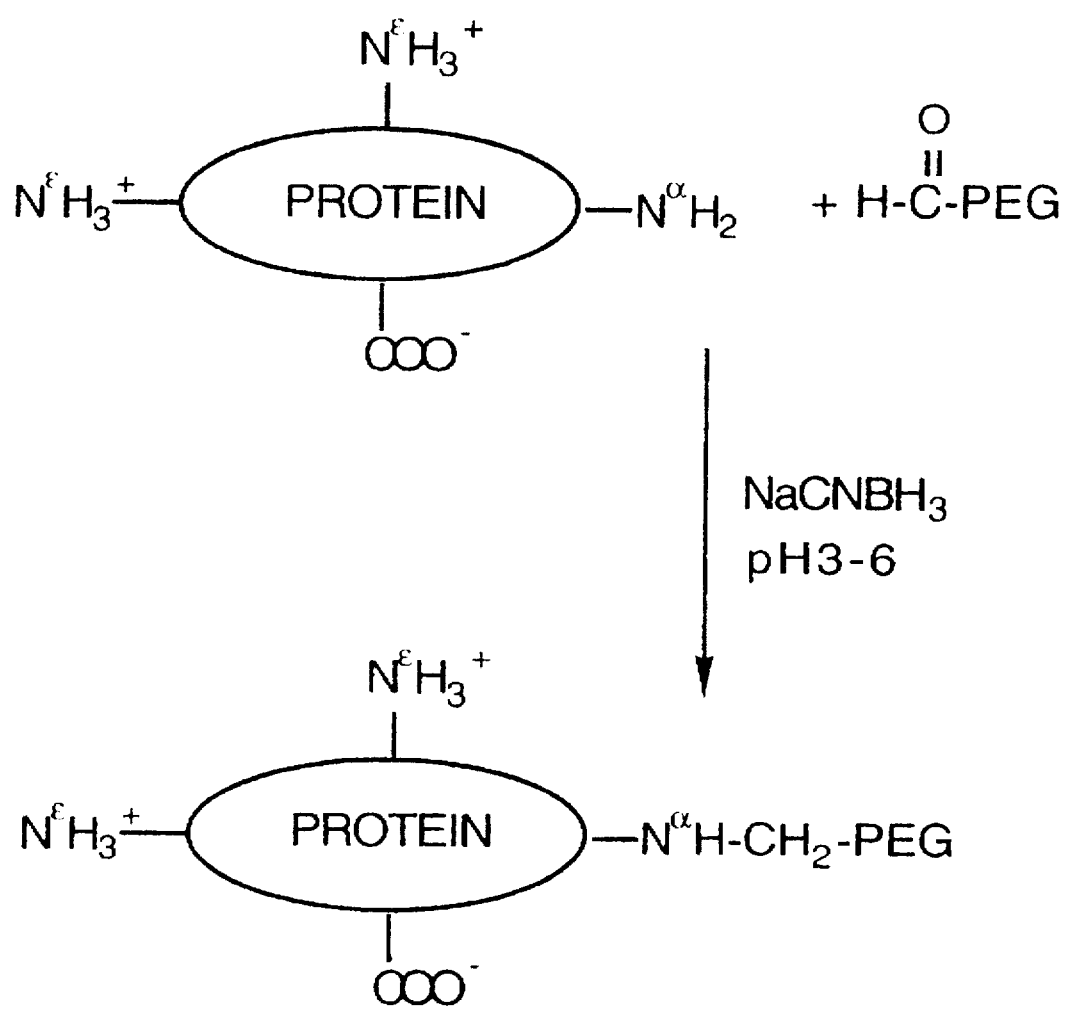
FIG. 16 shows an example of site-specific MGDF reductive alkylation at the α-amino group of the N-terminal residue using mono-methoxy-polyethylene glycol aldehydes to result in a substantially mono-pegylated product.

Pegylation by alkylation can also result in poly-pegylated MGDF. An exemplary reductive alkylation reaction with MGDF to yield a polypegylated product is shown in FIG. 15. In addition, one can manipulate the reaction conditions as described herein to favor pegylation substantially only at the α-amino group of the N-terminus of the MGDF species (i.e., a mono-pegylated species). An exemplary reductive alkylation reaction with MGDF to yield a monopegylated product is shown in FIG. 16. In either case of monopegylation or polypegylation, the PEG groups are preferably attached to the protein via a —CH$_2$—NH— group. With particular reference to the —CH$_2$— group, this type of linkage is referred to herein as an "alkyl" linkage.

Derivatization via reductive alkylation to produce a monopegylated product exploits differential reactivity of different types of primary amino groups (lysine versus the N-terminal) available for derivatization in MGDF. The reaction is performed at a pH (see below) which allows one to take advantage of the pK$_a$ differences between the ε-amino groups of the lysine residues and that of the α-amino group of the N-terminal residue of the protein. By such selective derivatization, attachment of a water soluble polymer that contains a reactive group such as an aldehyde, to a protein is controlled: the conjugation with the polymer takes place predominantly at the N-terminus of the protein and no significant modification of other reactive groups, such as the lysine side chain amino groups, occurs. In one important aspect, the present invention provides for a substantially homogeneous preparation of monopolymer/MGDF protein conjugate molecules (meaning MGDF protein to which a polymer molecule has been attached substantially only (i.e., ≧95%) in a single location). More specifically, if polyethylene glycol is used, the present invention also provides for pegylated MGDF protein lacking possibly antigenic linking groups, and having the polyethylene glycol molecule directly coupled to the MGDF protein.

Thus, in a preferred aspect, the present invention relates to pegylated MGDF, wherein the PEG group(s) is (are) attached via acyl or alkyl groups. As discussed above, such products may be mono-pegylated or poly-pegylated (e.g., containing 2-6, preferably 2-5, PEG groups). The PEG groups are generally attached to the protein at the α or ε amino groups of amino acids, but it is also contemplated that the PEG groups could be attached to any amino group attached to the protein, which is sufficiently reactive to become attached to a PEG group under suitable reaction conditions.

The polymer molecules used in both the acylation and alkylation approaches may be selected from among water soluble polymers or a mixture thereof. The polymer selected should be water soluble so that the protein to which it is attached does not precipitate in an aqueous environment, such as a physiological environment. The polymer selected should be modified to have a single reactive group, such as an active ester for acylation or an aldehyde for alkylation, preferably, so that the degree of polymerization may be controlled as provided for in the present methods. A preferred reactive PEG aldehyde is polyethylene glycol propionaldehyde, which is water stable, or mono C1–C10 alokoxy or aryloxy derivatives thereof (see, U.S. Pat. No. 5,252,714). The polymer may be branched or unbranched. Preferably, for therapeutic use of the end-product preparation, the polymer will be pharmaceutically acceptable. The water soluble polymer may be selected from the group consisting of, for example, polyethylene glycol, monomethoxy-polyethylene glycol, dextran, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol. For the acylation reactions, the polymer (s) selected should have a single reactive ester group. For the present reductive alkylation, the polymer(s) selected should have a single reactive aldehyde group. Generally, the water soluble polymer will not be selected from naturally-occurring glycosyl residues since these are usually made more conveniently by mammalian recombinant expression systems. The polymer may be of any molecular weight, and may be branched or unbranched.

A particularly preferred water-soluble polymer for use herein is polyethylene glycol, abbreviated PEG. As used herein, polyethylene glycol is meant to encompass any of the forms of PEG that have been used to derivatize other proteins, such as mono-(C1–C10) alkoxy- or aryloxy-polyethylene glycol.

As employed herein, MGDF is defined as including any of the various forms of MGDF described herein. For example, full-length or truncated, glycosylated or nonglycosylated forms of MGDF are all included. The following are preferred MGDF molecules to be derivatized (in each case the numbering refers to the amino acids numbered in accordance with FIG. 11):

MGDF-1: amino acids 1-332 of SEQ ID NO: 25
MGDF-2: amino acids 1-174 of SEQ ID NO: 25

MGDF-4: amino acids 1-151 of SEQ ID NO: 25
MGDF-11: amino acids 1-163 of SEQ ID NO: 25
MGDF-12: amino acids 6-332 of SEQ ID NO: 25
MGDF-13: amino acids 6-174 of SEQ ID NO: 25
MGDF-14: amino acids 6-151 of SEQ ID NO: 25
MGDF-15: amino acids 6-163 of SEQ ID NO: 25.

The above-preferred species may be glycosylated, non-glycosylated, or de-glycosylated, preferably non-glycosylated. They may be made recombinantly in either bacterial (e.g., E. coli) or mammalian (e.g., CHO) cells.

The following are particularly preferred sub-groups of chemically derivatized molecules of this invention (in each case, they are mono- or poly-, e.g., 2-4, PEG moieties, attached via an acyl or alkyl group):

pegylated MGDF-11 (amino acids 1-163 of SEQ ID NO: 25)

pegylated MGDF-4 (amino acids 1-151 of SEQ ID NO: 25)

pegylated MGDF-2 (amino acids 1-174 of SEQ ID NO: 25)

In general, chemical derivatization may be performed under any suitable condition used to react a biologically active substance with an activated polymer molecule. Methods for preparing pegylated MGDF will generally comprise the steps of (a) reacting an MGDF polypeptide with polyethylene glycol (such as a reactive ester or aldehyde derivative of PEG) under conditions whereby MGDF becomes attached to one or more PEG groups, and (b) obtaining the reaction product(s). In general, the optimal reaction conditions for the acylation reactions will be determined case-by-case based on known parameters and the desired result. For example, the larger the ratio of PEG: protein, the greater the percentage of poly-pegylated product.

Reductive alkylation to produce a substantially homogeneous population of mono-polymer/MGDF protein conjugate molecule will generally comprise the steps of: (a) reacting an MGDF protein with a reactive PEG molecule under reductive alkylation conditions, at a pH suitable to permit selective modification of the α-amino group at the amino terminus of said MGDF protein; and (b) obtaining the reaction product(s).

For a substantially homogeneous population of mono-polymer/MGDF protein conjugate molecules, the reductive alkylation reaction conditions are those which permit the selective attachment of the water soluble polymer moiety to the N-terminus of MGDF. Such reaction conditions generally provide for $pK_a$ differences between the lysine amino groups and the α-amino group at the N-terminus (the $pK_a$ being the pH at which 50% of the amino groups are protonated and 50% are not). The pH also affects the ratio of polymer to protein to be used. In general, if the pH is lower, a larger excess of polymer to protein will be desired (i.e., the less reactive the N-terminal αa-amino group, the more polymer needed to achieve optimal conditions). If the pH is higher, the polymer:protein ratio need not be as large (i.e., more reactive groups are available, so fewer polymer molecules are needed). For purposes of the present invention, the pH will generally fall within the range of 3-9, preferably 3-6.

Another important consideration is the molecular weight of the polymer. In general, the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio. In general, for the pegylation reactions contemplated herein, the preferred average molecular weight is about 2 kDa to about 100 kDa (the term "about" indicating ±1 kDa). The preferred average molecular weight is about 5 kDa to about 50 kDa, particularly preferably about 12 kDa to about 25 kDa. The ratio of water-soluble polymer to MGDF protein will generally range from 1:1 to 100:1, preferably (for polypegylation) 1:1 to 20:1 and (for monopegylation) 1:1 to 5:1.

Using the conditions indicated above, reductive alkylation will provide for selective attachment of the polymer to any MGDF protein having an α-amino group at the amino terminus, and provide for a substantially homogenous preparation of monopolymer/MGDF protein conjugate. The term "monopolymer/MGDF protein conjugate" is used here to mean a composition comprised of a single polymer molecule attached to an MGDF protein molecule. The monopolymer/MGDF protein conjugate will have a polymer molecule located at the N-terminus, but not on lysine amino side groups. The preparation will preferably be greater than 90% monopolymer/MGDF protein conjugate, and more preferably greater than 95% monopolymer MGDF protein conjugate, with the remainder of observable molecules being unreacted (i.e., protein lacking the polymer moiety). The examples below provide for a preparation which is at least about 90% monopolymer/ protein conjugate, and about 10% unreacted protein. The monopolymer/protein conjugate has biological activity.

For the present reductive alkylation, the reducing agent should be stable in aqueous solution and preferably be able to reduce only the Schiff base formed in the initial process of reductive alkylation. Preferred reducing agents may be selected from the group consisting of sodium borohydride, sodium cyanoborohydride, dimethylamine borane, timethylamine borane and pyridine borane. A particularly preferred reducing agent is sodium cyanoborohydride.

Other reaction parameters, such as solvent, reaction times, temperatures, etc., and means of purification of products, can be determined case-by-case based on the published information relating to derivatization of proteins with water soluble polymers (see the publications cited herein). Exemplary details are shown in the Examples section below.

One may choose to prepare a mixture of polymer/protein conjugate molecules by acylation and/or alkylation methods, and the advantage provided herein is that one may select the proportion of monopolymer/ protein conjugate to include in the mixture. Thus, if desired, one may prepare a mixture of various protein with various numbers of polymer molecules attached (i.e., di-, tri-, tetra-, etc.) and combine with the monopolymer/protein conjugate material prepared using the present methods, and have a mixture with a predetermined proportion of monopolymer/protein conjugate.

The working e

The working examples below demonstrate the preparation of chemically modified MGDF and the preparation of MGDF pegylated via acylation and alkylation. Thus, other aspects of the present invention relate to these preparations.

Generally, conditions which may be alleviated or modulated by administration of the present polymer/MGDF include those described above for MGDF molecules in general. However, the polymer/MGDF molecules disclosed herein may have additional activities, enhanced or reduced activities, or other characteristics, as compared to the non-derivatized molecules.

In yet another aspect of the present invention, provided are pharmaceutical compositions of the above. Such pharmaceutical compositions may contain any of the ingredients specified above for non-derivatized MGDF molecules.

As further studies are conducted, information will emerge regarding appropriate dosage levels for treatment of various conditions in various patients, and the ordinary skilled worker, considering the therapeutic context, age and general health of the recipient, will be able to ascertain proper dosing. Generally, the dosage will be between 0.01 µg/kg body weight (calculating the mass of the protein alone, without chemical modification) and 300 µg/kg (based on the same). The preferred dose will generally be from 5 µg/kg body weight to 100 µg/kg body weight, particularly preferably from 10 µg/kg body weight to 75 µg/kg body weight.

The present invention also provides a method for producing MGDF (i.e., Mpl ligand) polypeptides or active fragments thereof. One method of the present invention involves introducing the cDNA encoding an Mpl ligand polypeptide into an expression vector to make an expression system for Mpl ligand. A selected host cell is transfected with the vector and cultured. The method of this present invention therefore comprises culturing a suitable cell or cell line, which has been transfected with a DNA sequence coding on expression for an Mpl ligand polypeptide under the control of known regulatory sequences. Regulatory sequences include promoter fragments, terminator fragments and other suitable sequences which direct/control the expression of the protein in an appropriate host cell. The expressed factor is then recovered, isolated and purified from the culture medium (or from the cell, if expressed intracellularly) by appropriate means known to one of skill in the art. Additionally, the methods disclosed in U.S. Pat. No. 5,272,071 are also contemplated to be applicable to the inventive polynucleotides/ polypeptides.

Suitable cells or cell lines may be mammalian cells, such as Chinese hamster ovary cells (CHO) or 3T3 cells. The selection of suitable mammalian host cells and methods for transformation, culture, amplification, screening and product production and purification are known in the art. See, e.g., Gething and Sambrook, Nature 293: 620–625 (1981), or alternatively, Kaufman et al., Mol. Cell. Biol., 5 (7): 1750–1759 (1985) or Howley et al., U.S. Pat. No. 4,419,446. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, HeLa, mouse L-929 cells, 3T3 lines derived from Swiss, Balb-c or NIH mice, BHK or HaK hamster cell lines.

Similarly useful as host cells suitable for the present invention are bacterial cells. For example, the various strains of E. coli (e.g., HB101, DH5α,DH10, and MC1061) are well-known as host cells in the field of biotechnology. Various strains of B. subtilis, Pseudomonas spp., other Bacillus spp., Streptomyces spp., and the like may also be employed in this method.

Many strains of yeast cells known to those skilled in the art are also available as host cells for expression of the polypeptides of the present invention. Additionally, where desired, insect cells may be utilized as host cells in the method of the present invention. See, e.g. Miller et al., Genetic Engineering 8: 277–298 (1986) and references cited therein.

The present invention also provides recombinant molecules or vectors for use in the method of expression of novel Mpl ligand polypeptides. These vectors contain the Mpl ligand DNA sequences and which alone or in combination with other sequences code for Mpl ligand polypeptides (with or without signal peptides) of the invention or active fragments thereof. Alternatively, vectors incorporating modified sequences as described above are also embodiments of the present invention and useful in the production of Mpl ligand polypeptides. The vector employed in the method also contains selected regulatory sequences in operative association with the DNA coding sequences of the invention and capable of directing the replication and expression thereof in selected host cells.

One vector is pXM, which is particularly desirable for expression in COS cells [Y. C. Yang et al., Cell 47: 3–10 (1986)]. Another vector which is desirable for expression in mammalian cells, e.g., CHO cells, is pEMC2B1. Mammalian cell expression vectors described herein may be synthesized by techniques well known to those skilled in this art. The components of the vectors, e.g. replicons, selection genes, enhancers, promoters, and the like, may be obtained from natural sources or synthesized by known procedures. See, Kaufman et al., J. Mol. Biol. 159: 511–521 (1982); and Kaufman, Proc. Natl. Acad. Sci. USA 82: 689–693 (1985). Alternatively, the vector DNA may include all or part of the bovine papilloma virus genome [Lusky et al., Cell 36: 391–401 (1984)] and be replicated in cell lines such as C127 mouse cells as a stable episomal element. The transfection of these vectors into appropriate host cells can result in expression of the Mpl ligand polypeptides.

Other appropriate expression vectors of which numerous types are known in the art for mammalian, insect, yeast, fungal and bacterial expression can also be used for this purpose.

The conditions to be treated by the methods and compositions of the present invention are generally those which involve an existing megakaryocyte/platelet deficiency or an expected megakaryocyte/platelet deficiency in the future (e.g., because of planned surgery). Such conditions will usually be the result of a deficiency (temporary or permanent) of active Mpl ligand in vivo. The generic term for platelet deficiency is thrombocytopenia, and hence the methods and compositions of the present invention are generally available for treating thrombocytopenia.

Thrombocytopenia (platelet deficiencies) may be present for various reasons, including chemotherapy and other therapy with a variety of drugs, radiation therapy, surgery, accidental blood loss, and other specific disease conditions. Exemplary specific disease conditions that involve thrombocytopenia and may be treated in accordance with this invention are: aplastic anemia, idiopathic thrombocytopenia, metastatic tumors which result in thrombocytopenia, systemic lupus erythematosus, splenomegaly, Fanconi's syndrome, vitamin B12 deficiency, folic acid deficiency, May-Hegglin anomaly, Wiskott-Aldrich syndrome, and paroxysmal nocturnal hemoglobinuria. Also, certain treatments for AIDS result in thrombocytopenia (e.g., AZT). Certain wound healing disorders might also benefit from an increase in platelet numbers.

With regard to anticipated platelet deficiencies, e.g., due to future surgery, an Mpl ligand of the present invention could be administered several days to several hours prior to the need for platelets. With regard to acute situations, e.g., accidental and massive blood loss, an Mpl ligand could be administered along with blood or purified platelets.

The Mpl ligands of this invention may also be useful in stimulating certain cell types other than megakaryocytes if such cells are found to express Mpl receptor. Conditions associated with such cells that express the Mpl receptor, which are responsive to stimulation by the Mpl ligand, are also within the scope of this invention.

MGDF molecules that are not themselves active in the activity assays presented herein may be useful as modulators (e.g., inhibitors or stimulants) of the Mpl receptors in vitro or in vivo.

The polypeptides of the present invention may also be employed alone, or in combination with other cytokines, soluble Mpl receptor, hematopoietic factors, interleukins, growth factors or antibodies, in the treatment of the above-identified conditions.

Therefore, as yet another aspect of the invention are therapeutic compositions for treating the conditions referred to above. Such compositions comprise a therapeutically effective amount of an Mpl ligand polypeptide or a therapeutically effective fragment thereof in admixture with a pharmaceutically acceptable carrier. The carrier material may be water for injection, preferably supplemented with other materials common in solutions for administration to mammals. Typically, an Mpl ligand therapeutic will be administered in the form of a composition comprising purified protein in conjunction with one or more physiologically acceptable carriers, excipients, or diluents. Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired.

The present compositions can be systemically administered parenterally. Alternatively, the compositions may be administered intravenously or subcutaneously. When systemically administered, the therapeutic compositions for use in this invention may be in the form of a pyrogen-free, parenterally acceptable aqueous solution. The preparation of such pharmaceutically acceptable protein solutions, with due regard to pH, isotonicity, stability and the like, is within the skill of the art.

The dosage regimen involved in a method for treating the above-described conditions will be determined by the attending physician, considering various factors which modify the action of drugs, e.g. the age, condition, body weight, sex and diet of the patient, the severity of any infection, time of administration and other clinical factors. Generally, the daily regimen should be in the range of 0.1–1000 micrograms of Mpl ligand protein or fragment thereof per kilogram of body weight.

The therapeutic methods, compositions and polypeptides of the present invention may also be employed, alone or in combination with other cytokines, soluble Mpl receptor, hematopoietic factors, interleukins, growth factors or antibodies in the treatment of disease states characterized by other symptoms as well as platelet deficiencies. It is anticipated that an Mpl ligand molecule will prove useful in treating some forms of thrombocytopenia in combination with general stimulators of hematopoiesis, such as IL-3 or GM-CSF. Other megakaryocytic stimulatory factors, i.e., meg-CSF, stem cell factor (SCF), leukemia inhibitory factor (LIF), oncostatin M (OSM), or other molecules with megakaryocyte stimulating activity may also be employed with Mpl ligand. Additional exemplary cytokines or hematopoietic factors for such co-administration include IL-1 alpha, IL-1 beta, IL-2, IL-3, IL-4, IL-5, IL-6, IL-11, colony stimulating factor-1 (CSF-1), GM-CSF, granulocyte colony stimulating factor (G-CSF), EPO, interferon-alpha (IFN-alpha), IFN-beta, or IFN-gamma. It may further be useful to administer, either simultaneously or sequentially, an effective amount of a soluble mammalian Mpl receptor, which appears to have an effect of causing megakaryocytes to fragment into platelets once the megakaryocytes have reached mature form. Thus, administration of Mpl ligand (to enhance the number of mature megakaryocytes) followed by administration of the soluble Mpl receptor (to inactivate the ligand and allow the mature megakaryocytes to produce platelets) is expected to be a particularly effective means of stimulating platelet production. The dosage recited above would be adjusted to compensate for such additional components in the therapeutic composition. Progress of the treated patient can be monitored by conventional methods.

Other uses for these novel polypeptides are in the development of antibodies generated by standard methods. Thus, antibodies that react with the Mpl ligands of the present invention, as well as reactive fragments of such antibodies, are also contemplated. The antibodies may be polyclonal, monoclonal, recombinant, chimeric, single-chain and/or bispecific, etc. The antibody fragments may be any fragment that is reactive with the Mpl ligand of the present invention, such as, $F_{ab}$, $F_{ab}'$, etc. Also provided by this invention are the hybridomas generated by presenting Mpl ligand or a fragment thereof as an antigen to a selected mammal, followed by fusing cells (e.g., spleen cells) of the animal with certain cancer cells to create immortalized cell lines by known techniques. The methods employed to generate such cell lines and antibodies directed against all or portions of a human Mpl ligand polypeptide of the present invention are also encompassed by this invention.

The antibodies may be used therapeutically, such as to inhibit binding of the Mpl ligand and its receptor. The antibodies may further be used for in vivo and in vitro diagnostic purposes, such as in labeled form to detect the presence of the Mpl ligand in a body fluid.

The following examples are included to more fully illustrate the present invention. Additionally, these examples provide preferred embodiments of the invention, but are not meant to limit the scope thereof, unless so indicated. Standard methods for many of the procedures described in the following examples, or suitable alternative procedures, are provided in widely recognized manuals of molecular biology such as, for example, Sambrook et al., *Molecular Cloning*, Second Edition, Cold Spring Harbor Laboratory Press (1987) and in Ausubel et al., (Eds), *Current Protocols in Molecular Biology*, Greene associates/Wiley Interscience, New York (1990).

EXAMPLE 1

Aplastic Canine Plasma

Heparinized aplastic canine plasma ("APK9") or normal canine plasma ("NK9") was produced as described in the following publications, except that 450 rads of total body irradiation were delivered to recipients:

1. Mazur, E. and South, K. *Exp. Hematol.* 13:1164–1172 (1985).
2. Arriaga, M., South, K., Cohen, J. L., and Mazur, E. M. *Blood* 69: 486–492 (1987).
3. Mazur, E., Basilico, D., Newton, J. L., Cohen, J. L., Charland, C., Sohl, P. A., and Narendran, A. *Blood* 76: 1771–1782 (1990).

EXAMPLE 2

Human Megakaryocyte Assay

APK9 and fractionated APK9 were assayed for the ability to stimulate development of human megakaryocytes from CD34+ progenitor cells. CD34-selected cells were obtained from peripheral blood cells as described (Hokom, M. H., Choi, E., Nichol, J. L., Hornkohl, A., Arakawa, T., and Hunt, P. Molecular *Biology of Haematopoiesis* 3:15–31,1994) and were incubated in the following culture medium: Iscove's modified Dulbecco's medium (IMDM; GIBCO, Grand Island, NY) supplemented with 1% Glutamine Pen-strep (Irvine Scientific, Santa Ana, Calif.) and 10% heparinized, platelet-poor, human AB plasma. Also included were 2-mercaptoethanol ($10^{-4}$M), pyruvic acid (110 µg/ml), cholesterol (7.8 µg/ml), adenosine, guanine, cytidine, uridine, thymidine, 2-deoxycytosine, 2-deoxyadenosine, 2-deoxyguanosine (10 µg/ml each, Sigma); human recombinant insulin (10 µg/ml), human transferrin (300 µg/ml), soybean lipids (1%, Boehringer Mannheim, Indianapolis, Ind.); human recombinant basic fibroblast growth factor (2 ng/ml, Genzyme, Cambridge, Mass.); human recombinant epidermal growth factor (15 ng/ml), platelet-derived growth factor (10 ng/ml, Amgen, Inc., Thousand Oaks, Calif.). CD34-selected cells were plated at $2\times10^5$/ml culture medium, 15 ul final volume, in wells of Terasaki-style microtiter plates (Vanguard, Inc., Neptune, N.J.). Cells were incubated at 37° C. for 8 days in humidified boxes in 5% $CO_2$ in air, fixed directly to the culture wells with 1% glutaraldehyde, and incubated with a monoclonal antibody cocktail (anti-GPIb, anti-GPIIb, (Biodesign) and anti-GPIb (Dako, Carpinteria, Calif.). The immune reaction was developed with a streptavidin-beta-galactosidase detection system (HistoMark, Kirkegaard and Perry). Megakaryocytes, identified by a blue color, were counted with an inverted phase microscope at 100× magnification. Results were presented as the average number of megakaryocytes per well ± standard error of the mean (SEM). In some cases, data were presented in terms of "megakaryocyte units/ml" where the degree to which a given sample induced megakaryocyte development was normalized to the positive APK9 control for that experiment. One unit is defined as the amount of material that results in the same number of megakaryocytes as 1 ul of APK9 standard. Activity was accepted as due to MPL ligand if it could be blocked with 5–10 ug/ml MPL-X (soluble Mpl receptor).

APK9 has been demonstrated to contain factor(s) that stimulate human megakaryocyte development in this system. CD34-selected cells incubated with 10% NK9 for 8 days show a negligible number of blue-stained megakaryocytes, whereas CD34-selected cells incubated with 10% APK9 for 8 days show a very large number of blue-stained megakaryocytes.

Figure 2:
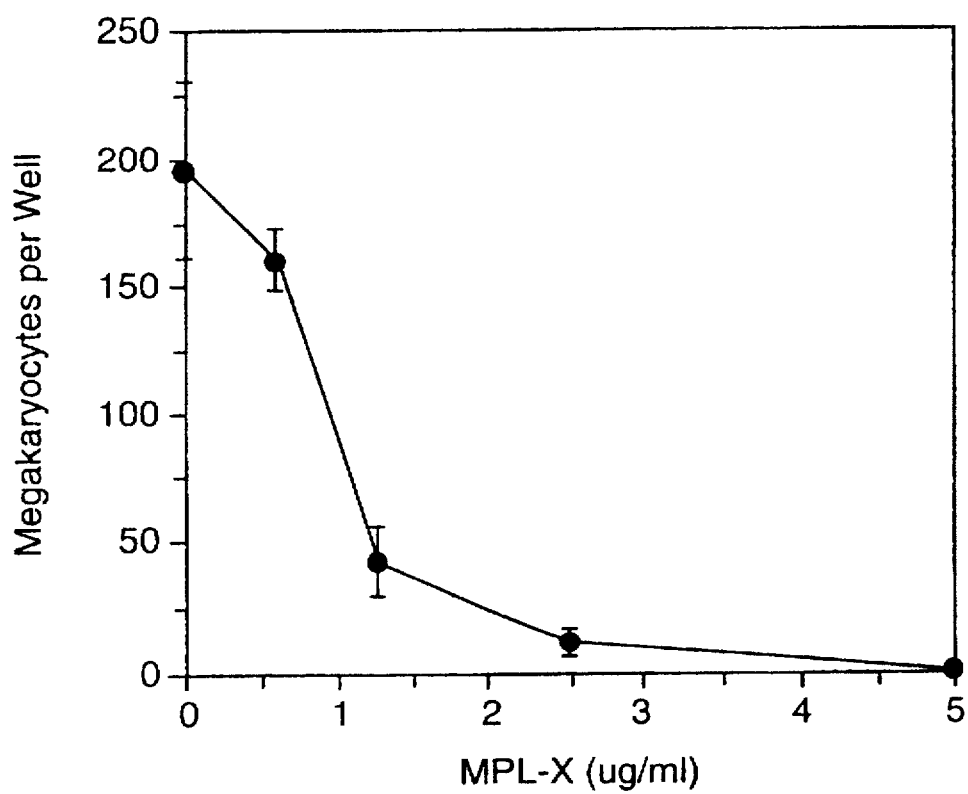
FIG. 2 demonstrates that soluble murine Mpl receptor substantially completely inhibits the ability of plasma from irradiated dogs ("aplastic canine" or "APK9"), to induce megakaryocyte development. The assay for megakaryocyte development was that described in Example 2.

FIG. 2 shows that increasing concentrations of Mpl-X added to the human megakaryocyte culture system increasingly block megakaryocyte development. At concentrations of Mpl-X greater than 5 µg/ml, inhibition is complete. In this experiment, CD34-selected cells were stimulated with 5% APK9. This demonstrates that an activity which interacts with Mpl-X (presumptive Mpl ligand) is necessary for human megakaryocyte development, and implies that the Mpl ligand is present in APK9 itself.

It has been further demonstrated herein that the Mpl ligand activity necessary for human megakaryocyte development is present in APK9. APK9 (135 ml) was diluted 6-fold into Iscove's media and applied to an Mpl-X affinity column. Unbound material (flow through) was collected and concentrated to the original volume before assay. Bound material was eluted in 10 ml of 1M NaCl, and 20% of the pool was diafiltered and concentrated 4-fold for assay. CD34-selected cells incubated in media alone did not develop into megakaryocytes. Cells incubated in 5% APK9 (same pool as applied to column) developed into 48±8 megakaryocytes per well. Cells incubated in 10% of the unbound material did not develop into megakaryocytes. Cells incubated in 10% of the elution pool developed into 120±44 megakaryocytes per well. Both the column load and the elution pool activities were substantially completely inhibited with 5 µg/ml Mpl-X in the assay.

EXAMPLE 3

Transfection of murine or human Mpl receptor into a murine cell line

A. Murine Mpl Receptor

The full length murine Mpl receptor cDNA was subcloned into an expression vector containing a transcriptional promoter derived from the LTR of Moloney Murine Sarcoma virus. 5 µg of this construct and 1 µg of the selectable marker plasmid pWLNeo (Stratagene) were co-electroporated into an IL-3 dependent murine cell line (32D, clone 23; Greenberger et al., *PNAS* 80: 2931–2936 (1983)). Cells were cultured for 5 days to recover from the procedure, then incubated in selection media including 800 ug/ml Geneticin (G418, Sigma) and 1 ng/ml murine IL-3. The surviving cells were then divided into pools of $2\times10^5$ cells and cultured until a population grew out which could be further analyzed. Six populations were tested for surface expression of Mpl receptor by FACS analysis using a polyclonal rabbit antipeptide serum. One population was chosen for FACS sorting using the same antipeptide serum as before. Single-cell clones of the parent cell line were selected by growth in 10% APK9 and Geneticin. After selection in APK9 for 35 days, the cells were maintained in 1 ng/ml murine IL-3. One of the subclones, 1A6.1, was used for this body of work.

B. Human Mpl Receptor

The full length human Mpl receptor sequence (Vigon, I., et al., *PNAS* 89: 5640–5644 (1992)) was subcloned into an expression vector containing the transcriptional promoter of Moloney Murine Sarcoma virus (same vector as with the murine receptor). Six µg of this construct and 6 µg of an amphotrophic retroviral packaging construct (Landau, N. R., Littman, D. R., J. *Virology* 66: 5110–5113 (1992)) were transfected into $3\times10^6$293 cells using a $CaPO_4$ mammalian transfection kit (Stratagene). The same cells were retransfected after 2 days and again after 4 days. The day after the last transfection the 293 cells were cocultivated with the IL-3 dependent murine cell line (32 D, clone 23; Greenberger et al., *PNAS* 80: 2931–2936 (1983)). After 24 hours, the 32 D cells were rescued and banded in a BSA gradient (Path-o-cyte; Miles Inc.). Cells were expanded in 1 ng/ml murine IL-3 and then were selected for growth in 20% APK9. Cells were sorted for cell surface expression of receptor by FACS using a polyclonal rabbit antipeptide serum. These cells were subsequently used in the assays.

EXAMPLE 4

1A6.1 assay for Mpl ligand

1A6.1 cells were washed free of culture IL-3 and replated (1000 cells/15 µl total vol/well) in Terasaki-style microtiter plates in alpha MEM (Gibco) supplemented with 10% fetal calf serum (FCS), Geneticin (800 µg/ml) and 1% pen/strep (Gibco) in 1:1 serial dilutions of test samples. After 48 hours, the number of viable cells per well was determined microscopically. One unit of activity was defined as that amount of activity that resulted in 200 viable cells per well. Activity was defined as due to Mpl ligand if it could be completely blocked by including 5–10 µg/ml Mpl-X in the assay. Mpl ligand activity in APK9 averaged 4400±539 units/ml of aplastic plasma. Unless otherwise indicated, units of Mpl ligand activity are defined in the 1A6.1 assay.

Assays with cells transfected with the human Mpl receptor gene (Example 3B) were carried out in essentially the same manner as with the 1A6.1 cells.

EXAMPLE 5

Demonstration that Mpl-ligand is present in aplastic plasma or sera of mouse, dog, pig and human sources Mpl ligand is present in the aplastic plasma or sera from murine, canine, porcine and human sources (Table 2). Plasma was collected from BDF1 mice pre-irradiation and 12 days post-irradiation (500 rads). Plasma was tested in the 1A6.1 assay where it demonstrated 2000 units/ml activity that was substantially completely inhibitable with Mpl-X (10 ug/ml). Irradiated mouse plasma was also positive in the human megakaryocyte assay where it displayed an activity of 1833 units/ml. Plasma was collected from dogs pre-irradiation and 10 days post-irradiation (450 rads). Plasma was tested in both the 1A6.1 assay and human megakaryocyte assays. Activity was detected and completely inhibited by Mpl-X (10 ug/ml) in both assays. Plasma was collected from pigs pre-irradiation and 10 days post-irradiation (650 rads). Plasma was tested in both the 1A6.1 assay and the human megakaryocyte assays. In both assays it displayed Mpl ligand activity (inhibitable by 10 ug/ml Mpl-X) comparable to that found in aplastic canine plasma. Sera from aplastic humans was obtained. This material was collected from bone marrow transplantation patients. The sera from 6 patients were assayed in the 1A6.1 assay where it showed an activity of 903 units/ml, 88% of which was due to Mpl ligand (inhibitable with 10 ug/ml Mpl-X). Sera from 14 aplastic patients has also been tested in the human megakaryocyte assay. As a group, they displayed substantial activity, 941 meg units/ml, which was completely inhibitable with 10 ug/ml Mpl-X. Murine IL-3 data is included to demonstrate the specificity of the 1A6.1 assay. Although this recombinant cytokine induces growth of the cell line, it is not blocked by 10 ug/ml Mpl-X.

TABLE 2

| Species | 1A6.1 Cell Assay (units/ml) | | Human Meg Assay (meg units/ml) | |
|---|---|---|---|---|
| | media | +Mpl-X | media | +Mpl-X |
| Normal mouse | 0+/−0 | 0+/−0 | 0+/−0 | 0+/−0 |
| Aplastic mouse | 2000 | 0 | 1833 | not done |
| Normal canine | 0+/−0 | 0+/−0 | 0+/−0 | 0+/−0 |
| Aplastic canine | 4400+/−539 | 0+/−0 | 792+/−128 | 0+/−0 |
| Normal porcine | 0+/−0 | 0+/−0 | 0+/−0 | 0+/−1 |
| Aplastic porcine | 3866+/−1136 | 0+/−0 | 1284+/−182 | 10+/−10 |
| Normal human | 0+/−0 | 0+/−0 | 0+/−0 | 0+/−0 |
| Aplastic human | 903+/−64 | 114+/−33 | 941+/−178 | 0+/−0 |
| murIL3 | 6000+/−565 | 6000+/−565 | not done | not done |

EXAMPLE 6

Mpl ligand stimulates 1A6.1 cell growth and human megakaryocyte development

Figure 3:
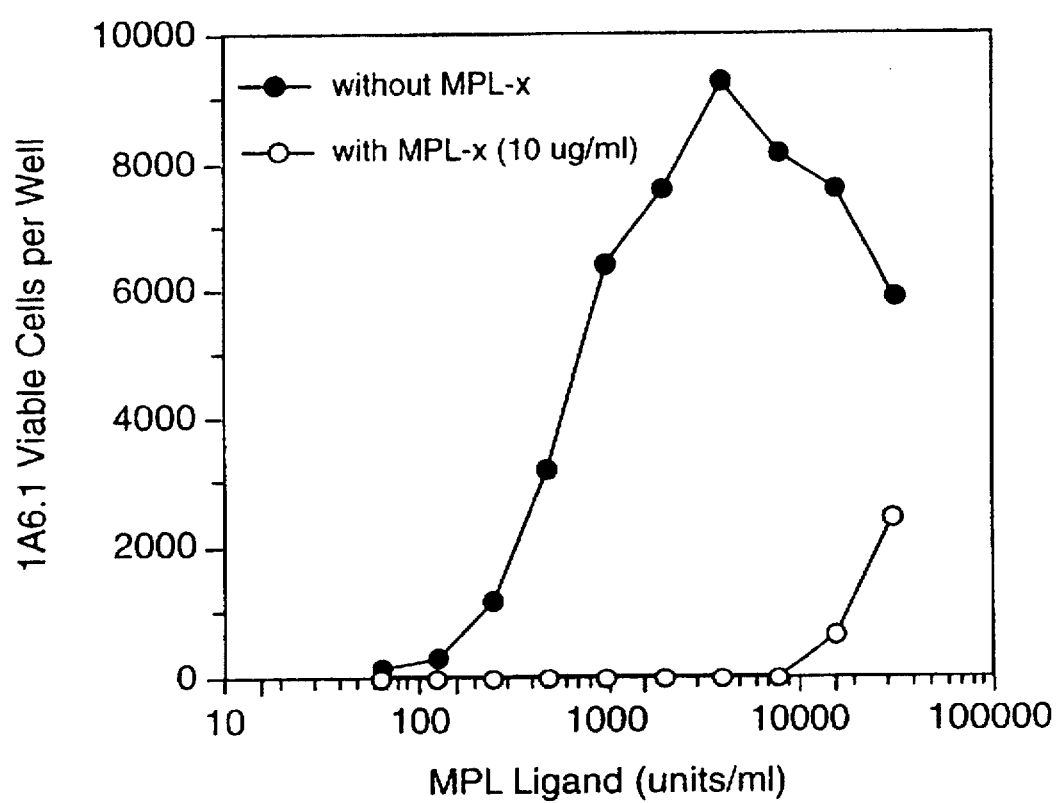
FIG. 3 shows that an activity enriched from APK9 by lectin affinity and Mpl receptor affinity chromatography procedures ("Mpl ligand") stimulates the growth of 1A6.1 cells and that soluble murine Mpl receptor blocks that growth.

Mpl ligand (enriched at least about 100,000-fold after lectin and affinity chromatography procedures; see Example 7) stimulates the growth of the 1A6.1 cell line and the development of human megakaryocytes from CD34-selected peripheral blood cells in a dose-dependent manner. The activity responsible is due to Mpl ligand as shown in FIGS. 2 and 3 since the activities in both assays can be completely blocked with Mpl-X.

It has also been shown by the inventors that FACS purified peripheral blood CD34$^+$ cells, when incubated in Mpl ligand (100 units/ml for 9 days in this case), develop into phenotypically normal, mature megakaryocytes. This establishes that purified Mpl ligand has the same effect on megakaryocytes as does crude APK9. Furthermore, this experiment used purified CD34$^+$ cells (100% CD34$^+$) as opposed to CD34-selected cells which are generally only 30–50% CD34$^+$.

EXAMPLE 7

Purification of Canine Mpl Ligand

I. Summary

Figure 4:
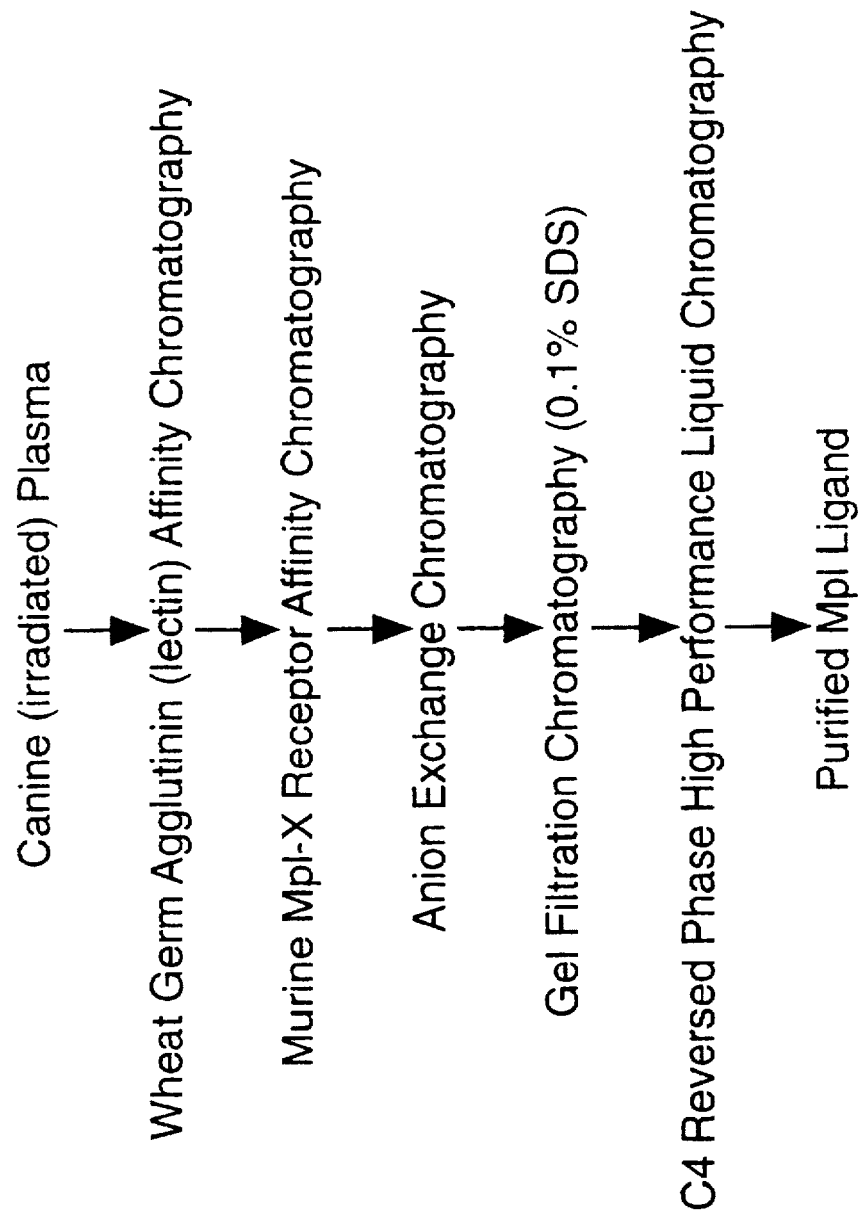
FIG. 4 shows an overview of the purification steps involved in purifying the 25 and 31 kd forms of the canine Mpl receptor from aplastic canine plasma.

Proteins (25 kd and 31 kd) that display activities predicted for a ligand for the Mpl receptor were purified. The proteins were purified from the plasma of irradiated dogs by a scheme employing wheat germ agglutinin (WGA) affinity chromatography, Mpl receptor affinity chromatography, anion exchange chromatography, gel filtration chromatography, and C4 reversed phase HPLC. See, FIG. 4 for an overview of this purification scheme. The 25 kd and 31 kd Mpl ligands have been highly purified to apparent homogeneity and have been determined to contain the amino acid sequences disclosed herein.

II. Methods

A. Clarification of plasma.

Frozen plasma (a total of 20 liters) from irradiated dogs (see Example 1) was thawed overnight at 4° C.; thawing of larger bottles was initiated at room temperature for several hours before placement in the cold room. Insoluble material was removed by centrifugation for 6 hours at 11,000×g. The plasma was diluted with phosphate buffered saline, pH 7.3, containing 0.01% sodium azide (PBS/azide) and filtered through a 1.2 μm filter. The clarification procedure typically resulted in an approximate two-fold dilution of the starting material.

B. Wheat Germ Agglutinin Affinity Chromatography.

All operations were carried out at 4° C. The clarified plasma (in two batches) was applied to a column of immobilized wheat germ agglutinin (1 liter, 10×12 cm, E Y Laboratories), equilibrated in PBS/azide. After sample application, unbound material was washed from the column with PBS/azide, followed by a wash with 0.5M NaCl in 20 mM Tris-HCl, pH 8. Mpl ligand activity, bound by the WGA column, was eluted with 0.35M N-acetylglucosamine (GlcNAc), 0.5M NaCl, 20 mM Tris-HCl, pH 8. Mpl ligand activity could not be detected in the flow through or wash fractions.

C. Mpl-X receptor affinity chromatography.

The soluble murine Mpl receptor (Mpl-X) that was used corresponded to the entire extracellular domain of the Mpl receptor minus Trp at position 483 (See Vigon, et al, *i* 8: 2607–2615 (1993)). In order to optimize binding of Mpl ligand to the Mpl-X receptor affinity column, the WGA elution pool was concentrated using a membrane ultrafilter (10,000 molecular weight cut off, YM-10, Amicon) and NaCl adjusted to 0.2M by subsequent dilution. The concentrated WGA pool was applied to a 20 ml m-Mpl-X (murine Mpl soluble receptor)/CNBr activated Sepharose column (2.6×4.2 cm, 1.5 mg m-Mpl-X per ml of resin) at a flow rate 0.9 ml/min. The column was washed with 40 ml of PBS/azide at 1.5 ml/min, followed by a high salt wash (405 ml)

with 10 mM Tris-HCl, 1M NaCl, 1 mM CHAPS, pH 8.0. The column was then eluted with 20 mM CAPS, 1M NaCl, 5 mM CHAPS, pH 10.5. Appropriate fractions were collected. Tris was added to each fraction to neutralize the pH.

Both the SDS-PAGE and the absorbance at 280 nm of the elution profile of an Mpl-X receptor affinity column reveal an early protein peak in fractions 1–4, while the majority of the Mpl ligand activity eluted after fraction 5.

D. Mono-Q Anion exchange chromatography.

The highest purity fractions from several Mpl-X receptor affinity columns were combined, concentrated, and diafiltered against 20 mM Tris-HCl, 5 mM CHAPS, pH 8.7 to a final volume of 58.5 ml. The protein concentration of the pool was estimated by absorbance at 280 nm to be 0.12 mg/ml (approximately 7 mg total protein). The pool was loaded at 0.5 ml/min onto a Mono Q HR 5/5 column (Pharmacia) equilibrated in 20 mM Tris-HCl, 5 mM CHAPS, pH 8.7. The column was eluted with a linear gradient to 0.36M NaCl in the same buffer over 27 minutes. The column was then washed with a 6 minute gradient to 0.54M NaCl, and finally with a step wash at 0.9M NaCl. One ml fractions were collected.

The elution profile of the Mono Q column shows that no Mpl ligand, and negligible protein, could be detected in the flow-through and wash fractions. Much of the Mpl ligand activity elutes in fractions 5–7, during the initial stages of the NaCl gradient. A "shoulder" of activity is observed in fractions 8–10, followed by a second major peak comprising fractions 11–15.

A distinct 25 kd band is observed by SDS-PAGE (nonreducing) in the active fractions. The intensity of the band directly corresponds with the Mpl ligand activity in the fractions. The band was absent in fractions 3 and 4 (no activity). It was prominent in fractions 5 and 6 (1A6.1 activity peak) and a similar, intensely stained band, was present in fractions 11–14 (1A6.1 activity peak). The band is faint in the pool of fractions 15 and 16, corresponding with the significantly lower activity in fraction 16.

E. Gel Elution Experiments.

Gel elution experiments were performed using aliquots of Mono Q fractions 5 and 6 or Mono Q fractions 13 and 14. For these experiments, pools of fractions 5 and 6 (6 µl each) or 13 and 14 (7.5 µl each) were made, mixed with SDS-PAGE sample buffer (nonreducing), and applied to 12% SDS gels. Upon completion of electrophoresis, lanes of interest were sliced (1 mm) and the slices were diced into small pieces with razor blades. The pieces were transferred to 1.5 ml microfuge tubes containing 0.5 ml PBS/5mM CHAPS and gently agitated overnight at 4° C. The next day the tubes were spun briefly, an aliquot was removed, and the sample was diafiltered against Iscove's medium supplemented with BSA as a carrier protein. The diafiltered samples were submitted for assay.

The results reveal that two peaks of Mpl ligand activity can be observed. One peak corresponds to the 25 kd region of the gel, while a second peak of Mpl ligand activity is observed in the 31 kd region.

F. Superdex 200 Gel Filtration.

Fractions 13–16 from the Mono Q anion exchange column, as well as two equivalent fractions from a second Mono Q fractionation, were combined and concentrated using a membrane ultrafilter (Centricon-10, Amicon). SDS was added to a final concentration of 0.1%, and the sample was injected onto a Superdex 200 HR 10/30 (Pharmacia) column. The column was equilibrated in 50 mM Tris-HCl, 0.1% SDS, pH 7.5 at a flow rate of 0.3 ml/min, and was operated at room temperature. One minute fractions were collected. The results were that most of the protein in the sample elutes in fractions 32–40, while the Mpl ligand activity is detected in fractions 42–46. Analysis of fractions SDS-PAGE showed a distinct 25 kd band in the active fractions.

G. C4 Reversed Phase HPLC.

Figure 5A:
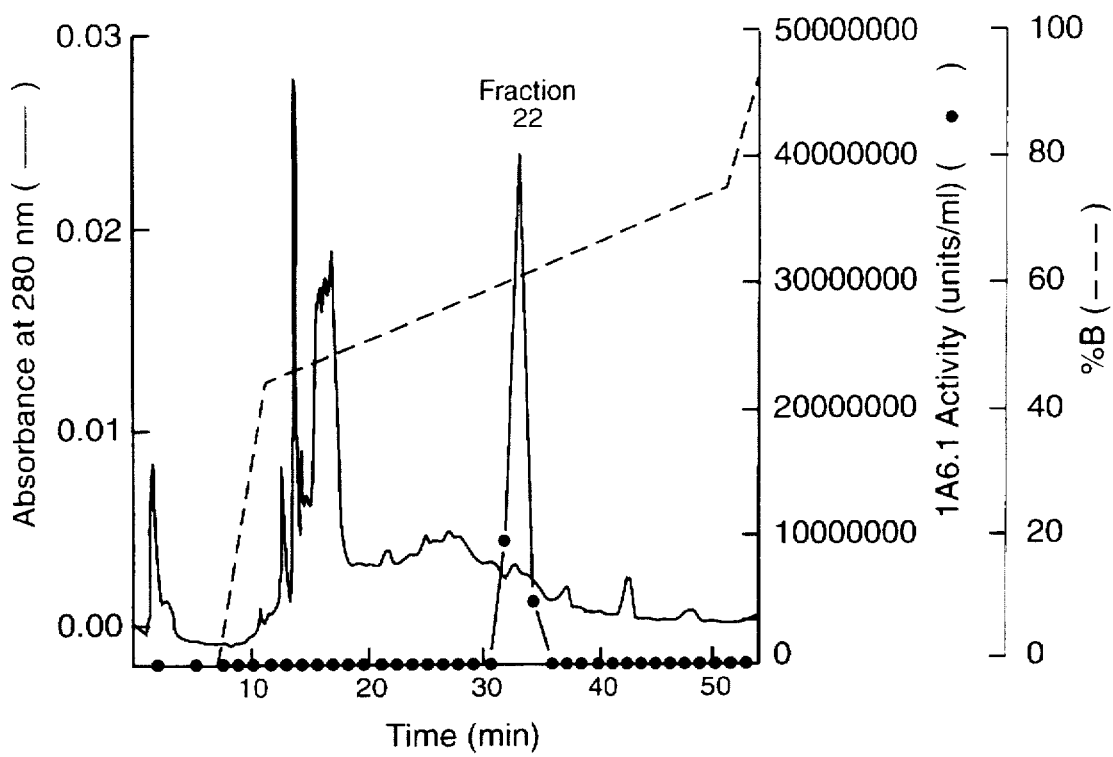
FIG. 5A shows the purification of Mpl ligand by reversed phase HPLC (RP-HPLC).
Figure 5B:
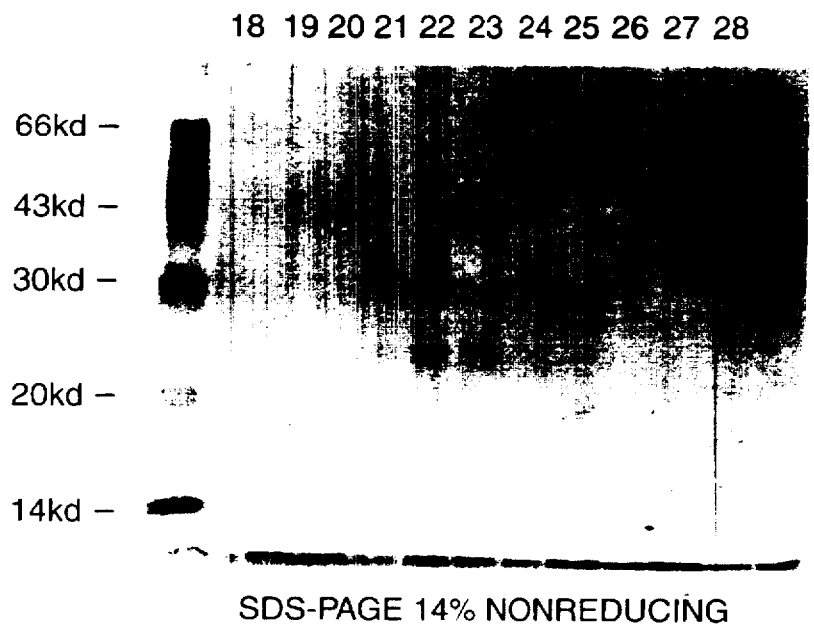
FIG. 5B shows that fraction 21 from the RP-HPLC contains highly purified 31 kd Mpl ligand; fraction 22 contains a mixture of the 31 kd and 25 kd Mpl ligands; and fraction 23 contains highly purified 25 kd Mpl ligand.

Superdex 200 fractions 43–46 combined or fraction 42 alone were concentrated using a membrane ultrafilter (Microcon-10, Amicon). The concentrated pools were separately applied to a 1×100 mm C4 reversed phase microbore column (SynChropak RP-4). The column was equilibrated in 0.04% TFA in water (A Buffer); B Buffer was 0.035% TFA in 80% acetonitrile. After injection of the sample, a linear gradient to 45% B over 4 min was performed, followed by a linear gradient to 75% B over 40 min. Flow rate was 75 µl/min. The results of purification of fraction 42 are presented in FIG. 5. Distinct Mpl ligand activity peaks were observed in fractions 21–23. These fractions were analyzed on a 14% polyacrylamide gel under nonreducing and reducing conditions. Fraction 21 was composed of a single 31 kd band; fraction 23 was composed of a single, broad 25 kd band; and fraction 22 contained bands in both the 25 kd and 31 kd regions. No other significant bands were visible. Note that earlier gel elution experiments had ascribed Mpl ligand activity to both of these regions. A single, minor high molecular weight band was observed in all fractions of the nonreducing gel, but could not be seen in the reducing gel.

H. N-terminal Sequence Analysis of 25 kd and 31 kd Mpl ligands.

N-terminal sequence analysis was carried out on C4 RP-HPLC fractions containing activity. The sequences determined for these proteins are reported above. In addition to the major sequence corresponding to the 25 kd band (at least 90% of the total of the applied sample), sequencing detected two minor sequences (which were associated with the minor contaminating band described in part G above). Comparisons with known sequences revealed that the minor sequences were canine Ig heavy chain and kappa chain. If desired, these minor impurities could be further reduced in quantity by application of another purification step, such as preferably another gel filtration step.

I. Comparison of Mpl ligand activities in the C4 purified fractions

Figure 6:
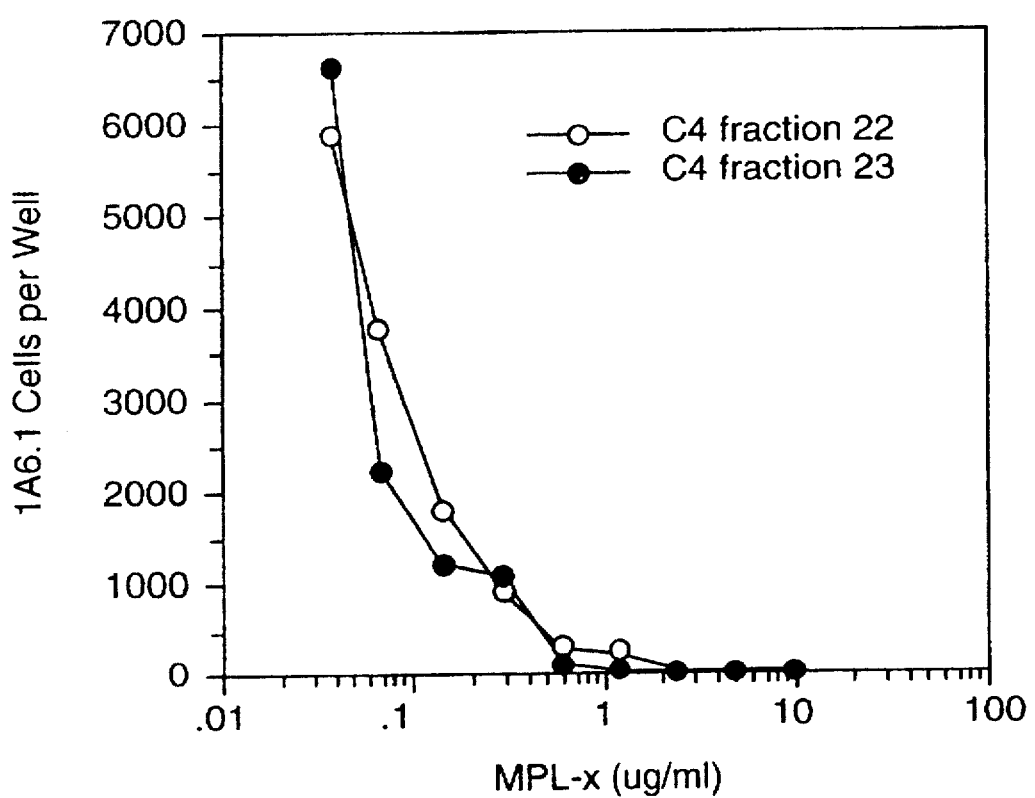
FIG. 6 shows a comparison of Mpl ligand activities in reverse phase HPLC (C4 column) fractions that contain the 25 and/or 31 kd Mpl ligand proteins.

FIG. 6 shows data demonstrating that the activities present in fractions 22 and 23 from the C4 RP-HPLC chromatography step are substantially equivalent. Fraction 22 contained a mixture of the 25 and 31 kd bands, whereas fraction 23 contained only the 25 kd band. Aliquots of each fraction were diluted 1:45000. The diluted fractions stimulated 1A6.1 cell growth substantially equally, (fraction 22, 5400 cells per well; fraction 23, 6000 cells per well). The diluted fractions were incubated with increasing concentrations of Mpl-X. The fractions were equally sensitive to inhibition by Mpl-X, both being completely blocked with 7–1.4 ug/ml. This indicates that the active protein(s) in each fraction are Mpl ligand species with equivalent biological activity.

EXAMPLE 8

Comparison of Mpl ligand to other factors on megakaryocyte development

A number of recombinant factors or organic compounds such as phorbol myristic acetate (PMA) have been reported to impact megakaryocyte growth or development. Accordingly, the effects of these factors on CD34-selected peripheral blood cells were investigated. Human recombinant interleukin 3 (IL-3, 1-2 ng/ml), stem cell factor (SCF, 50 ng/ml), interleukin 6 (IL-6, 25 ng/ml), erythropoietin (EPO, 1 Unit/ml), leukemia inhibitory factor (LIF, 10 ng/ml), and granulocyte-macrophage colony-stimulating factor (GM-CSF, 25 ng/ml, Amgen, Inc.); interleukin 11 (IL-11, 25 ng/ml, R+D Systems, Minneapolis, Minn.); phorbol myristic acetate (PMA, $10^{-10}$M, Sigma) were added to cultures as indicated. Mpl ligand was used at 275 units per ml, APK9 was used at 5% (equivalent to 220 units/ml). Factors tested in combination were at the same concentration as when tested individually. After 8 days in culture, the cells were fixed directly in the wells and stained for megakaryocytes (n=6 wells per condition) or counted for total cell number (n=3 wells per condition). Data are presented as mean ± SEM.

Figure 7:
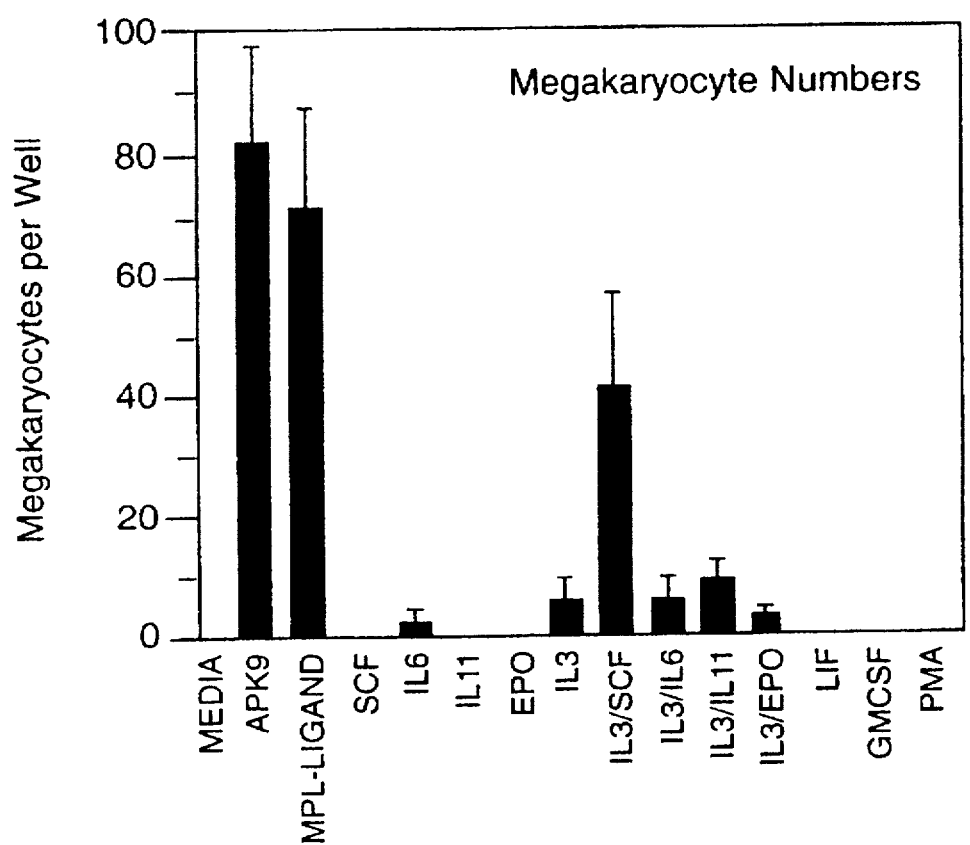
FIG. 7 shows the number of megakaryocytes produced from cultures of CD34-selected peripheral blood cells stimulated with APK9, Mpl ligand and various other factors.
Figure 8:
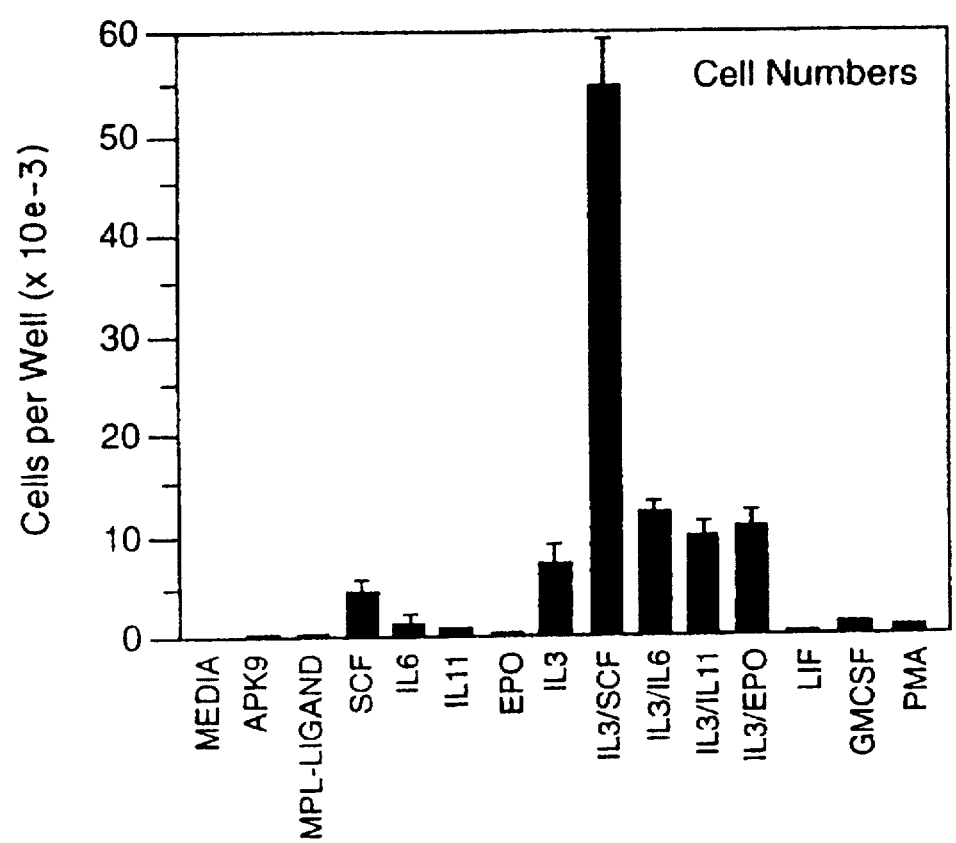
FIG. 8 shows the number of total leukocytes produced from cultures of CD34-selected peripheral blood cells stimulated with APK9, Mpl ligand and various other factors.
Figure 9:
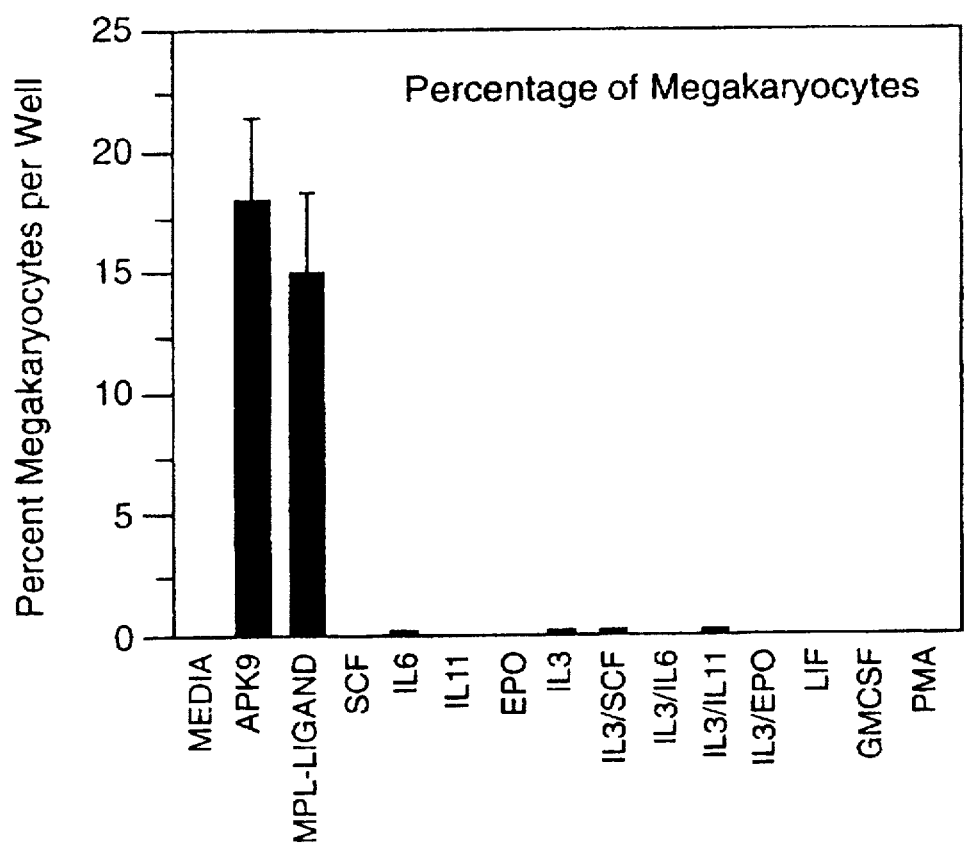
FIG. 9 shows the percentages of megakaryocytes that are produced in cultures of CD34-selected peripheral blood cells stimulated with APK9, Mpl ligand and various other factors.

FIG. 7 shows that APK9 and Mpl ligand resulted in the greatest number of megakaryocytes per well. IL-3 also resulted in megakaryocyte development, especially in combination with SCF. IL-6, IL-11, or EPO had little effect on megakaryocyte numbers either alone or in combination with IL-3. PMA, LIF and GM-CSF had little effect. In FIG. 8 are data from the same experiment showing the total number of cells found per well ("cellularity"). APK9 and Mpl ligand had little effect on cellularity while IL-3 and SCF had modest effects. SCF and IL-3 in combination had the greatest effects. The data shown in FIGS. 7 and 8 were used to calculate percentages of megakaryocytes per well, as shown in FIG. 9. Clearly, the factor which results in the greatest percentage of megakaryocytes per culture well is Mpl ligand, the active ingredient in APK9. This is indicative of the specificity of Mpl ligand towards megakaryocytes.

EXAMPLE 9

The megakaryocyte promoting activity of Mpl ligand is not dependent on human IL-3

Figure 10:
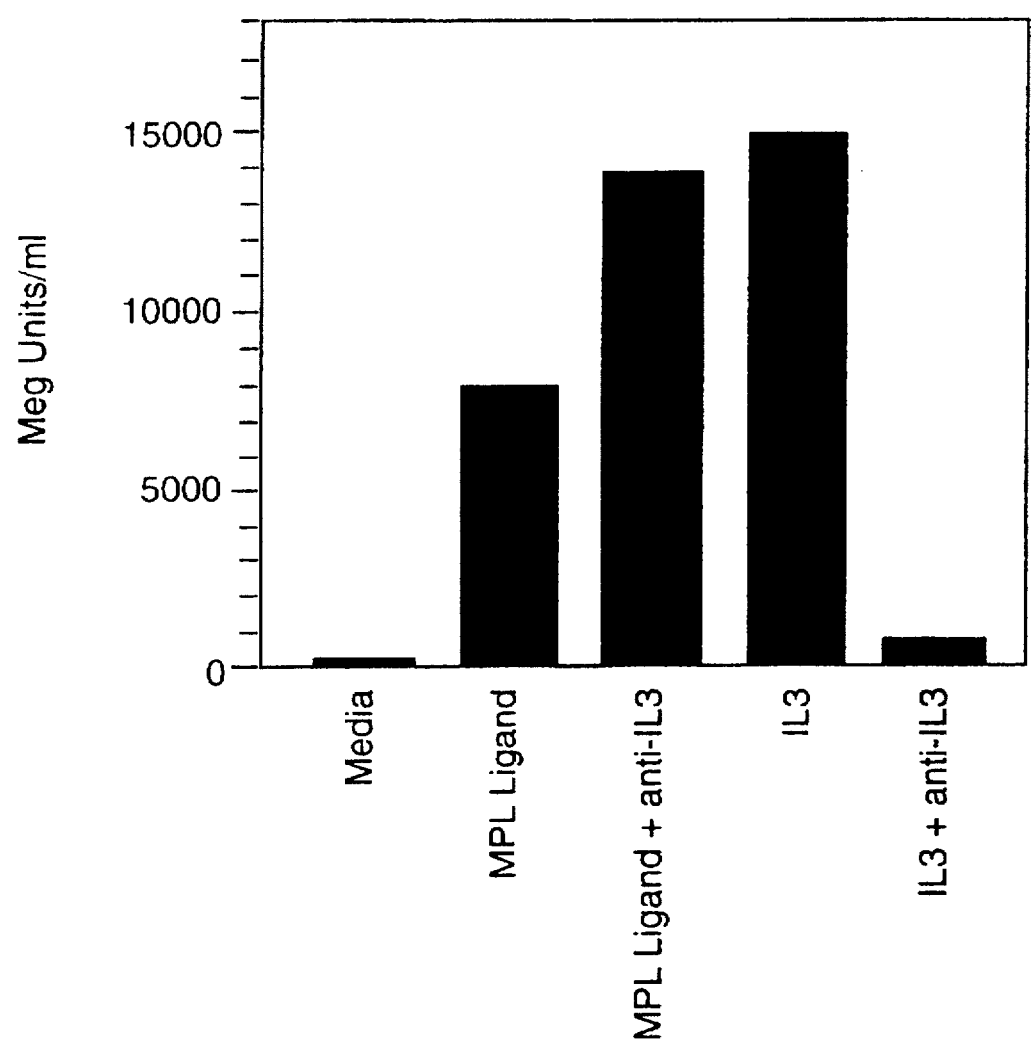
FIG. 10 shows that human IL-3 is not involved in Mpl ligand-induced megakaryocyte development.

Mpl ligand stimulates the development of human megakaryocytes when used as a supplement to the culture medium described in Example 2. Although IL-3 is not an ingredient of the medium, it could be present in undetectably low levels in the normal human plasma present in the medium. However, even if present, IL-3 is not involved in Mpl ligand-induced megakaryopoiesis. This is shown in FIG. 10. IL-3 at 2 ng/ml contains an activity in the human meg assay of 14,900 meg units/ml. This activity is 97% inhibited with anti-IL-3 (3.3 ug/ml; Genzyme, Cambridge, Mass.). MPL ligand at 8203 meg units/ml was not inhibited with anti-IL-3.

EXAMPLE 10

Analysis of porcine Mpl ligand

I. Summary

Proteins from irradiated pig plasma with Mpl ligand activity were characterized with WGA affinity chromatography, Mpl receptor affinity chromatography, ion exchange chromatography and C4 reverse phase HPLC. The activity was also characterized by elution from slices from SDS-polyacrylamide gels.

| Chromatography | Comments |
| --- | --- |
| WGA affinity column | 4.4 × $10^6$ units applied. |
| | 3.4 × $10^6$ units recovered |

-continued

| Chromatography | Comments |
| --- | --- |
| Mpl receptor column | 2.7 × $10^6$ units applied |
| | 2.4 × $10^6$ units recovered |
| Mono S ion exchange pH 6.0 | 2.4 × $10^6$ units applied |
| | 4.4 × $10^6$ units recovered |
| C4 reverse phase HPLC | Activity recovered fractions 23–25 |
| Gel elution Experiments | Two activities clearly distinguished, one at approximately 18 kd, the other at approximately 28 kd. |

EXAMPLE 11

Cloning of the Human Mpl-ligand, Human MGDF

Two approaches are outlined in the following:

I. First Exemplary Cloning Approach

A. Generation of human MDGF probe

A number of degenerate PCR primers were designed based on the amino terminus sequence of the canine protein. Different primer pairs were used to amplify the MGDF gene from the human genomic DNA. After 40 cycles of amplification, using the sense primers 5' GCN CCN CCN GCN TGY GA 3'(SEQ ID NO: 4), encoding the first five amino acids of the canine protein (SEQ ID NO: 1) and the antisense primer: 5' GCA RTG YAA CAC RTG NGA RTC 3'(SEQ ID NO: 5), encoding amino acids 16 to 21 of SEQ ID NO: 1, the PCR product was run on a 2.0% agarose gel in TBE buffer.

The 63 bp band was cut out from the agarose gel and reamplified using the same primer set. The PCR product was cloned in the PCR II vector (Invitrogen, San Diego). A number of colonies were screened by DNA sequencing. The plasmid DNA encoding a peptide similar to the canine MGDF protein was used as the source to generate a radioactive probe to screen the cDNA libraries. The amino acid sequence encoded by the gene fragment is as follows:

Ala-Pro-Pro-Ala-Cys-Asp-Leu-Arg-Val-Leu-Ser-Lys-Leu-Leu-Arg-Asp-Ser-His-Val-Leu-His (SEQ ID NO: 6)

The agarose band containing the human MGDF was used to generate the probe by hot PCR. A typical PCR reaction of 100 μl contained the following ingredients:

| | |
| --- | --- |
| template DNA | 2–3 μl |
| 5' primer (SEQ ID NO:4) | 1 μl, 20 pmoles |
| 3' primer (SEQ ID NO:5) | 1 μl, 20 pmoles |
| 10 X buffer | 10 μl |
| dATP (0.1 mM) | 2 μl |
| dTTP (10 mM) | 2 μl |
| dGTP (10 mM) | 2 μl |
| dCTP (0.1 mM) | 2 μl |
| dCTP, $p^{32}$ (10 uC/ul) | 5 μl |
| dATP, $p^{32}$ (10 uC/ul) | 5 μl |
| Taq DNA polymerase | 0.5 μl, 2.5 units |
| water | 77 μl |
| total volume | 100 μl |

The amplification conditions were as follows initial heating 94° C., 2 min anneal 53° C., 30 sec extension 72° C., 30 sec denaturation 94° C., 30 sec.

40 cycles of amplification was carried out in a Perkin Elmer GeneAmp System 9600.

The product was purified by passing through a push column (Stratagene, San Diego). One 1 µl of the probe was counted in a scintillation counter. Probes containing 1 to 3 million counts per ml were added to the hybridization mix.

B. Construction of fetal liver library

Human fetal liver polyA⁺ RNA was purchased from Clontech laboratories. About 4 µg of RNA was used for cDNA synthesis, in which priming was carried out using a random hexamer, 5' GTA CGC GTT CTA GAN NNN NNT 3', (SEQ ID NO: 7) attached to an oligo containing an Xba I site.

The Gibco-BRL protocol was used to generate the double stranded cDNA. The Eco R I-Bst X I adaptor (Invitrogen, San Diego) was ligated to the double stranded cDNA, followed by digestion with the restriction enzyme, Xba I. Size selection of the cDNA was carried out on a S500 Sephacryl column (Life Technologies, Inc.). cDNAs larger than 400 bp were ligated to the mammalian expression vector v19.8 (Martin, F., *Cell* 63: 203–211 (1990)) which was already digested with Eco RI and Xba I. Competent *E. coli* DH10 cells were transformed and the resulting cDNA library was split into 7 pools of 100,000 cDNA each.

C. Screening the lambda library

A human fetal kidney library in lambda gt11 was bought from Clontech with a titer of 650 million pfu/ml. About 2 million plaques were screened with a probe generated by PCR (see above). Hybridization was done in 6×SSC, 5×Denhardt, 0.1% SDS, 100 µg/ml single strand salmon sperm DNA for 15 hours at 56° C.

Multiple rounds of screening were carried out. DNA was amplified from single plaques and hybridized with the internal primer 5' AGT TTA CTG AGG ACT CGG AGG 3'(SEQ ID NO: 8) encoding amino acids 7 to 13 in SEQ ID NO: 6 to identify the true positives.

D. 3 prime Rapid Amplification of cDNA Ends (RACE)

Polyadenylated RNA from human fetal kidney and fetal liver were bought from Clontech. One microgram RNA was reverse transcribed using the oligo 5' TTC GGC CGG ATA GGC CTT TTT TTT TTT TTT 3'(SEQ ID NO: 9) as the primer.

The Gibco-BRL cDNA synthesis kit (Life Technologies Inc., Cat. #18267-013) was used to generate the first strand cDNA. The final volume was 30 µl. The reaction was stopped by adding 500 mM EDTA to a final concentration of 10 mM and kept at −20° C.

For initial PCR, 0.5 µl of cDNA was used as the template per reaction. The primer SEQ ID NO: 9 and the competitor oligo 5' TTC GGC CGG ATA GGC CTT TTT TTT TTT TT-P 3'(SEQ ID NO: 10) were used as the antisense primers, while the oligonucleotide 5' TGC GAC CTC CGA GTC CTC AG 3'(SEQ ID NO: 11) encoding amino acids 5 to 11 of SEQ ID NO: 6, was used as the sense primer. Forty cycles of amplification were carried out using the following protocol: 94° C., 30 sec; 65° C., 30 sec; 72° C., 30 sec. after an initial 2 min incubation at 94° C. A Perkin Elmer GeneAmp System 9600 was used for amplification.

Nesting was carried out using the sense primer 5' GAG TCC TCA GTA AAC TGC TTC GT 3'(SEQ ID NO: 12) encoding amino acids 8 to 14 of SEQ ID NO: 6, while SEQ ID NO: 9 and SEQ ID NO: 10 served as the antisense primers. Forty cycles of amplification were carried out with annealing at 65° C. The PCR products were run on a 0.8% agarose gel and then photographed under UV light. Bands around 0.8 to 1.2 kb were visible.

The PCR products were then cloned in the vector PCR II (Invitrogen). Individual colonies were picked and plasmids were isolated using the Qiagen kits cat #12143 and 12145. Double stranded dye primed sequencing was done using the vector primers. The sequences were analyzed by various types of GCG software.

E. 5' and 3' primer extension

In order to isolate the sequence of the full length MGDF gene, 3' and 5' primer extensions were carried out using different pools of fetal liver library as the template. For the amplification of the 5 primer of the cDNA, about 20 ng of cDNA from each pool was used as the template. A MGDF specific antisense primer 5' GGA GTC ACG AAG CAG TTT AC 3'(SEQ ID NO: 13) encoding amino acids 12 to 17 of SEQ ID NO: 6 and the 5' vector v19.8 sense primer 5' CCT TTA CTT CTA GGC CTG 3'(SEQ ID NO: 14) were used. Amplification was carried out for 30 cycles with annealing at 53° C. Nesting was done for 30 cycles with the antisense primers 5' GAG GTC ACA AGC AGG AGG A 3'(SEQ ID NO: 15) encoding amino acids 1 to 6 of SEQ ID NO: 6 and the vector primer SEQ ID NO: 14.

For the primer extension of the 3' ends of the MGDF cDNAs, the antisense vector primer 5' GGC ATA GTC CGG GAC GTC G 3'(SEQ ID NO: 16) and the MGDF specific primer 5' TCC TCC TGC TTG TGA CCT C 3'(SEQ ID NO: 17) encoding amino acids 1 to 6 of SEQ ID NO: 6, were used. Amplification was carried out for 30 cycles with annealing at 58° C.

Nesting amplification for 30 cycles was done using the MGDF primer SEQ ID NO: 12 and the vector primer SEQ ID NO: 16. Specific bands appeared in pool numbers 1, 7 and 8, which were cloned in the PCR II vector. Purified plasmid DNA from single colonies was purified and sequenced.

F. Isolation of full length clones of human MGDF

Many of the initial clones lacked part of the amino terminus of MGDF, since part of the MGDF sequence was used for priming and nesting. Primer 5' CCA GGA AGG ATT CAG GGG A 3'(SEQ ID NO: 18), whose sequence was obtained from the 5 primer extension experiments as described above was used as the sense primer. The vector primer SEQ ID NO: 16 served as the antisense primer. 35 cycles of amplification was carried out with annealing at 58° C. MGDF specific primer 5' CAA CAA GTC GAC CGC CAG CCA GAC ACC CCG 3'(SEQ ID NO: 19) with a Sal I site and the vector primer (SEQ ID NO: 15) were used for nesting for 35 cycles. The PCR product was cloned in PCR II vector and sequenced.

II. Second Exemplary Cloning Approach

A. Cloning Of Canine MGDF N-Terminus cDNA

Degenerate oligonucleotide primers were designed based on the canine MGDF N-terminus amino acid sequence described in the previous section and used as primers in polymerase chain reactions (PCRs) to amplify MGDF-encoding cDNA sequences. Total RNA was prepared from canine kidney samples by the guanidinium isothiocyanate method of Chomzynski and Sacchi (*Biochem.* 162: 156–159 (1987)). First strand cDNA was prepared with a random primer-adapter 5' GGC CGG ATA GGC CAC TCN NNN NNT 3' (SEQ ID NO: 20) using MoMULV reverse transcriptase and used as template in subsequent PCRs.

PCR was performed on 0.5 microliters, about 50 ng, of the cDNA, using Primer A 5' GCN CCN CCN GCN TGY GA 3' (SEQ ID NO: 4), a sense strand primer encoding amino acids 1–6 of SEQ ID NO: 1, and either primer B 5' GCA RTG NAG NAC RTG NGA RTC 3' (SEQ ID NO: 5) or primer C 5' GCA RTG YAA NAC RTG NGA RTC 3' (SEQ ID NO: 21), which are antisense strand primers encoding amino acids 16–21 of SEQ ID NO: 1 with three extra nucleotides at the 5' termini to increase annealing stability.

PCR with Taq polymerase was performed for 35 to 45 cycles, until product bands were apparent on agarose gel electrophoretic analysis. For the first two cycles of PCR, the reannealing step was performed at 37° C. for 2 minutes; for the remainder of the cycles reannealing was at 50° C. for 1 minute. Multiple product bands were observed in each reaction. Portions of the gel containing bands of approximately the expected size (66 bp) were collected with the tip of a Pasteur pipette and re-amplified with the same primer pair. The DNA products were cloned into vector PCR II (Invitrogen) according to the manufacturer's instructions. Three clones were sequenced and were found to encode, in one reading frame, the expected canine MGDF sequence, residues 1–21. In this way unique canine MGDF cDNA sequence was obtained spanning the region from the third nucleotide of codon 6 through the third nucleotide of codon 15. One of these clones served as the template for preparation of a labeled canine MGDF cDNA probe.

B. Construction of cDNA library from human fetal liver

RNA has been isolated from human fetal Liver (International Institute for the Advancement of Medicine, Exton, Pa.) by lysis of tissue in 5.5M guanidinium thiocyanate and purification via CsTFA (Pharmacia) centrifugation. Polyadenylated RNA was selected using oligo $(dT)_{25}$ dynabeads (Dynal, according to manufactures instruction). Double stranded cDNA was produced from this RNA using Superscript plasmid system for cDNA synthesis (Life Technologies, Inc.) except a different linker adapter: 5' TTG GTG TGC ACT TGT G 3' (SEQ ID NO: 22) and 5' CAC AAG TGC ACA CCA ACC CC 3'(SEQ ID NO: 23), was used. After size selection this cDNA was directionally inserted into the Bst XI and Not I sites of the mammalian expression vector pBCB (pBCB is derived from the plasmid Rc/CMV, Invitrogen, comprising the puc19 backbone, CMV promoter and BGH polyadenylation site). The ligated DNA was electroporated into electro competent bacterial strain 10B (Life Technologies, Inc.).

C. Screening of human fetal liver cDNA library for MGDF

Filter replicas of the human fetal liver library were hybridized to radioactively labeled canine MGDF N-terminus cDNA PCR product (5×SSPE, 2×Denhardt's, 0.05% Na pyrophosphate, 0.5% SDS, 100 µg/ml yeast tRNA lysate and 100 µg/ml denatured salmon sperm DNA) at 64° C. for 18 h. Filters were washed at 64° C. in 5×SSPE, 0.5% SDS and exposed over night. Two different clones hybridizing to this probe were isolated and analyzed.

D. Expression of human MGDF cDNA clones

Purified DNA from MGDF cDNA clones was transfected into 293 EBNA cells (Invitrogen). 1.5 µg of DNA was mixed with 7.5 ul Lipofectamine (Life Technologies, Inc.) in 100 ul of serum free DMEM. After a 20 minute incubation at room temperature the DNA-Lipofectamine mixture was added to $5\times10^5$ cells/well (24 well square Greiner plate) in 400 ul DMEM, 1% serum (Fetal Clone II) and incubated for 6 hours at 37° C. 500 ul DMEM, 20% serum (Fetal Clone II) was added to the cells. 16 hours later the media was aspirated and 500 ul DMEM, 1% serum (Fetal Clone II) was added. 72 hours later the conditioned media were collected and centrifuged through a 0.22 micron spin-filter. The conditioned media were assayed for MGDF biological activity.

III. Description and Activity of Human MGDF Clones

Based on the above-described cloning strategies, the human cDNA clones shown in FIG. 11 and FIG. 12 were obtained. Each of these sequences in the Figures contains a putative signal sequence of amino acids -21 to -1, so the mature proteins start at amino acid 1 in each case.

The results of activity assays using the cell-based assay described in Example 4A above with MGDFs 1–3 are presented in Tables 3 and 4 below. In Table 3, conditioned media from 293 EBNA cells transfected with each construct was collected after 2 days of culture then tested on 1A6.1 cells (32D/mur-MPL+) ±10 ug/ml mur-MPL-X. In Table 4, conditioned media from 293 EBNA cells transfected with each construct was collected after 4 days of culture then tested on both 32D/mur-MPL+ cells (Example 3A) and 32D/hu-MPL+ cells (Example 3B). As can be seen, human MGDF-1 (amino acids 1-332 of SEQ ID NO: 25) and MGDF-2 (amino acids 1-174 of SEQ ID NO: 25) but not MGDF-3 (amino acids 1-265 of SEQ ID NO: 27) were found to be active on cell lines expressing both the murine and human forms of Mpl. The cell line expressing the human MPL receptor is more responsive to human MGDF-1 (amino acids 1-332 of SEQ ID NO: 25) and MGDF-2 (amino acids 1-174 of SEQ ID NO; 25) than is the cell line expressing the murine Mpl receptor.

TABLE 3

| Clone | U/ml (−mur-MPL-X) | U/ml (+mur-MPLX) |
|---|---|---|
| Media | 0 | 0 |
| PBCO (control plasmid) | 0 | 0 |
| MGDF-1 (amino acids 1-332 of SEQ ID NO:25) | 12,800 | 800 |
| MGDF-1 12,800 (amino acids 1-332 of SEQ ID NO:25) (repeat) | 566 | |
| MGDF-2 (amino acids 1-174 of SEQ ID NO:25) | 4525 | 400 |
| MGDF-2 (amino acids 1-174 of SEQ ID NO:25) (repeat) | 12800 | 1131 |
| MGDF-3 (amino acids 1-265 of SEQ ID NO:27) | 0 | 0 |
| MGDF-3 (amino acids 1-265 of SEQ ID NO:27) (repeat) | 0 | 0 |
| APK9 control | 4400 +/− 400 | 0 |

TABLE 4

| Clone | U/ml 32D/mur-MPL+ | U/ml 32D/hu-MPL+ |
|---|---|---|
| MGDF-1 (amino acids 1-332 of SEQ ID NO:25) | 1600 | 25,600 |
| MGDF-2 (amino acids 1-174 of (SEQ ID NO:25) | 6400 | 50,000 |
| MGDF-2 (amino acids 1-174 of (SEQ ID NO:25) (repeat) | 6400 | 50,000–100,000 |

The following Table 5 shows that the activities of human MGDF-1 (amino acids 1-332 of SEQ ID NO: 25) and MGDF-2 (amino acids 1-174 of SEQ ID NO: 25) on 32D/hu-MPL+ cells (Example 3B) are substantially completely inhibited by soluble human mpl receptor (hu-MPL-X). Hu-MPL-X was present as conditioned media collected from CHO cells producing the protein. The CHO hu-MPL-X conditioned media was concentrated 120-times then added to the cultures at 6.6%. Conditioned media from control CHO cultures had no effect on the assay. The assay was carried out as described in Example 4B except that the viable cells were assessed after 3 days.

TABLE 5

| Clone | U/ml (−Hu-MPL-X) | U/ml (+Hu-MPL-X) |
|---|---|---|
| MGDF-1 (amino acids 1-332 of SEQ ID NO:25) | 530 | 0 |
| MGDF-2 (amino acids 1-332 of SEQ ID NO:25) | 270 | 0 |

Human Megakaryocyte Assay

MGDF-1 (amino acids 1-332 of SEQ ID NO: 25) and MGDF-2 (amino acids 1-174 of SEQ ID NO: 25) but not MGDF-3 (amino acids 1-265 of SEQ ID NO: 27) induced the formation of megakaryocytes from peripheral blood CD34-selected cells. The experiment described in Table 6 was performed essentially as described in Example 2 except that peripheral blood cells were CD34-selected without elutriation and the culture was harvested after 7 days. Conditioned media from each 293 EBNA MGDF construct was used at 20% final volume ±30 µg/ml mur-MPL-X. APK9 control was used at 6% final volume.

TABLE 6

| Clone | Megakaryocytes per Well (−mur-MPL-X) | Megakaryocytes per Well (+mur-MPL-X) |
|---|---|---|
| vector control | 0 | 0 |
| APK9 control | 100 +/− 3 | 0 |
| MGDF-1 (amino acids 1-332 of SEQ ID NO:25) | 142 +/− 48 | 17 +/− 2 |
| MGDF-2 (amino acids 1-174 of SEQ ID NO:25) | 100 +/− 3 | 6 +/− 2 |
| MGDF-2 (amino acids 1-174 of SEQ ID NO:25) repeat | 86 +/− 10 | 0 |
| MGDF-3A (amino acids 1-265 of SEQ ID NO:27) | 2 +/− 2 | 0 |

EXAMPLE 12

The following example describes the synthesis of 12 different pegylated MGDF molecules, PEG 9–PEG 12 and PEG 14–PEG 21. In each case, the MGDF molecule that was pegylated was *E. coli* derived MGDF-11 (amino acids 1-163 of SEQ ID NO: 25) (amino acids 1-163, numbering from the beginning of the mature protein). Details regarding all of these pegylated species are summarized in Tables 7–10 below.

12.1 Preparation of poly-MePEG-MGDF conjugates by MGDF acylation with activated MePEG derivatives Preparation of poly-MePEG(20 kDa)-MGDF conjugate (PEG 11).

A cooled (4° C.) solution of MGDF (2.5 mg/ml) in 0.1M BICINE buffer, pH 8, was added to a 10-fold molar excess of solid MePEG succinimidyl propionate (MW 20 kDa) (Shearwater Polymers, Inc.). The polymer was dissolved by gentle stirring and the reaction further conducted at room temperature.

The extent of the protein modification during the course of the reaction was monitored by size exclusion (SEC) HPLC using Superdex 200 HR 10/30 column (Pharmacia Biotech) eluted with 0.1M sodium phosphate buffer pH 6.9 at 0.7 ml/min.

SEC HPLC analysis of the reaction mixture at the 30 minute time point indicated that no free protein was left in the reaction mixture. At this point the protein concentration in the reaction mixture was reduced to 1 mg/ml by addition of sterile water and the pH of the mixture adjusted to 4 with several drops of 0.5M acetic acid.

MePEG-MGDF conjugate was separated from the excess of MePEG and other reaction by-products by ion-exchange chromatography using SP Sepharose HP (Pharmacia Biotech) ion exchange resin.

The reaction mixture was loaded (2.5 mg/ml of resin) onto the column and the unreacted MePEG was eluted with 3 column volumes of the starting buffer A (20 mM sodium phosphate, pH 7.2, 15% glycerol). After that, the MePEG-MGDF conjugate was eluted using a linear gradient from 0% to 30% in 10 column volumes of the end buffer B (1M NaCl in buffer A). The eluent was monitored at 280 nm. Fractions containing poly-MePEG-MGDF conjugate were pooled, concentrated and sterile filtered.

The purified poly-MePEG-MGDF conjugate was analyzed by HPLC SEC using TSK-GEL G4000SWXL and G2000SWXL gel filtration columns coupled in series. Proteins were detected by UV absorbance at 280 nm. BIO-RAD gel filtration standards served as globular protein molecular weight markers.

Figure 17A:
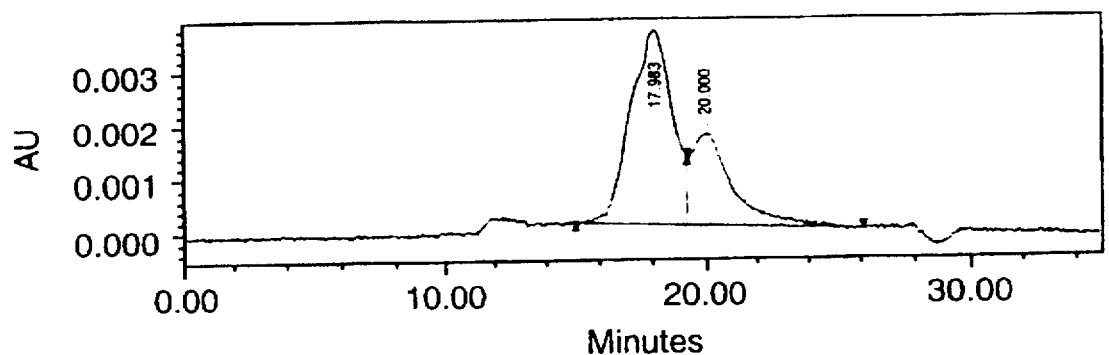
FIG. 17A shows size exclusion (SEC) HPLC analysis of poly-MePEG-MGDF conjugate prepared by MGDF acylation with the NHS ester of 20 kDa MePEG (PEG 11).

As can be seen in FIG. 17A, HPLC SEC reveals two major components in the preparation (in about a 2 to 1 ratio) elution positions of which correspond to those of 370.9 kDa and 155.0 kDa globular proteins respectively. See also Table 8 below.

Conjugates PEG 9, PEG 10 and PEG 12 prepared by MGDF acylation with succinimidyl esters of MW=6–50 kDa MePEGs were conducted similarly. The major reaction parameters used in these preparations are summarizable in Table 7.

Results of HPLC SEC analyses of these conjugates are shown in Table 8.

12.2. Preparation of poly-MePEG-MGDF conjugates by MGDF reductive alkylation with MePEG aldehydes Preparation of poly-MePEG(20 kDa)-MGDF conjugate (PEG 20).

To a cooled (4° C.), stirred solution of MGDF (2 ml, 2.5 mg/ml) in 100 mM sodium phosphate, pH 5, containing 20 mM NaCNBH3 was added a 10-fold molar excess of monomethoxy-polyethylene glycol aldehyde (MePEG) (average molecular weight 20 kDa) and the stirring of the reaction mixture was continued at the same temperature.

The extent of the protein modification during the course of the reaction was monitored by SEC HPLC using Superdex 200 HR 10/30 column (Pharmacia Biotech) eluted with 0.1M sodium phosphate buffer pH 6.9 at 0.7 ml/min.

After 16 hours the SEC HPLC analysis indicated that more than 90% of the initial amount of the protein has been modified. At this time the protein concentration in the reaction mixture was brought to 1 mg/ml by dilution of the reaction mixture with sterile water and the pH adjusted to 4 (0.5M acetic acid).

MePEG-MGDF conjugate was separated from the excess of MePEG and other reaction by-products by ion-exchange chromatography using SP Sepharose HP (Pharmacia Biotech) ion exchange resin.

The reaction mixture was loaded (2.5 mg/ml of resin) onto the column and the unreacted MePEG was eluted with 3 column volumes of the starting buffer A (20 mM sodium phosphate, pH 7.2, 15% glycerol). After that, the MePEG-MGDF conjugate was eluted using a linear gradient from 0% to 30% in 10 column volumes of the end buffer B (1M NaCl in buffer A). The eluent was monitored at 280 nm. Fractions containing poly-MePEG-MGDF conjugate were pooled, concentrated and sterile filtered.

The purified poly-MePEG-MGDF conjugate was analyzed by HPLC SEC using TSK-GEL G4000SWXL and G2000SWXL gel filtration columns coupled in series. Proteins were detected by UV absorbance at 280 nm. BIO-RAD gel filtration standards served as globular protein molecular weight markers.

Figure 17B:
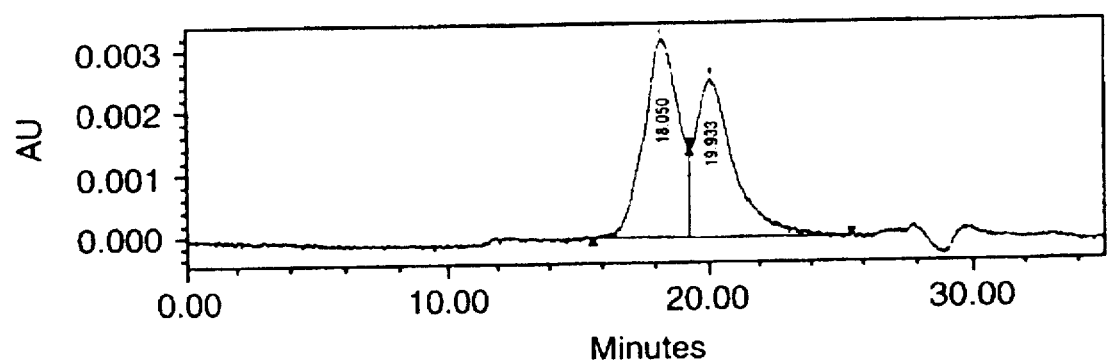
FIG. 17B shows SEC HPLC analysis of poly-MePEG-MGDF conjugate prepared by MGDF alkylation with 20 kDa MePEG aldehyde (PEG 20).

As can be seen in FIG. 17B, HPLC SEC reveals two major components (constituting 52% and 47% of the total amount) in the preparation, elution positions of which correspond to those of 359.4 kDa and 159.3 kDa globular proteins respectively. See also Table 8.

Conjugates PEG 18, PEG 19 and PEG 21 prepared by MGDF reductive alkylation with MePEG aldehydes of MW=6–25 kDa were conducted similarly. The major reaction parameters used in these preparations are summarized in Table 7.

Results of HPLC SEC analyses of these conjugates are shown in Table 8.

12.3. Preparation of monomethoxy-polyethylene glycol-MGDF conjugates with the site of attachment at the N-terminal α-amino residue Preparation of mono-MePEG (20 kDa)-MGDF conjugate (PEG 16)

To a cooled (4° C.), stirred solution of MGDF (2 ml, 2.5 mg/ml) in 100 mM sodium phosphate, pH 5, containing 20 mM NaCNBH3 was added a 5-fold molar excess of methoxypolyethylene glycol aldehyde (MePEG) (average molecular weight 20 kDa) and the stirring of the reaction mixture was continued at the same temperature.

The extent of the protein modification during the course of the reaction was monitored by SEC HPLC using Superdex 200 HR 10/30 column (Pharmacia Biotech) eluted with 0.1M sodium phosphate buffer pH 6.9 at 0.7 ml/min.

After 16 hours the SEC HPLC analysis indicated that about 90% of the initial amount of the protein has been modified. At this time the protein concentration in the reaction mixture was reduced to 1 mg/ml by dilution with sterile water and the pH of the reaction mixture adjusted to 4 (0.5M acetic acid).

The mono-MePEG (20 kDa)-MGDF conjugate was separated from the excess of MePEG and other reaction by-products by ion-exchange chromatography using SP Sepharose HP (Pharmacia Biotech) ion exchange resin.

The reaction mixture was loaded (2.5 mg/ml of resin) onto the column and the unreacted MePEG was eluted with 3 column volumes of the starting buffer A (20 mM sodium phosphate, pH 7.2, 15% glycerol). After that, the MePEG-MGDF conjugate was eluted using a linear gradient from 0% to 25% of the end buffer B (1M NaCl in buffer A) in 20 column volumes. The eluent was monitored at 280 nm. Fractions containing poly-MePEG-MGDF conjugate were pooled, concentrated and sterile filtered.

The homogeneity of the mono-MePEG-MGDF conjugates was determined by Sodium Dodecyl Sulfate Polyacrylamide Gel Electrophoresis using 4–20% precast gradient gels (NOVEX). One major band corresponding to the position of a 46.9 kDa protein was revealed.

The purified poly-MePEG-MGDF conjugate was analyzed by HPLC SEC using TSK-GEL G4000SWXL and G2000SWXL gel filtration columns coupled in series. Proteins were detected by UV absorbance at 280 nm. The BIO-RAD gel filtration standards served as globular protein molecular weight markers.

Figure 17C:
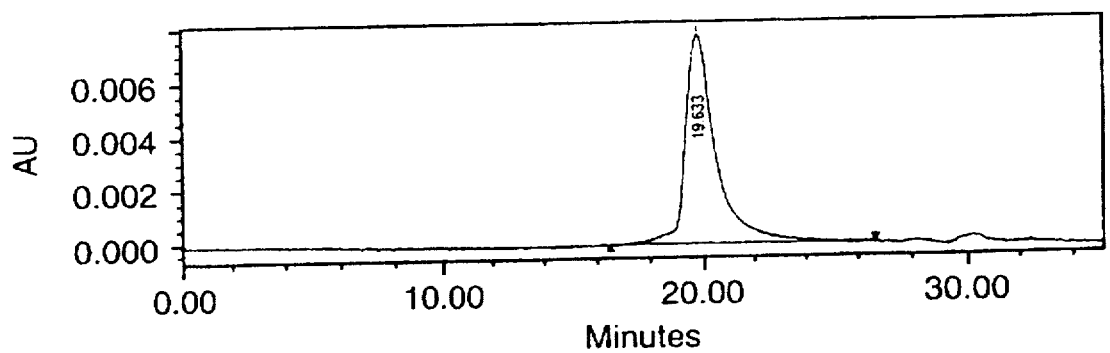
FIG. 17C shows SEC HPLC analysis of mono-MePEG-MGDF conjugate prepared by MGDF alkylation with MW 20 kDa MePEG aldehyde (PEG 16).

As can be seen in FIG. 17C, SEC HPLC reveals one major component in the preparation, elution positions of which corresponds to that of 181.1 kDa globular protein. See also Table 9.

Mono-MePEG-MGDF conjugates PEG 14, PEG 15 and PEG 17 prepared by MGDF reductive alkylation with MePEG aldehydes of MW=6–25 kDa were conducted similarly. The major reaction parameters used in these preparations are summarized in Table 7.

Results of HPLC SEC analyses of these conjugates are shown in Table 9.

TABLE 7

Summary of MGDF modification reaction parameters

| | | | | Reaction conditions | | | |
|---|---|---|---|---|---|---|---|
| Code | Reactive Type | MePEG MW | MGDF conc. mg/ml | pH | Temp-erature, °C | Time, h | Molar Ratio MePEG/MGDF |
| PEG 9 | NHS ester | 6kDa | 2.5 | 8 | r.t. | 0.5 | 15 |
| PEG 10 | NHS ester | 6kDa | 2.5 | 8 | r.t. | 0.5 | 10 |
| PEG 11 | NHS ester | 20kDa | 2.5 | 8 | r.t. | 0.5 | 10 |
| PEG 12 | NHS ester | 50kDa | 2.5 | 8 | r.t. | 0.5 | 5 |
| PEG 14 | ALDE-HYDE | 6 kDa | 2.5 | 5 | 4° C. | 16 | 5 |
| PEG 15 | ALDE-HYDE | 12kDa | 2.5 | 5 | 4° C. | 16 | 5 |
| PEG 16 | ALDE-HYDE | 20kDa | 2.5 | 5 | 4° C. | 16 | 5 |
| PEG 17 | ALDE-HYDE | 25kDa | 2.5 | 5 | 4° C. | 16 | 10 |
| PEG 18 | ALDE-HYDE | 6kDa | 5 | 5 | 4° C. | 16 | 10 |
| PEG 19 | ALDE-HYDE | 12kDa | 5 | 5 | 4° C. | 16 | 10 |
| PEG 20 | ALDE-HYDE | 20kDa | 5 | 5 | 4° C. | 16 | 10 |
| PEG 21 | ALDE-HYDE | 25kDa | 5 | 5 | 4° C. | 16 | 10 |

TABLE 8

Summary of poly-MePEG-MGDF characteristics by SEC HPLC

| Code | Reactive | MePEG | Apparent MW by SEC, kDa | Component amount, % |
|---|---|---|---|---|
| PEG 9 | NHS ester | 6kDa | 87.9 | 75 |
| | | | 52.7 | 25 (shoulder) |
| PEG 10 | NHS ester | 6kDa | 69.2 | 14 (shoulder) |
| | | | 42.9 | 86 |
| PEG 11 | NHS ester | 20kDa | 370.9 | 68 |
| | | | 155.0 | 32 |
| PEG 12 | NHS ester | 50kDa | 865.6 | 53 |
| | | | 368.0 | 47 |
| PEG 18 | ALDEHYDE | 6kDa | 84.6 | 60 |
| | | | 41.5 | 40 |
| PEG 19 | ALDEHYDE | 12kDa | 218.4 | 59 |

TABLE 8-continued

Summary of poly-MePEG-MGDF characteristics by SEC HPLC

| Code | Reactive | MePEG | Apparent MW by SEC, kDa | Component amount, % |
|---|---|---|---|---|
| | | | 106.7 | 41 |
| PEG 20 | ALDEHYDE | 20kDa | 359.4 | 52 |
| | | | 159.3 | 47 |
| PEG 21 | ALDEHYDE | 25kDa | 450.5 | 54 |
| | | | 218.4 | 46 |

TABLE 9

Apparent molecular weights of mono-MePEG-MGDF Conjugates

| Code | Reactive Type | MePEG MW | Apparent MW by SEC, kDa | Apparent MW by SDS PAGE, kDa |
|---|---|---|---|---|
| PEG 14 | ALDEHYDE | 6 kDa | 44.5 | 27.7 |
| PEG 15 | ALDEHYDE | 12kDa | 104.7 | 38.3 |
| PEG 16 | ALDEHYDE | 20kDa | 181.1 | 46.9 |
| PEG 17 | ALDEHYDE | 25kDa | 226.4 | 55.5 |

EXAMPLE 13

Biological Activity of Pegylated MGDF Molecules

Figure 18:
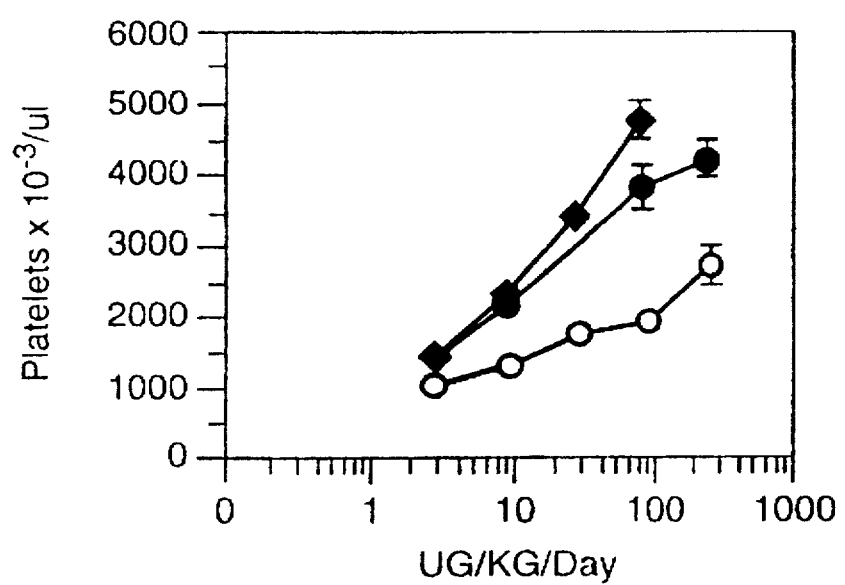
FIG. 18 shows platelet counts from mice treated with recombinant human MGDF: open diamond=CHO-derived 1-332 MGDF (MGDF-1; amino acids 1-332 of SEQ ID NO: 25) open circles=unpegylated *E. coli* 1-163 MGDF (MGDF-11; amino acids 1-163 of SEQ ID NO: 25) and closed circles=pegylated *E. coli* 1-163 MGDF (MGDF-11; amino acids 1-163 of SEQ ID NO: 25).

Platelet counts from mice treated with recombinant human MGDF were measured and the results are presented in FIG. 18. CHO-derived 1-332 MGDF (MGDF-1; amino acids 1-332 of SEQ ID NO: 25) (open diamond), unpegylated E. coli 1-63 MGDF (MGDF-11; amino acids 1-163 of SEQ ID NO: 25) (open circles) and pegylated E. coli 1-63 MGDF (MGDF-11; amino acids 1-163 of SEQ ID NO: 25) (closed circles) MGDF at the indicated concentrations were injected subcutaneously into normal Balb/c mice once daily for 5 days. Test bleeds from a small lateral cut in a tail vein were collected 24 hours after the last injection. Blood cell analyses were performed with a Sysmex electronic blood cell analyser (Baxter Diagnostics, Inc. Irvine, Calif.). Data are represented as the mean of determinations of 4 animals, ± standard error of the mean. Other blood cell parameters such as total white blood cell counts or red blood cell counts were not affected by this treatment.

Additional forms of recombinant human MGDF were tested as above. Platelet counts from mice treated with either 50 ug/kg/day or 10 ug/kg/day of the indicated form of r-HuMGDF are shown in the following Table 10. Data are the mean of 4 animals and the standard errors are italicized.

TABLE 10

| | 50 ug/kg/day | | 10 ug/kg/day | |
|---|---|---|---|---|
| Form | Mean (n = 4) | sem | Mean (n = 4) | sem |
| CHO MGOF-1 (amino acids 1-332 of SEQ ID NO:1) | 4343 | 309 | 2571 | 80 |
| E. Coli 22 184 | 2021 | 29 | 1439 | 18 |
| PEG 9 | 2728 | 56 | 2369 | 34 |

TABLE 10-continued

| | 50 ug/kg/day | | 10 ug/kg/day | |
|---|---|---|---|---|
| Form | Mean (n = 4) | sem | Mean (n = 4) | sem |
| PEG 10 | 2431 | 291 | 1556 | 126 |
| PEG 11 | 3778 | 59 | 1861 | 73 |
| PEG 12 | 3885 | 156 | 1740 | |
| PEG 14 | 3567 | 80 | 2020 | 63 |
| PEG 15 | 4402 | 57 | 2834 | 99 |
| PEG 16 | 4511 | 239 | 3215 | 11 |
| PEG 17 | 4140 | 188 | 3113 | 261 |
| PEG 18 | 4586 | 59 | 2931 | 129 |
| PEG 19 | 3980 | 330 | 4189 | 80 |
| PEG 20 | 3942 | 285 | 3054 | 339 |
| PEG 21 | 4195 | 145 | 4002 | 91 |
| Baseline | 939 | 25 | | |

Key to Table 10

In each of the following, the MGDF molecule that was pegylated was E. coli derived MGDF-11 (amino acids, numbering from the beginning of the mature protein), as described in the above Example 12:

| Name | Pegylation | Avg. MW of PEG | Reactive PEG molecule for synthesis |
|---|---|---|---|
| PEG 9 | polypegylated | 6 kDa | NHS ester of MePEG |
| PEG 10 | polypegylated | 6 kDa | NHS ester of MePEG |
| PEG 11 | polypegylated | 20 kDa | NHS ester of MePEG |
| PEG 12 | polypegylated | 50 kDa | NHS ester of MePEG |
| PEG 14 | monopegylated | 6 kDa | Aldehyde of MePEG |
| PEG 15 | monopegylated | 12 kDa | Aldehyde of MePEG |
| PEG 16 | monopegylated | 20 kDa | Aldehyde of MePEG |
| PEG 17 | monopegylated | 25 kDa | Aldehyde of MePEG |
| PEG 18 | polypegylated | 6 kDa | Aldehyde of MePEG |
| PEG 19 | polypegylated | 12 kDa | Aldehyde of MePEG |
| PEG 20 | polypegylated | 20 kDa | Aldehyde of MePEG |
| PEG 21 | polypegylated | 25 kDa | Aldehyde of MePEG |

The baseline counts are in normal animals without administration of any materials.

It is clear that pegylation of recombinant human MGDF does not adversely affect the ability of the molecule to increase platelet counts in recipient animals, and may in fact increase the activity of the E. coli product 1-63 MGDF (MGDF-11; amino acids 1-163 of SEQ ID NO: 25) to be as great or greater than that seen with the CHO-derived 1-332 MGDF (MGDF-1; amino acids 1-332 of SEQ ID NO: 25) molecule.

While the present invention has been described above both generally and in terms of preferred embodiments, it is understood that variations and modifications will occur to those skilled in the art in light of the above description. Therefore, it is intended that the appended claims cover all such variations coming within the scope of the invention as claimed.

Additionally, the publications and other materials cited to illuminate the background of the invention, and in particular cases to provide additional details concerning its practice, are herein incorporated by reference.

What is claimed is:

1. A polypeptide consisting of amino acids 1-163 of SEQ ID NO: 25, wherein a single polyethylene glycol is attached to the α-amino group at the N-terminus of said polypeptide.

2. A polypeptide according to claim 1, wherein said polyethylene glycol has an average molecular weight of 5 kDa to 50 kDa.

3. A polypeptide according to claim 1, produced by a process comprising the following steps:

a) reacting a polypeptide precursor consisting of amino acids 1-163 of SEQ ID NO:25 with a polyethylene glycol molecule having a single reactive aldehyde group under reductive alkylation conditions, at a pH sufficiently acidic to allow the α-amino group at the amino terminus of said polypeptide precursor to be reactive; and b) obtaining a monopegylated polypeptide product.

4. A polypeptide according to claim 3, wherein said reductive alkylation conditions involve the use of sodium cyanoborohydride as a reducing agent.

5. A substantially homogeneous preparation of a polypeptide consisting of amino acids 1-163 of SEQ ID NO: 25 monopegylated on the α-amino group at the N-terminus of said polypeptide.

6. A pharmaceutical composition comprising a polypeptide according to any of claims 1, 2, 3, 4, or 5 and a pharmaceutically acceptable diluent, adjuvant or carrier.

7. A pharmaceutical composition according to claim 6, comprising an aqueous solution.

8. A pharmaceutical composition according to claim 6, wherein said composition is in the form of a lyophilizate.

9. A pharmaceutical composition comprising:

(a) a substantially homogeneous preparation of a polypeptide consisting of amino acids 1-163 of SEQ ID NO:25 monopegylated on the α-amino group at the N-terminus of said polypeptide via an alkyl linkage, wherein the polyethylene glycol has a molecular weight of 5 kDa to 50 kDa; and (b) a pharmaceutically acceptable diluent, adjuvant or carrier.

10. A pharmaceutical composition according to claim 9, comprising an aqueous solution.

11. A pharmaceutical composition according to claim 10, wherein said composition is in the form of a lyophilizate.

* * * * *

UNITED STATES PATENT AND TRADEMARK OFFICE
CERTIFICATE OF CORRECTION

PATENT NO.   : 5,795,569
DATED        : August 18, 1998
INVENTOR(S)  : Bartley et al.

Page 1 of 1

It is certified that error appears in the above-identified patent and that said Letters Patent is hereby corrected as shown below:

Column 19,
Line 24, change ">95%" to -- $\geq$95% --.

Column 21,
Line 54, change "αa-amino" to -- α-amino --.

Column 22,
Line 52, delete the phrase "The working e".

Column 38,
Line 29, move "12,800" to the second column, line 29.
Line 29, move "556" to the third column, line 29.

Column 39,
Line 40, change "3A" to -- 3 --.

Column 43,
Line 57, change "MGOF" to -- MGDF --.
Line 60, change "*E. Coli* 22 184" to -- *E. coli* MGDF-11 (amino acids 1-163 of SEQ ID NO: 25) --.

Column 44,
Line 8, insert -- 88 -- in column 5.
Line 21, after the word "acids" and before "," insert -- 1-163 --.

Signed and Sealed this

Sixteenth Day of July, 2002

Attest:

*Attesting Officer*

JAMES E. ROGAN
*Director of the United States Patent and Trademark Office*

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Ala Pro Pro Ala Xaa Asp Pro Arg Leu Leu Asn Lys Met Leu Arg Asp
1               5                   10                  15

Ser His Val Leu His Xaa Arg Leu Xaa Gln Xaa Pro Asp Ile Tyr
            20              25              30
```

( 2 ) INFORMATION FOR SEQ ID NO:2:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Ala Pro Pro Ala Xaa Asp Pro Arg Leu Leu Asn Lys Met Leu Arg Asp
1               5                   10                  15

Ser His Val Leu His
            20
```

( 2 ) INFORMATION FOR SEQ ID NO:3:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Thr Gln Lys Glu Gln Thr Lys Ala Gln Asp Val Leu Gly Ala Val Ala
1               5                   10                  15

Leu
```

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GCNCCNCCNG CNTGYGA     17

( 2 ) INFORMATION FOR SEQ ID NO:5:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:5:

GCARTGYAAC ACRTGNGART C           21

( 2 ) INFORMATION FOR SEQ ID NO:6:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

Ala Pro Pro Ala Cys Asp Leu Arg Val Leu Ser Lys Leu Leu Arg Asp
1           5                   10                   15

Ser His Val Leu His
           20

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

GTACGCGTTC TAGANNNNNN T           21

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

AGTTTACTGA GGACTCGGAG G           21

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

TTCGGCCGGA TAGGCCTTTT TTTTTTTTTT           30

( 2 ) INFORMATION FOR SEQ ID NO:10:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:10:

TTCGGCCGGA TAGGCCTTTT TTTTTTTT 29

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

TGCGACCTCC GAGTCCTCAG 20

( 2 ) INFORMATION FOR SEQ ID NO:12:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

GAGTCCTCAG TAAACTGCTT CGT 23

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

GGAGTCACGA AGCAGTTTAC 20

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

CCTTTACTTC TAGGCCTG 18

( 2 ) INFORMATION FOR SEQ ID NO:15:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

GAGGTCACAA GCAGGAGGA                                                                            19

( 2 ) INFORMATION FOR SEQ ID NO:16:

( i ) SEQUENCE CHARACTERISTICS:
                ( A ) LENGTH: 19 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:16:

GGCATAGTCC GGGACGTCG                                                                            19

( 2 ) INFORMATION FOR SEQ ID NO:17:

( i ) SEQUENCE CHARACTERISTICS:
                ( A ) LENGTH: 19 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:17:

TCCTCCTGCT TGTGACCTC                                                                            19

( 2 ) INFORMATION FOR SEQ ID NO:18:

( i ) SEQUENCE CHARACTERISTICS:
                ( A ) LENGTH: 19 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:18:

CCAGGAAGGA TTCAGGGGA                                                                            19

( 2 ) INFORMATION FOR SEQ ID NO:19:

( i ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:19:

CAACAAGTCG ACCGCCAGCC AGACACCCCG                                                                30

( 2 ) INFORMATION FOR SEQ ID NO:20:

( i ) SEQUENCE CHARACTERISTICS:
                ( A ) LENGTH: 24 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:20:

```
GGCCGGATAG GCCACTCNNN NNNT                                          24
```

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

```
GCARTGYAAN ACRTGNGART C                                             21
```

( 2 ) INFORMATION FOR SEQ ID NO:22:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

```
TTGGTGTGCA CTTGTG                                                   16
```

( 2 ) INFORMATION FOR SEQ ID NO:23:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

```
CACAAGTGCA CACCAACCCC                                               20
```

( 2 ) INFORMATION FOR SEQ ID NO:24:

( i ) SEQUENCE CHARACTERISTICS:
        ( A ) LENGTH: 1342 base pairs
        ( B ) TYPE: nucleic acid
        ( C ) STRANDEDNESS: unknown
        ( D ) TOPOLOGY: unknown ( i i ) MOLECULE TYPE: cDNA ( i x ) FEATURE:
        ( A ) NAME/KEY: CDS
        ( B ) LOCATION: 36..1097

( i x ) FEATURE:
        ( A ) NAME/KEY: mat_peptide
        ( B ) LOCATION: 99..1097

( i x ) FEATURE:
        ( A ) NAME/KEY: sig_peptide
        ( B ) LOCATION: 36..98

( x i ) SEQUENCE DESCRIPTION: SEQ ID NO:24:

```
CAGGGAGCCA CGCCAGCCAA GACACCCCGG CCAGA ATG GAG CTG ACT GAA TTG      53
                                       Met Glu Leu Thr Glu Leu
                                       -21             -20

CTC CTC GTG GTC ATG CTT CTC CTA ACT GCA AGG CTA ACG CTG TCC AGC    101
Leu Leu Val Val Met Leu Leu Leu Thr Ala Arg Leu Thr Leu Ser Ser
-15              -10                 -5                   1
```

| | | | | | | | | | | | | | | | |
|---|---|---|---|---|---|---|---|---|---|---|---|---|---|---|---|
| CCG | GCT | CCT | CCT | GCT | TGT | GAC | CTC | CGA | GTC | CTC | AGT | AAA | CTG | CTT | CGT | 149 |
| Pro | Ala | Pro | Pro | Ala | Cys | Asp | Leu | Arg | Val | Leu | Ser | Lys | Leu | Leu | Arg | |
| | | | 5 | | | | 10 | | | | | 15 | | | | |
| GAC | TCC | CAT | GTC | CTT | CAC | AGC | AGA | CTG | AGC | CAG | TGC | CCA | GAG | GTT | CAC | 197 |
| Asp | Ser | His | Val | Leu | His | Ser | Arg | Leu | Ser | Gln | Cys | Pro | Glu | Val | His | |
| | | 20 | | | | 25 | | | | 30 | | | | | | |
| CCT | TTG | CCT | ACA | CCT | GTC | CTG | CTG | CCT | GCT | GTG | GAC | TTT | AGC | TTG | GGA | 245 |
| Pro | Leu | Pro | Thr | Pro | Val | Leu | Leu | Pro | Ala | Val | Asp | Phe | Ser | Leu | Gly | |
| | | 35 | | | | 40 | | | | 45 | | | | | | |
| GAA | TGG | AAA | ACC | CAG | ATG | GAG | GAG | ACC | AAG | GCA | CAG | GAC | ATT | CTG | GGA | 293 |
| Glu | Trp | Lys | Thr | Gln | Met | Glu | Glu | Thr | Lys | Ala | Gln | Asp | Ile | Leu | Gly | |
| 50 | | | | 55 | | | | 60 | | | | | | | 65 | |
| GCA | GTG | ACC | CTT | CTG | CTG | GAG | GGA | GTG | ATG | GCA | GCA | CGG | GGA | CAA | CTG | 341 |
| Ala | Val | Thr | Leu | Leu | Leu | Glu | Gly | Val | Met | Ala | Ala | Arg | Gly | Gln | Leu | |
| | | | 70 | | | | 75 | | | | 80 | | | | | |
| GGA | CCC | ACT | TGC | CTC | TCA | TCC | CTC | CTG | GGG | CAG | CTT | TCT | GGA | CAG | GTC | 389 |
| Gly | Pro | Thr | Cys | Leu | Ser | Ser | Leu | Leu | Gly | Gln | Leu | Ser | Gly | Gln | Val | |
| | | | 85 | | | | 90 | | | | 95 | | | | | |
| CGT | CTC | CTC | CTT | GGG | GCC | CTG | CAG | AGC | CTC | CTT | GGA | ACC | CAG | CTT | CCT | 437 |
| Arg | Leu | Leu | Leu | Gly | Ala | Leu | Gln | Ser | Leu | Leu | Gly | Thr | Gln | Leu | Pro | |
| | | 100 | | | | 105 | | | | 110 | | | | | | |
| CCA | CAG | GGC | AGG | ACC | ACA | GCT | CAC | AAG | GAT | CCC | AAT | GCC | ATC | TTC | CTG | 485 |
| Pro | Gln | Gly | Arg | Thr | Thr | Ala | His | Lys | Asp | Pro | Asn | Ala | Ile | Phe | Leu | |
| | 115 | | | | 120 | | | | 125 | | | | | | | |
| AGC | TTC | CAA | CAC | CTG | CTC | CGA | GGA | AAG | GTG | CGT | TTC | CTG | ATG | CTT | GTA | 533 |
| Ser | Phe | Gln | His | Leu | Leu | Arg | Gly | Lys | Val | Arg | Phe | Leu | Met | Leu | Val | |
| 130 | | | | 135 | | | | 140 | | | | | | | 145 | |
| GGA | GGG | TCC | ACC | CTC | TGC | GTC | AGG | CGG | GCC | CCA | CCC | ACC | ACA | GCT | GTC | 581 |
| Gly | Gly | Ser | Thr | Leu | Cys | Val | Arg | Arg | Ala | Pro | Pro | Thr | Thr | Ala | Val | |
| | | | 150 | | | | 155 | | | | 160 | | | | | |
| CCC | AGC | AGA | ACC | TCT | CTA | GTC | CTC | ACA | CTG | AAC | GAG | CTC | CCA | AAC | AGG | 629 |
| Pro | Ser | Arg | Thr | Ser | Leu | Val | Leu | Thr | Leu | Asn | Glu | Leu | Pro | Asn | Arg | |
| | | 165 | | | | 170 | | | | 175 | | | | | | |
| ACT | TCT | GGA | TTG | TTG | GAG | ACA | AAC | TTC | ACT | GCC | TCA | GCC | AGA | ACT | ACT | 677 |
| Thr | Ser | Gly | Leu | Leu | Glu | Thr | Asn | Phe | Thr | Ala | Ser | Ala | Arg | Thr | Thr | |
| | | 180 | | | | 185 | | | | 190 | | | | | | |
| GGC | TCT | GGG | CTT | CTG | AAG | TGG | CAG | CAG | GGA | TTC | AGA | GCC | AAG | ATT | CCT | 725 |
| Gly | Ser | Gly | Leu | Leu | Lys | Trp | Gln | Gln | Gly | Phe | Arg | Ala | Lys | Ile | Pro | |
| | 195 | | | | 200 | | | | 205 | | | | | | | |
| GGT | CTG | CTG | AAC | CAA | ACC | TCC | AGG | TCC | CTG | GAC | CAA | ATC | CCC | GGA | TAC | 773 |
| Gly | Leu | Leu | Asn | Gln | Thr | Ser | Arg | Ser | Leu | Asp | Gln | Ile | Pro | Gly | Tyr | |
| 210 | | | | 215 | | | | 220 | | | | | | | 225 | |
| CTG | AAC | AGG | ATA | CAC | GAA | CTC | TTG | AAT | GGA | ACT | CGT | GGA | CTC | TTT | CCT | 821 |
| Leu | Asn | Arg | Ile | His | Glu | Leu | Leu | Asn | Gly | Thr | Arg | Gly | Leu | Phe | Pro | |
| | | | 230 | | | | 235 | | | | 240 | | | | | |
| GGA | CCC | TCA | CGC | AGG | ACC | CTA | GGA | GCC | CCG | GAC | ATT | TCC | TCA | GGA | ACA | 869 |
| Gly | Pro | Ser | Arg | Arg | Thr | Leu | Gly | Ala | Pro | Asp | Ile | Ser | Ser | Gly | Thr | |
| | | | 245 | | | | 250 | | | | 255 | | | | | |
| TCA | GAC | ACA | GGC | TCC | CTG | CCA | CCC | AAC | CTC | CAG | CCT | GGA | TAT | TCT | CCT | 917 |
| Ser | Asp | Thr | Gly | Ser | Leu | Pro | Pro | Asn | Leu | Gln | Pro | Gly | Tyr | Ser | Pro | |
| | | 260 | | | | 265 | | | | 270 | | | | | | |
| TCC | CCA | ACC | CAT | CCT | CCT | ACT | GGA | CAG | TAT | ACG | CTC | TTC | CCT | CTT | CCA | 965 |
| Ser | Pro | Thr | His | Pro | Pro | Thr | Gly | Gln | Tyr | Thr | Leu | Phe | Pro | Leu | Pro | |
| | 275 | | | | 280 | | | | 285 | | | | | | | |
| CCC | ACC | TTG | CCC | ACC | CCT | GTG | GTC | CAG | CTC | CAC | CCC | CTG | CTT | CCT | GAC | 1013 |
| Pro | Thr | Leu | Pro | Thr | Pro | Val | Val | Gln | Leu | His | Pro | Leu | Leu | Pro | Asp | |
| 290 | | | | 295 | | | | 300 | | | | | | | 305 | |
| CCT | TCT | GCT | CCA | ACG | CCC | ACC | CCT | ACC | AGC | CCT | CTT | CTA | AAC | ACA | TCC | 1061 |
| Pro | Ser | Ala | Pro | Thr | Pro | Thr | Pro | Thr | Ser | Pro | Leu | Leu | Asn | Thr | Ser | |
| | | | 310 | | | | 315 | | | | 320 | | | | | |

-continued

```
TAC ACC CAC TCC CAG AAT CTG TCT CAG GAA GGG TAA GGTTCTCAGA              1107
Tyr Thr His Ser Gln Asn Leu Ser Gln Glu Gly  *
            325                 330

CACTGCCGAC ATCAGCATTG TCTCGTGTAC AGCTCCCTTC CCTGCAGGGC GCCCCTGGGA       1167

GACAACTGGA CAAGATTTCC TACTTTCTCC TGAAACCCAA AGCCCTGGTA AAAGGGATAC       1227

ACAGGACTGA AAAGGGAATC ATTTTCACT GTACATTATA AACCTTCAGA AGCTATTTTT        1287

TTAAGCTATC AGCAATACTC ATCAGAGCAG CTAGCTCTTT GGTCTATTTT CTGCA            1342
```

( 2 ) INFORMATION FOR SEQ ID NO:25:

( i ) SEQUENCE CHARACTERISTICS:
        ( A ) LENGTH: 353 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
Met Glu Leu Thr Glu Leu Leu Val Val Met Leu Leu Thr Ala
-21 -20             -15                 -10

Arg Leu Thr Leu Ser Ser Pro Ala Pro Pro Ala Cys Asp Leu Arg Val
 -5               1             5                     10

Leu Ser Lys Leu Leu Arg Asp Ser His Val Leu His Ser Arg Leu Ser
            15                 20                 25

Gln Cys Pro Glu Val His Pro Leu Pro Thr Pro Val Leu Leu Pro Ala
        30                 35                 40

Val Asp Phe Ser Leu Gly Glu Trp Lys Thr Gln Met Glu Glu Thr Lys
    45                 50                 55

Ala Gln Asp Ile Leu Gly Ala Val Thr Leu Leu Leu Glu Gly Val Met
60                 65                 70                 75

Ala Ala Arg Gly Gln Leu Gly Pro Thr Cys Leu Ser Ser Leu Leu Gly
            80                 85                 90

Gln Leu Ser Gly Gln Val Arg Leu Leu Leu Gly Ala Leu Gln Ser Leu
            95                 100                105

Leu Gly Thr Gln Leu Pro Pro Gln Gly Arg Thr Thr Ala His Lys Asp
        110                115                120

Pro Asn Ala Ile Phe Leu Ser Phe Gln His Leu Leu Arg Gly Lys Val
    125                130                135

Arg Phe Leu Met Leu Val Gly Gly Ser Thr Leu Cys Val Arg Arg Ala
140                145                150                155

Pro Pro Thr Thr Ala Val Pro Ser Arg Thr Ser Leu Val Leu Thr Leu
            160                165                170

Asn Glu Leu Pro Asn Arg Thr Ser Gly Leu Leu Glu Thr Asn Phe Thr
        175                180                185

Ala Ser Ala Arg Thr Thr Gly Ser Gly Leu Leu Lys Trp Gln Gln Gly
        190                195                200

Phe Arg Ala Lys Ile Pro Gly Leu Leu Asn Gln Thr Ser Arg Ser Leu
    205                210                215

Asp Gln Ile Pro Gly Tyr Leu Asn Arg Ile His Glu Leu Leu Asn Gly
220                225                230                235

Thr Arg Gly Leu Phe Pro Gly Pro Ser Arg Arg Thr Leu Gly Ala Pro
            240                245                250

Asp Ile Ser Ser Gly Thr Ser Asp Thr Gly Ser Leu Pro Pro Asn Leu
            255                260                265

Gln Pro Gly Tyr Ser Pro Ser Pro Thr His Pro Pro Thr Gly Gln Tyr
        270                275                280
```

```
Thr Leu Phe Pro Leu Pro Pro Thr Leu Pro Thr Pro Val Val Gln Leu
    285                 290                 295

His Pro Leu Leu Pro Asp Pro Ser Ala Pro Thr Pro Thr Pro Thr Ser
300                 305                 310                 315

Pro Leu Leu Asn Thr Ser Tyr Thr His Ser Gln Asn Leu Ser Gln Glu
                320                 325                 330

Gly
```

( 2 ) INFORMATION FOR SEQ ID NO:26:

( i ) SEQUENCE CHARACTERISTICS:
        ( A ) LENGTH: 1164 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 34..894

( i x ) FEATURE:
        ( A ) NAME/KEY: mat_peptide
        ( B ) LOCATION: 97..894

( i x ) FEATURE:
        ( A ) NAME/KEY: sig_peptide
        ( B ) LOCATION: 34..96

( x i ) SEQUENCE DESCRIPTION: SEQ ID NO:26:

```
AGGGAGCCAC GCCAGCCAGA CACCCCGGCC AGA ATG GAG CTG ACT GAA TTG CTC       54
                                    Met Glu Leu Thr Glu Leu Leu
                                    -21 -20                  -15

CTC GTG GTC ATG CTT CTC CTA ACT GCA AGG CTA ACG CTG TCC AGC CCG       102
Leu Val Val Met Leu Leu Leu Thr Ala Arg Leu Thr Leu Ser Ser Pro
            -10                  -5                           1

GCT CCT CCT GCT TGT GAC CTC CGA GTC CTC AGT AAA CTG CTT CGT GAC       150
Ala Pro Pro Ala Cys Asp Leu Arg Val Leu Ser Lys Leu Leu Arg Asp
         5                  10                  15

TCC CAT GTC CTT CAC AGC AGA CTG AGC CAG TGC CCA GAG GTT CAC CCT       198
Ser His Val Leu His Ser Arg Leu Ser Gln Cys Pro Glu Val His Pro
     20                  25                  30

TTG CCT ACA CCT GTC CTG CTG CCT GCT GTG GAC TTT AGC TTG GGA GAA       246
Leu Pro Thr Pro Val Leu Leu Pro Ala Val Asp Phe Ser Leu Gly Glu
 35                  40                  45                  50

TGG AAA ACC CAG ATG GAG GAG ACC AAG GCA CAG GAC ATT CTG GGA GCA       294
Trp Lys Thr Gln Met Glu Glu Thr Lys Ala Gln Asp Ile Leu Gly Ala
                 55                  60                  65

GTG ACC CTT CTG CTG GAG GGA GTG ATG GCA GCA CGG GGA CAA CTG GGA       342
Val Thr Leu Leu Leu Glu Gly Val Met Ala Ala Arg Gly Gln Leu Gly
             70                  75                  80

CCC ACT TGC CTC TCA TCC CTC CTG GGG CAG CTT TCT GGA CAG GTC CGT       390
Pro Thr Cys Leu Ser Ser Leu Leu Gly Gln Leu Ser Gly Gln Val Arg
         85                  90                  95

CTC CTC CTT GGG GCC CTG CAG AGC CTC CTT GGA ACC CAG CTT CCT CCA       438
Leu Leu Leu Gly Ala Leu Gln Ser Leu Leu Gly Thr Gln Leu Pro Pro
     100                 105                 110

CAG GGC AGG ACC ACA GCT CAC AAG GAT CCC AAT GCC ATC TTC CTG AGC       486
Gln Gly Arg Thr Thr Ala His Lys Asp Pro Asn Ala Ile Phe Leu Ser
115                 120                 125                 130

TTC CAA CAC CTG CTC CGA GGA AAG GAC TTC TGG ATT GTT GGA GAC AAA       534
Phe Gln His Leu Leu Arg Gly Lys Asp Phe Trp Ile Val Gly Asp Lys
                135                 140                 145
```

| | | | | | | | | | | | | | | | |
|---|---|---|---|---|---|---|---|---|---|---|---|---|---|---|---|
|CTT|CAC|TGC|CTC|AGC|CAG|AAC|TAC|TGG|CTC|TGG|GCT|TCT|GAA|GTG|GCA|
|Leu|His|Cys|Leu|Ser|Gln|Asn|Tyr|Trp|Leu|Trp|Ala|Ser|Glu|Val|Ala|
| |150| | | | |155| | | |160| | | | | |

582

| | | | | | | | | | | | | | | | |
|---|---|---|---|---|---|---|---|---|---|---|---|---|---|---|---|
|GCA|GGG|ATT|CAG|AGC|CAA|GAT|TCC|TGG|TCT|GCT|GAA|CCA|AAC|CTC|CAG|
|Ala|Gly|Ile|Gln|Ser|Gln|Asp|Ser|Trp|Ser|Ala|Glu|Pro|Asn|Leu|Gln|
| | |165| | | |170| | | |175| | | | | |

630

| | | | | | | | | | | | | | | | |
|---|---|---|---|---|---|---|---|---|---|---|---|---|---|---|---|
|GTC|CCT|GGA|CCA|AAT|CCC|CGG|ATA|CCT|GAA|CAG|GAT|ACA|CGA|ACT|CTT|
|Val|Pro|Gly|Pro|Asn|Pro|Arg|Ile|Pro|Glu|Gln|Asp|Thr|Arg|Thr|Leu|
| |180| | | |185| | | |190| | | | | | |

678

| | | | | | | | | | | | | | | | |
|---|---|---|---|---|---|---|---|---|---|---|---|---|---|---|---|
|GAA|TGG|AAC|TCG|TGG|ACT|CTT|TCC|TGG|ACC|CTC|ACG|CAG|GAC|CCT|AGG|
|Glu|Trp|Asn|Ser|Trp|Thr|Leu|Ser|Trp|Thr|Leu|Thr|Gln|Asp|Pro|Arg|
|195| | | | |200| | | | |205| | | | |210|

726

| | | | | | | | | | | | | | | | |
|---|---|---|---|---|---|---|---|---|---|---|---|---|---|---|---|
|AGC|CCC|GGA|CAT|TTC|CTC|AGG|AAC|ATC|AGA|CAC|AGG|CTC|CCT|GCC|ACC|
|Ser|Pro|Gly|His|Phe|Leu|Arg|Asn|Ile|Arg|His|Arg|Leu|Pro|Ala|Thr|
| | | |215| | | | |220| | | | |225| | |

774

| | | | | | | | | | | | | | | | |
|---|---|---|---|---|---|---|---|---|---|---|---|---|---|---|---|
|CAA|CCT|CCA|GCC|TGG|ATA|TTC|TCC|TTC|CCC|AAC|CCA|TCC|TCC|TAC|TGG|
|Gln|Pro|Pro|Ala|Trp|Ile|Phe|Ser|Phe|Pro|Asn|Pro|Ser|Ser|Tyr|Trp|
| | | |230| | | | |235| | | | |240| | |

822

| | | | | | | | | | | | | | | | |
|---|---|---|---|---|---|---|---|---|---|---|---|---|---|---|---|
|ACA|GTA|TAC|GCT|CTT|CCC|TCT|TCC|ACC|CAC|CTT|GCC|CAC|CCC|TGT|GGT|
|Thr|Val|Tyr|Ala|Leu|Pro|Ser|Ser|Thr|His|Leu|Ala|His|Pro|Cys|Gly|
| | |245| | | | |250| | | | |255| | | |

870

| | | | | | | | | | |
|---|---|---|---|---|---|---|---|---|---|
|CCA|GCT|CCA|CCC|CCT|GCT|TCC|TGA|CCCTTCTGCT|CCAACGCCCA CCCCTACCAG|
|Pro|Ala|Pro|Pro|Pro|Ala|Ser|*| | |
| |260| | | | |265| | | |

924

CCCTCTTCTA AACACATCCT ACACCCACTC CCAGAATCTG TCTCAGGAAG GGTAAGGTTC  984

TCAGACACTG CCGACATCAG CATTGTCTCG TGTACAGCTC CCTTCCCTGC AGGGCGCCCC  1044

TGGGAGACAA CTGGACAAGA TTTCCTACTT TCTCCTGAAA CCCAAAGCCC TGGTAAAAGG  1104

GATACACAGG ACTGAAAAGG GAATCATTTT TCACTGTACA TTATAAACCT TCAGAAGCTA  1164

( 2 ) INFORMATION FOR SEQ ID NO:27:

( i ) SEQUENCE CHARACTERISTICS:
    ( A ) LENGTH: 286 amino acids
    ( B ) TYPE: amino acid
    ( D ) TOPOLOGY: linear ( i i ) MOLECULE TYPE: protein ( x i ) SEQUENCE DESCRIPTION: SEQ ID NO:27:

| | | | | | | | | | | | | | | |
|---|---|---|---|---|---|---|---|---|---|---|---|---|---|---|
|Met|Glu|Leu|Thr|Glu|Leu|Leu|Leu|Val|Val|Met|Leu|Leu|Leu|Thr|Ala|
|-21|-20| | | |-15| | | | |-10| | | | |

| | | | | | | | | | | | | | | |
|---|---|---|---|---|---|---|---|---|---|---|---|---|---|---|
|Arg|Leu|Thr|Leu|Ser|Ser|Pro|Ala|Pro|Ala|Cys|Asp|Leu|Arg|Val|
|-5| | | | |1| | | |5| | | | |10|

| | | | | | | | | | | | | | | |
|---|---|---|---|---|---|---|---|---|---|---|---|---|---|---|
|Leu|Ser|Lys|Leu|Leu|Arg|Asp|Ser|His|Val|Leu|His|Ser|Arg|Leu|Ser|
| | |15| | | | |20| | | | |25| | | |

| | | | | | | | | | | | | | | |
|---|---|---|---|---|---|---|---|---|---|---|---|---|---|---|
|Gln|Cys|Pro|Glu|Val|His|Pro|Leu|Pro|Thr|Pro|Val|Leu|Leu|Pro|Ala|
| | |30| | | | |35| | | | |40| | | |

| | | | | | | | | | | | | | | |
|---|---|---|---|---|---|---|---|---|---|---|---|---|---|---|
|Val|Asp|Phe|Ser|Leu|Gly|Glu|Trp|Lys|Thr|Gln|Met|Glu|Glu|Thr|Lys|
| |45| | | | |50| | | | |55| | | | |

| | | | | | | | | | | | | | | |
|---|---|---|---|---|---|---|---|---|---|---|---|---|---|---|
|Ala|Gln|Asp|Ile|Leu|Gly|Ala|Val|Thr|Leu|Leu|Leu|Glu|Gly|Val|Met|
|60| | | | |65| | | | |70| | | | |75|

| | | | | | | | | | | | | | | |
|---|---|---|---|---|---|---|---|---|---|---|---|---|---|---|
|Ala|Ala|Arg|Gly|Gln|Leu|Gly|Pro|Thr|Cys|Leu|Ser|Ser|Leu|Leu|Gly|
| | | |80| | | | |85| | | | |90| | |

| | | | | | | | | | | | | | | |
|---|---|---|---|---|---|---|---|---|---|---|---|---|---|---|
|Gln|Leu|Ser|Gly|Gln|Val|Arg|Leu|Leu|Leu|Gly|Ala|Leu|Gln|Ser|Leu|
| | | |95| | | | |100| | | | |105| | |

| | | | | | | | | | | | | | | |
|---|---|---|---|---|---|---|---|---|---|---|---|---|---|---|
|Leu|Gly|Thr|Gln|Leu|Pro|Pro|Gln|Gly|Arg|Thr|Thr|Ala|His|Lys|Asp|
| | |110| | | | |115| | | | |120| | | |

-continued

| Pro | Asn 125 | Ala | Ile | Phe | Leu | Ser 130 | Phe | Gln | His | Leu | Leu 135 | Arg | Gly | Lys | Asp |
|---|---|---|---|---|---|---|---|---|---|---|---|---|---|---|---|
| Phe 140 | Trp | Ile | Val | Gly | Asp 145 | Lys | Leu | His | Cys | Leu 150 | Ser | Gln | Asn | Tyr | Trp 155 |
| Leu | Trp | Ala | Ser | Glu 160 | Val | Ala | Ala | Gly | Ile 165 | Gln | Ser | Gln | Asp | Ser 170 | Trp |
| Ser | Ala | Glu | Pro 175 | Asn | Leu | Gln | Val | Pro 180 | Gly | Pro | Asn | Pro | Arg 185 | Ile | Pro |
| Glu | Gln | Asp 190 | Thr | Arg | Thr | Leu | Glu 195 | Trp | Asn | Ser | Trp | Thr 200 | Leu | Ser | Trp |
| Thr | Leu 205 | Thr | Gln | Asp | Pro | Arg 210 | Ser | Pro | Gly | His | Phe 215 | Leu | Arg | Asn | Ile |
| Arg 220 | His | Arg | Leu | Pro | Ala 225 | Thr | Gln | Pro | Pro | Ala 230 | Trp | Ile | Phe | Ser | Phe 235 |
| Pro | Asn | Pro | Ser | Ser 240 | Tyr | Trp | Thr | Val | Tyr 245 | Ala | Leu | Pro | Ser | Ser 250 | Thr |
| His | Leu | Ala | His 255 | Pro | Cys | Gly | Pro | Ala 260 | Pro | Pro | Pro | Ala | Ser 265 | | |